US007968684B2

(12) United States Patent
Ghayur et al.

(10) Patent No.: US 7,968,684 B2
(45) Date of Patent: Jun. 28, 2011

(54) IL-18 BINDING PROTEINS

(75) Inventors: Tariq Ghayur, Holliston, MA (US);
Boris Labkovsky, Wales, MA (US);
Jeffrey W. Voss, Holden, MA (US);
Larry Green, San Francisco, CA (US);
John Babcook, Vancouver (CA);
Xiao-chi Jia, Los Angeles, CA (US);
James Wieler, Beverly, MA (US);
Jaspal Singh Kang, Surrey (CA); Brad Hedberg, Vancouver (CA)

(73) Assignee: Abbott Laboratories, Abbott Park, IL (US)

( * ) Notice: Subject to any disclaimer, the term of this patent is extended or adjusted under 35 U.S.C. 154(b) by 520 days.

(21) Appl. No.: 10/988,360

(22) Filed: Nov. 12, 2004

(65) Prior Publication Data
US 2005/0147610 A1 Jul. 7, 2005

Related U.S. Application Data

(60) Provisional application No. 60/519,474, filed on Nov. 12, 2003.

(51) Int. Cl.
*C07K 16/00* (2006.01)
*A61K 39/395* (2006.01)
*C12N 1/11* (2006.01)
*C12N 1/15* (2006.01)
*C12N 1/21* (2006.01)
*C12N 5/04* (2006.01)
*C12N 5/07* (2006.01)
*C12N 15/09* (2006.01)
*C12N 15/11* (2006.01)
*C12N 15/13* (2006.01)
*C12N 15/63* (2006.01)

(52) U.S. Cl. ............ 530/387.1; 530/387.3; 530/388.1; 530/388.23; 530/391.3; 530/391.7; 424/130.1; 424/133.1; 424/145.1; 424/178.1; 435/69.1; 435/320.1; 435/69.7; 435/325; 435/326; 435/328; 435/335; 435/348; 435/349; 435/358; 435/365; 435/365.1; 435/410; 435/419; 435/252.3; 435/252.33; 435/254.11; 435/254.21; 536/23.1; 536/23.4; 536/23.5; 536/23.53

(58) Field of Classification Search ............... None
See application file for complete search history.

(56) References Cited

U.S. PATENT DOCUMENTS

| 5,019,385 | A | 5/1991 | Mitsuhashi |
| 5,545,806 | A | 8/1996 | Lonberg et al. |
| 5,545,807 | A | 8/1996 | Surani et al. |
| 5,597,669 | A | 1/1997 | Hamada et al. |
| 5,612,205 | A | 3/1997 | Kay et al. |
| 5,625,126 | A | 4/1997 | Lonberg et al. |
| 5,625,825 | A | 4/1997 | Rostoker et al. |
| 5,627,052 | A | 5/1997 | Schrader |
| 5,633,425 | A | 5/1997 | Lonberg et al. |
| 5,643,763 | A | 7/1997 | Dunn et al. |
| 5,661,016 | A | 8/1997 | Lonberg et al. |
| 5,721,367 | A | 2/1998 | Kay et al. |
| 5,770,429 | A | 6/1998 | Lonberg et al. |
| 5,789,215 | A | 8/1998 | Berns et al. |
| 5,789,650 | A | 8/1998 | Lonberg et al. |
| 5,814,318 | A | 9/1998 | Lonberg et al. |
| 5,891,663 | A | 4/1999 | Tanimoto |
| 5,912,324 | A | 6/1999 | Okamura et al. |
| 5,914,253 | A | 6/1999 | Okamura et al. |
| 5,916,771 | A | 6/1999 | Hori et al. |
| 5,939,598 | A | 8/1999 | Kucherlapati et al. |
| 5,985,615 | A | 11/1999 | Jakobovits et al. |
| 5,994,619 | A | 11/1999 | Stice et al. |
| 5,998,209 | A | 12/1999 | Jokobovits et al. |
| 6,054,487 | A | 4/2000 | Sekut et al. |
| 6,060,283 | A | 5/2000 | Okura et al. |
| 6,075,181 | A | 6/2000 | Kucherlapati et al. |
| 6,087,116 | A | 7/2000 | Torigoe |
| 6,091,001 | A | 7/2000 | Jakobovits et al. |
| 6,114,598 | A | 9/2000 | Kucherlapati et al. |
| 6,130,364 | A | 10/2000 | Jakobovits et al. |
| 6,180,370 | B1 * | 1/2001 | Queen et al. ............ 435/69.6 |
| 6,197,297 | B1 | 3/2001 | Kunikata |
| 6,207,641 | B1 | 3/2001 | Torigoe |

(Continued)

FOREIGN PATENT DOCUMENTS

CN 101177454 B 5/2008

(Continued)

OTHER PUBLICATIONS

Rudikoff et al., Proc. Natl. Acad. Sci, USA, 1982, vol. 79:1979-1983.*
Alberts et al., The Cell, 2002, Garland Science, 4th edition, esp. pp. 161, Fig. 3-42.*
Holliger et al., Nature Biotech., 2005, 23(9):1126-1136.*
Queen et al., PNAS, 1989, 86:10029-10033.*
Riechmann et al., Nature, 1988, 332:323-327.*
Adachi O. et al., "Targeted Disruption of the MyD88 Gene Results in Loss of IL-1- and IL-18-Mediated Function", Immunity, (1998); 9:143-150.

(Continued)

*Primary Examiner* — Elizabeth C. Kemmerer
*Assistant Examiner* — Xiaozhen Xie
(74) *Attorney, Agent, or Firm* — McCarter & English, LLP; Maria Laccotripe Zacharakis; Maneesh Gulati, Esq.

(57) ABSTRACT

The present invention encompasses IL-18 binding proteins, particularly antibodies that bind human interleukin-18 (hIL-18). Specifically, the invention relates to antibodies that are entirely human antibodies. Preferred antibodies have high affinity for hIL-18 and/or that neutralize hIL-18 activity in vitro and in vivo. An antibody of the invention can be a full-length antibody or an antigen-binding portion thereof. Method of making and method of using the antibodies of the invention are also provided. The antibodies, or antibody portions, of the invention are useful for detecting hIL-18 and for inhibiting hIL-18 activity, e.g., in a human subject suffering from a disorder in which hIL-18 activity is detrimental.

64 Claims, No Drawings

U.S. PATENT DOCUMENTS

| | | |
|---|---|---|
| 6,214,584 B1 | 4/2001 | Ushio |
| 6,242,255 B1 | 6/2001 | Akita |
| 6,268,486 B1 | 7/2001 | Kunikata |
| 6,274,709 B1 | 8/2001 | Okamura et al. |
| 6,277,598 B1 | 8/2001 | Okamura et al. |
| 6,309,636 B1 * | 10/2001 | do Couto et al. .......... 424/133.1 |
| 7,041,294 B2 | 11/2001 | Staats |
| 7,417,029 B2 | 1/2002 | Wannamaker |
| 6,403,079 B1 | 6/2002 | Akita |
| 6,441,138 B2 | 8/2002 | Akita |
| 6,476,197 B1 | 11/2002 | Yamamoto |
| 6,509,449 B1 | 1/2003 | Kunikata |
| 6,693,171 B2 | 1/2003 | Sims |
| 7,169,581 B2 | 1/2003 | Sims |
| 6,559,298 B1 | 5/2003 | Torigoe |
| 6,692,740 B2 | 5/2003 | Sims |
| 6,589,764 B1 | 7/2003 | Sims |
| 6,600,022 B1 | 7/2003 | Torigoe |
| 7,186,528 B2 | 7/2003 | Kirkpatrick |
| 6,605,280 B1 | 8/2003 | Novick |
| 7,141,393 B2 | 10/2003 | Torigoe |
| 6,664,077 B1 | 12/2003 | Sims |
| 7,253,260 B2 | 12/2003 | Janson |
| 6,706,487 B1 | 3/2004 | Abdel-Meguid et al. |
| 7,279,155 B2 | 6/2004 | Dinarello |
| 6,790,442 B1 | 9/2004 | Okura |
| 7,098,373 B2 | 9/2004 | Mizutani |
| 7,311,902 B2 | 1/2005 | Bam |
| 7,557,084 B2 | 10/2005 | Karow |
| 7,442,526 B2 | 8/2006 | Johanson |
| 7,135,458 B1 | 11/2006 | Ushio et al. |
| 7,491,803 B2 | 12/2006 | Sugimura |
| 7,355,014 B2 | 2/2007 | Ushio |
| 7,439,336 B2 | 12/2007 | Kornmann |
| 2002/0098185 A1 | 7/2002 | Sims |
| 2003/0003542 A1 | 1/2003 | Sims |
| 2003/0100062 A1 | 5/2003 | Sims |
| 2003/0133919 A1 | 7/2003 | Torigoe |
| 2003/0157094 A1 | 8/2003 | Chvatchko |
| 2003/0199040 A1 | 10/2003 | Sims |
| 2003/0232032 A1 | 12/2003 | Janson |
| 2004/0037829 A1 | 2/2004 | Novick |
| 2004/0076628 A1 | 4/2004 | Chvatchko |
| 2004/0138421 A1 | 7/2004 | Sims |
| 2004/0234523 A1 | 11/2004 | Dinarello |
| 2004/0248254 A1 | 12/2004 | Sims |
| 2005/0064541 A1 | 3/2005 | Novick |
| 2006/0039892 A1 | 2/2006 | Dede |
| 2006/0110389 A1 | 5/2006 | Nishida |
| 2006/0154294 A1 | 7/2006 | Novick |
| 2006/0177871 A1 | 8/2006 | Janson |
| 2006/0233799 A1 | 10/2006 | Chvatchko |
| 2007/0173439 A1 | 7/2007 | Novick |
| 2007/0196895 A1 | 8/2007 | Aloni |
| 2007/0212329 A1 | 9/2007 | Bruck |
| 2007/0237776 A1 | 10/2007 | Huang |
| 2007/0264237 A1 | 11/2007 | Rubinstein |
| 2007/0292432 A1 | 12/2007 | Ellis |
| 2008/0003216 A1 | 1/2008 | Dinarello |
| 2008/0063644 A1 | 3/2008 | Sekiyama |
| 2008/0076708 A1 | 3/2008 | Altarocca |
| 2008/0090766 A1 | 4/2008 | Hoshino |
| 2008/0199913 A1 | 8/2008 | Weber |
| 2008/0213576 A1 | 9/2008 | Sims |
| 2008/0274078 A1 | 11/2008 | Haskova |
| 2008/0292590 A1 | 11/2008 | Becher |
| 2008/0317710 A1 | 12/2008 | Becher |
| 2009/0016987 A1 | 1/2009 | Aikawa |
| 2009/0035258 A1 | 2/2009 | Haskova |
| 2009/0297517 A1 | 12/2009 | Sims |
| 2010/0034833 A1 | 2/2010 | Huang |

FOREIGN PATENT DOCUMENTS

| | | |
|---|---|---|
| EP | 0 850 952 A1 | 7/1998 |
| EP | 0 864 585 A1 | 9/1998 |
| EP | 864585 A1 | 9/1998 |
| EP | 0 962 531 A2 | 12/1999 |
| EP | 0 974 600 A2 | 1/2000 |
| EP | 0 712 931 B1 | 2/2001 |
| EP | 1101772 A1 | 5/2001 |
| EP | 1425028 B1 | 6/2004 |
| EP | 1433484 B1 | 6/2004 |
| EP | 1573032 B1 | 9/2005 |
| EP | 1720979 B1 | 9/2005 |
| EP | 1749838 A1 | 2/2007 |
| EP | 1761552 B1 | 3/2007 |
| EP | 1808446 A1 | 7/2007 |
| EP | 1938802 A1 | 7/2008 |
| WO | WO 91/10741 | 7/1991 |
| WO | WO 91/17271 | 11/1991 |
| WO | WO 92/01047 | 1/1992 |
| WO | WO 92/02551 | 2/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 94/02602 | 2/1994 |
| WO | WO 96/33735 | 10/1996 |
| WO | WO 96/34096 | 10/1996 |
| WO | WO 97/24441 | 7/1997 |
| WO | WO 97/29131 | 8/1997 |
| WO | WO 98/16654 | 4/1998 |
| WO | WO 98/24893 | 6/1998 |
| WO | WO 98/41232 | 9/1998 |
| WO | WO 98/50433 | 11/1998 |
| WO | WO 99/09063 | 2/1999 |
| WO | WO 99/22760 | 5/1999 |
| WO | WO 99/25044 | 5/1999 |
| WO | WO 99/37772 | 7/1999 |
| WO | WO 99/37773 | 7/1999 |
| WO | WO 99/45031 | 9/1999 |
| WO | WO 99/53049 | 10/1999 |
| WO | WO 00/09560 | 2/2000 |
| WO | WO 00/37504 | 6/2000 |
| WO | WO 00/12555 | 9/2000 |
| WO | WO 00/56772 | 9/2000 |
| WO | WO 01/58956 A2 * | 8/2001 |
| WO | WO 01/83525 A2 | 11/2001 |
| WO | WO 02/072636 A2 | 9/2002 |
| WO | WO2004101617 A1 | 11/2004 |
| WO | WO2005014618 A2 | 2/2005 |
| WO | WO2005014642 A2 | 2/2005 |
| WO | WO2005049649 A1 | 2/2005 |
| WO | WO2005039634 | 5/2005 |
| WO | WO2005063290 | 7/2005 |
| WO | WO2005083058 A1 | 9/2005 |
| WO | WO2005012352 A1 | 10/2005 |
| WO | WO2006009114 A | 1/2006 |
| WO | WO2006023623 | 3/2006 |
| WO | WO2006128908 A1 | 12/2006 |
| WO | WO2006128911 A2 | 12/2006 |
| WO | WO2008060319 A1 | 5/2008 |
| WO | WO2008109432 A2 | 9/2008 |
| WO | WO2008118733 A2 | 10/2008 |
| WO | WO2008118736 A1 | 10/2008 |
| WO | WO2008150431 A1 | 12/2008 |
| WO | WO2009015284 A2 | 1/2009 |
| WO | WO2010020593 | 2/2010 |
| WO | WO2010040736 | 4/2010 |

OTHER PUBLICATIONS

Akita, K. et al., "Involvement of Caspase-1 and Caspase-3 in the Production and Processing of Mature Human Interleukin 18 in Monocytic THP.1 Cells", J. Biol. Chem., (1997); 272:26595-26603.

Azzazy H., and Highsmith W.E., "Phage display technology: clinical applications and recent innovations", Clin. Biochem. (2002); 35:425-445.

Babcock, J.S. et al., "A novel strategy for generating monoclonal antibodies from single, isolated lymphocytes producing antibodies of defined specificities", Proc. Natl. Acad. Sci. USA, (1996): 93:7843-7848.

Barbas, C. et al., "Assembly of combinatorial antibody libraries on phage surfaces: The gene III site", Proc. Natl Acad. Sci. USA, (1991); 88:7978-7982.

Bendele, A. et al., "Animal models of Arthritis: Relevance to Human Disease", Toxicol Pathol., (1999); 27:134-142.
Bird, R. et al., "Single-Chain Antigen-Binding Proteins", Science, (1988); 242:423-426.
Clackson, T. et al., "Making Antibody Fragments Using Phage Display Libraries", Nature, (1991); 352:624-628.
Dinarello, C. et al., "Overview of interleukin-18: more than an interon-y inducing factor", J. Leukoc. Biol., (1998); 63:658-654.
Dinarello, C.A., "Interleukin-18", Methods, (1999); 19:121-132.
Dinarello, C.A., "IL-18: A T H1-inducing, proinflammatory cytokine and new member of the IL-1 family", J. Allergy Clin. Immunol., (1999); 103:11-24.
Durocher et al., "High-level and high-throughput recombinant protein reduction by transient transfection of suspension growing human 293-EBNA1 cells", Nucleic Acids Research, (2002); 30:1-9.
Fuchs, P. et al., "Targeting recombinant antibodies to the surface of *Escherichia coli*: fusion to a peptidoglycan associated lipoprotein", Bio/Technology, (1991); 9:1370-1372.
Garrad, L et al., "FAB assembly and enrichment in a monovalent phage display system", Bio/Technology, (1991); 9:1373-1377.
Gavilondo, J.V. et al., "Antibody Engineering at the Millennium", BioTechniques, (2002); 29:128-145.
Ghayur, T. et al., "Caspase-1 processes IFN-y- inducing factor and regulates LPS-induced IFN-y production", Nature, (1997); 386:619-623.
Ghetie, V., et al, "Increasing the serum persistence of an IgG fragment by random mutagenesis", Nat. Biotechnol., (1997); 15:637-640.
Gracie, J. A. et al., "Interleukin-18", Journal of Leukocyte Biology, (2003); 73, 213-224.
Gram, H. et al., "In vitro selection and affinity maturation of antibodies from a naive combinatorial immunoglobulin library", Proc. Natl. Acad. Sci. USA (1992); 89:3576-3580.
Green,L. et al., "Antigen-specific human monoclonal antiodies from mice engineered with human Ig heavy and light chain YACs", Nature Genetics (1994); 7:13-21.
Green, L. et al., "Regulation of B cell development by variable gene complexity in mice reconstituted with human immunoglobulin yeast artificial chromosomes", J. Exp. Med., (1998); 188:483-495.
Griffiths, A. et al., "Human anti-self antibodies with high specificity from phage display libraries", EMBO J., (1993); 12:725-734.
Gu, Y. et al., "Activation of Interferon-y inducing factor mediated by interleukin-1B converting enzyme", Science, (1997); 275:206-209.
Hay,B. et al., "Bacteriophage cloning and *Escherichia coli*expression of a human IgM Fab", Hum Antibod Hybridomas, (1992); 3:81-85.
Hawkins, R. et al., "Selection of phage antibodies by binding affinity", J Mol Biol., (1992); 226:889-896.
Hezareh, M. et al., "Effector function activities of a panel of mutants of a broadly neutralizing antibody against human immunodeficiency virus type 1", J. Virology, (2001); 75 (24):12161-12168.
Holliger, P. et al., "Diabodies": Small bivalent and bispecific antibody fragments, Proc. Natl. Acad. Sci. USA, (1993); 90:6444-6448.
Hoogenboom, H. et al., "Multi-subunit proteins on the surface of filamentous phage: methodologies for displaying antibody (Fab)heavy and light chains", Nuc Acid Res, (1991); 19:4133-4137.
Hoogenboom, H., Designing and optimizing library selection strategies for generating high-affinity antibodies, TIB Tech., (1997); 15:62-70.
Hoogenboom, H. et al., "Natural and designer binding sites made by phage display technology", Immunology Today, (2000); 21:371-378.
Huston, J. et al., "Protein engineering of antibody binding sites: Recovery of specific activity in an anti-digoxin single-chain Fv analogue produced in *Escherichia coli*", Proc. Natl. Acad. Sci. USA, (1988); 85:5879-5883.
Hoshino, K. et al., "Cutting Edge: Generation of Il-18 receptor-deficient Mice: Evidence for Il-1 receptor related protein as an essential Il-18 binding receptor", J. Immunol., (1999); 162:5041-5044.
Huse, W. et al., "Generation of a large combinatorial library of the immunoglobulin repertoire in phage lambda", Science, (1989); 246:1275-1281.
Johnnson, B. et al., "Immobilization of proteins to a carboxymethyldextran-midified gold surface for biospecific interaction analysis in surface plasmon resonance sensors", Anal. Biochem. (1991) 198:268-277.
Johnsson, B. et al., "Comparison of methods for immobilization to carboxymethyl dextran sensor surfaces by analysis of the specific activity of monoclonal antibodies", J. Mol. Recognit., (1995); 8:125-131.
Jönsson, U. et al., "Real-time biospecific interaction analysis using surface plasmon resonance and a sensor chip technology", Biotechniques (1991); 11:620-627.
Jönsson, U. et al., "Intorducing a biosensor based technology for reat-time biospecific interaction analysis", Ann. Biol. Clin., (1993); 51:19-26.
Kanakaraj, P. et al., "Defective Interleukin (IL)-18 mediated natural killer and T helper cell type 1 responses in Il-1 receptor associated kinase (IRAK) deficient mice", J. Exp. Med., (1999); 189:1129-1138.
Kaufman, R. et al., "Amplification and expression of sequences cotransfected with a modular dihydrofolate reductase complementary DNA Gene", Mol. Biol., (1982); 159:601-621.
Kearney, et al., "A new mouse myeloma cell line that has lost immunoglobulin expression but permits the construction of antibody secreting hybrid cell lines", J. Immunol. (1979); 123:1548-1550.
Kellermann, S. et al., "Antibody discovery: the use of transfenic mice to generate human monoclonal antibodies for therapeutics", Current Opinion in Biotechnology, (2002); 13:593-597.
Kim, J.K. et al., "Maping the site on human IgG for binding of the MHC class I-related receptor, RcRn", Eur. J. Immunol., (1999); 29:2819-2825.
Konishi, K. et al., "A simple and sensitive bioassay for the detection of human interleukin-18/interferon-y-inducing factor using human myelomonocytic KG-1 cells", J. Immunol. Methods (1997); 209:187-191.
Kipriyanov, S.M. et al., "Recombinant single-chain Fv fragments carrying C-Terminal cysteine residues: production of bivalent and biotinylated miniantibodies", Mol. Immunol. (1994); 31:1047-1058.
Kipriyanov, S. et al., "Single-chain antibody streptavidin fusions: Tetrameric bifunctional scFv-complexes with biotin binding activity and enhanced affinity to antigen," Human Antibodies and Hybridomas, (1995); 6:93-101.
Leung, B. et al., "A role for IL-18 in neutrophil activation", J. Immunol., (2001); 167:2879-2886.
Little, M. et al., "Of mice and men: hybridoma and recombinant antibodies", Immunology Today, (2000); 21:364-370.
Lund, J. et al., "Human FcyRi and FcyRII interact with distinct but overlapping sites on human IgG1", J. Immunology, (1991); 147: 2657-2662.
McCafferty, J. et al., "Phage antibodies: filamentous phage displaying antidoby variable domains", Nature, (1990); 348:552-554.
McInnes, I. et. al., "Interleukin 18: a pleiotropic participant in chronic inflammation", Immunology Today, (2000); 21:312-315.
Mendez, M. et al., "Functional transplant of megabase human immunoglobulin loci recapitulates human antibody response in mice", Nature Genetics, (1997); 15:146-156.
Mizushima, S. et al., "pEF-BOS, a powerful mammalian expression vector", Nucleic acids Research, (1990); 18:5322.
Nakanishi, K. et al., "Interleukin-18 regulates both TH1 and TH2 responses", Ann. Rev. Immunol, (2001); 19:423-474.
Nakanishi K., et al., "Interleukin-18 is a unique cytokine that stimulates both Th1 and Th2 responses depending on its cytokine milieu", Cytokine and Growth Factor Rev., (2001); 12:53-72.
Netea, M. et al., "Neutralization of Il-18 reduces neutrophil tissue accumulation and protects mice against lethal *Escherichia coli*and *Salmonella typhimurium*endotoxemia", J. Immunol., (2000): 164:2644-2649.
Ober, R. et al., "Differences in promiscuity for antibody-FcRn interactions across species: implications for therapeutic antibodies", Int. Immunol., (2001); 13:1551-1559.
Poljak, R. et al., "Production and structure of diabodies", Structure, (1994); 2:1121-1123.
Sims, John E., "IL-1 and IL-18 receptors, and their extended family", Current Opin Immunol., (2002); 14:117-122.
Sugawara, S. et al., "Neutrophil proteinase 3-mediated induction of bioactive IL-18 secretion by human oral epithelial cells", J. Immunol., (2001); 167:6568-6575.

Takeda, K., et al., "Defective NK cell activity and TH1 response in Il-18- deficient mice", Immunity, (1998); 8:383-390.

Taylor, L. et al., "A transgenic mouse that expresses a diversity of human sequence heavy and light chain immunoglobulins", Nucl. Acids Res., (1992); 20:6287-6295.

Tissi, L., et al., "Role of tumor necrosis factor alpha, Interleukin-1B, and interleukin-6 in a mouse model of group B streptococcal arthritis", Infect. Immunol., (1999); 67:4545-4550.

Trentham, D. et al., "Autoimmunity to type II collagen: an experimental model of arthritis", J. Exp. Med., (1997); 146:857-868.

Tsutsui, H. et al., "Caspase-1-independent, Fas/Fas ligand-mediated Il-18 secretion from Macrophages", Immunity, (1999); 11:359-367.

Urlaub, G. et al., "Isolation of chinese hamster ceU mutants deficient in dihydrofolate reductase activity", Proc. Natl. Acad. Sci. USA, (1980) 77:4216-4220.

Ushio, S., et al., "Cloning of the cDNA for human IFn-y-Inducing factor, expression in *Escherichia coli*, and studies on the biologic activities of the protein", J. Immunol., (1996); 156:4274-4279.

Ward, E. et al., "Bidning activities of a repertoire of single immunoglobulin variabe domains secreted from *Escherichia coli*", Nature, (1989); 341:544-546.

Wei, X.Q., et al., "Reduced Incidence and severity of collagen-induced arthritis in mice lacking IL-18[1]", J. Immunol., (2001); 166:517-521.

Giege, Richard et al., Crystallization of Nucleic Acids and Proteins, A Practical Approach, 2nd Edition (1999), pp. 1-16.

Junghans, R.P. et al., Anti-Tac-H, a Humanized Antibody to the Interleukin 2 Receptor with New Features for Immunotherapy in Malignant and Immune Disorders, Cancer Research, (1990) vol. 50, pp. 1495-1502.

Kettleborough, Catherine A. et al., Humanization of a mouse monoclonal antibody by CDR-grafting: the importance of framework residues on loop conformation, Protein Engineering, (1991) vol. 4(7), pp. 773-783.

Panka, D. J. et al., Variable region framwork differences result in decreased or increased affinity of variant anti-digxin antibodies, PNAS, (1988) vol. 85, pp. 3080-3084.

Van Nostrand, W. et al., Protease nexin-II, a potent anti-chymotrypsin, shows identity to amyloid B-Protein precursor, Nature (1989) vol. 341, pp. 546-549.

Zhong, R.K. et al., Cytotoxicity of Anit-CD64-Ricin A Chain Immunotoxin Against Human Acute Myeloid Leukemia Cells In Vitro and in SCID Mice, Hematother. Stem Cell Res. (2001) vol. 10(1), pp. 95-105.

* cited by examiner

IL-18 BINDING PROTEINS

CROSS-REFERENCE TO RELATED APPLICATION

This application claims the benefit of priority to U.S. provisional application No. 60/519,474, filed Nov. 12, 2003.

FIELD OF THE INVENTION

The present invention relates interleukin 18 (IL-18) binding proteins, and specifically to their uses in the prevention and/or treatment of acute and chronic inflammatory diseases.

BACKGROUND OF THE INVENTION

Interleukin-18 (IL-18) was originally described in 1989 as interferon-gamma inducing factor (IGIF) and is a pro-inflammatory cytokine with various functions in addition to an ability to induce interferon gamma. These biological properties include activation of NF-κb, Fas ligand expression, the induction of both CC and CXC chemokines, and increased production of competent human immunodeficiency virus. Due to the ability of IL-18 to induce interferon gamma production in T cells and macrophages, it plays an important role in Th1-type immune responses and participates in both innate and acquired immunity. IL-18 is related to the IL-1 family in terms of both structure and function. For reviews of IL-18 structure, function and biological activity, see for example Dinarello, C. et al. (1998) *J. Leukoc. Biol.* 63:658-654; Dinarello, C. A. (1999) *Methods* 19:121-132; and Dinarello, C. A. (1999) *J. Allergy Clin. Immunol.* 103:11-24; (McInnes, I. B. et. al. (2000) *Immunology Today* 21:312-315; Nakanishi, K. et al (2001) *Ann. Rev. Immunol* 19:423-474.

Intracellular pro-IL-18 is proteolytically processed to an 18 kDa active form in endotoxin-stimulated cells by caspase 1 (Ghayur, T. et al., (1997) *Nature* 386:619-623; Gu, Y. et al., (1997) *Science* 275:206-209) and in Fas-L or bacterial DNA stimulated cells by caspases 4, 5 and 6 (Tsutsui, H. et al., (1999) *Immunity* 11:359-67; Ghayur, T., *Unpublished Observations*). Pro-IL-18 is also proteolytically processed by other proteases such as neutrophil proteinase 3 (Sugawara, S. et al., (2001) *J. Immunol.*, 167, 6568-6575), caspase 3 (Akita, K. et al., (1997) *J. Biol. Chem.* 272, 26595-26603), and serine proteases elastase and cathepsin (Gracie J. A., et al., (2003) *Journal of Leukocyte Biology* 73, 213-224). Both human and murine IL-18 lack a classical leader sequence and the mechanism of mature IL-18 release by cells is not well understood.

The biological activities of IL-18 are mediated through IL-18 binding to a heterodimeric IL-18 receptor (IL-18R) that consists of two subunits: the α-subunit (a member of the IL-1R family, also termed IL-1R-related protein-1 or IL-1Rrp1) and the β-subunit (also termed IL-18R accessory protein, IL-18AP or AcPL). The IL-18Rα subunit binds IL-18 directly, but is incapable of signal transduction. The β-subunit does not bind IL-18 by itself, but in conjunction with the α-subunit forms the high affinity receptor ($K_D$=~0.3 nM) that is required for signal transduction (Sims, J. E., (2002) *Current Opin Immunol.* 14:117-122). IL-18 signal transduction via the IL-18Rαβ complex is similar to the IL-1R and Toll like receptor (TLR) systems. IL-18R signaling uses the signal transduction molecules, such as MyD88, IRAK, TRAF6 and results in similar responses (e.g. activation of NIK, IkB kinases, NF-kB, JNK and p38 MAP kinase) as does IL-1. Requirement for IL-18Rα and signal transduction molecules in mediating IL-18 bioactivity has been confirmed using IL-18Rα subunit (Hoshino K., et al (1999) *J. Immunol.* 162:5041-5044;), MyD88 (Adachi O., et al. (1998) *Immunity* 9:143-150) or IRAK (Kanakaraj P., (1999) *J. Exp. Med.* 189:1129-1138) knockouts respectively.

Antibodies that bind IL-18 are known in the art. Mouse antibodies capable of neutralizing IL-18 are disclosed in EP 0 974 600. Human antibodies to IL-18 have been disclosed in PCT publication WO 0158956 and incorporated herein by reference. The present invention provides a novel family of binding proteins, human antibodies, and fragments thereof, capable binding IL-18, binding with high affinity, and binding and neutralizing IL-18.

SUMMARY OF THE INVENTION

This invention pertains to IL-18 binding proteins, particularly antibodies to human IL-18, as well as methods of making and using such binding proteins. One aspect of the invention pertains to a method of regulating gene expression using a modulator of IL-18.

One aspect of this invention pertains to a binding protein comprising an antigen binding domain capable of binding human IL-18. In one embodiment the antigen binding domain comprises at least one CDR comprising an amino acid sequence selected from the group consisting of:

CDR-H1. $X_1$-$X_2$-$X_3$-$X_4$-$X_5$-$X_6$-$X_7$ (SEQ ID NO: 42), wherein;
$X_1$ is S, N, H, R, or Y;
$X_2$ is Y, G, R, S, or C;
$X_3$ is W, G, Y, D, S, V, or I;
$X_4$ is I, H, W, Y, M, L, or D;
$X_5$ is G, Y, S, N, or H;
$X_6$ is W, or is not present; and
$X_7$ is T, S, G, or is not present;

CDR-H2. $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$ (SEQ ID NO: 43), wherein;
$X_1$ is F, Y, H, S, or V;
$X_2$ is I, or F;
$X_3$ is Y, S, or W;
$X_4$ is P, Y, or S;
$X_5$ is G, S, R, or D;
$X_6$ is D, or G;
$X_7$ is S, T, G, or R;
$X_8$ is E, T, I, or N;
$X_9$ is T, Y, N, I, K, or H;
$X_{10}$ is R, Y, or S;
$X_{11}$ is Y, N, or S;
$X_{12}$ is S, P, A, or V;
$X_{13}$ is P, S, or D;
$X_{14}$ is T, L, or S;
$X_{15}$ is F, K, or V;
$X_{16}$ is Q, S, or K; and
$X_{17}$ is G, or is not present;

CDR-H3. $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$ (SEQ ID NO: 44), wherein;
$X_1$ is V, D, E, S, or C;
$X_2$ is G, R, D, S, K, L, Y, or A;
$X_3$ is S, G, Y, or R;
$X_4$ is G, S, Y, N, T, or D;
$X_5$ is W, S, A, G, Y, or T;
$X_6$ is Y, G, S, F, W, or N;
$X_7$ is P, S, F, Y, V, G, W, or V;
$X_8$ is Y, F, D, P, M, I, or N;
$X_9$ is T, W, D, L, Y, E, P, F, or G;
$X_{10}$ is F, D, Y, H, V, Y, or is not present;
$X_{11}$ is D, Y, F, L, or is not present;
$X_{12}$ is I, D, Y, or is not present;
$X_{13}$ is Y, or is not present;

$X_{14}$ is Y, or is not present;
$X_{15}$ is G, or is not present;
$X_{16}$ is M, or is not present;
$X_{17}$ is D, or is not present; and
$X_{18}$ is V, or is not present;

CDR-L1. $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$ (SEQ ID NO: 45), wherein;
$X_1$ is R, or K;
$X_2$ is A, G, or S;
$X_3$ is S;
$X_4$ is E, R, Q, or H;
$X_5$ is S, I, T, or N;
$X_6$ is I, V, L, or F;
$X_7$ is S, G, L, N, or R;
$X_8$ is S, G, Y, R, N, H, or D;
$X_9$ is N, G, Y, R, or S;
$X_{10}$ is L, Y, S, or D;
$X_{11}$ is A, L, N, V, G, or D;
$X_{12}$ is A, N, E, K, G, or is not present;
$X_{13}$ is K, T, N, or is not present;
$X_{14}$ is N, Y, T, or is not present;
$X_{15}$ is Y, L, or is not present;
$X_{16}$ is L, C, Y, or is not present; and
$X_{17}$ is A, D, or is not present;

CDR-L2. $X_1$-$X_2$-$X_3$-$X_4$-$X_5$-$X_6$-$X_7$ (SEQ ID NO: 46), wherein;
$X_1$ is T, G, S, W, or E;
$X_2$ is A, V, T, I, or L;
$X_3$ is S, or F;
$X_4$ is T, I, N, S, R, or Y;
$X_5$ is R, or L;
$X_6$ is A, Q, E, or F; and
$X_7$ is T, or S;
and CDR-L3. $X_1$-$X_2$-$X_3$-$X_4$-$X_5$-$X_6$-$X_7$-$X_8$-$X_9$-$X_{10}$ (SEQ ID NO: 47), wherein;
$X_1$ is Q, or M;
$X_2$ is Q, H, or Y;
$X_3$ is Y, N, G, S, or R;
$X_4$ is N, H, Y, D, G, V, L, or I;
$X_5$ is N, G, I, Y, S, Q, F, or E;
$X_6$ is W, S, T, L, I, or F;
$X_7$ is P, L, T, D, or I;
$X_8$ is S, L, P, C, W, I, or F;
$X_9$ is I, T, S, or is not present; and
$X_{10}$ is T, or is not present.

Preferably, the antigen binding domain comprises at least one CDR comprising an amino acid sequence selected from the group consisting of Residues 31-35 of SEQ ID NO.:6; Residues 50-66 of SEQ ID NO.:6; Residues 99-110 of SEQ ID NO.:6; Residues 24-34 of SEQ ID NO.:7; Residues 50-56 of SEQ ID NO.:7; Residues 89-98 of SEQ ID NO.:7; Residues 31-37 of SEQ ID NO.:8; Residues 52-67 of SEQ ID NO.:8; Residues 100-110 of SEQ ID NO.:8; Residues 24-35 of SEQ ID NO.:9; Residues 21-27 of SEQ ID NO.:9; Residues 90-98 of SEQ ID NO.:9; Residues 31-35 of SEQ ID NO.:10; Residues 50-65 of SEQ ID NO.:10; Residues 98-107 of SEQ ID NO.:10; Residues 24-34 of SEQ ID NO.:11; Residues 50-56 of SEQ ID NO.:11; Residues 89-97 of SEQ ID NO.:11; Residues 31-37 of SEQ ID NO.:12; Residues 52-67 of SEQ ID NO.:12; Residues 100-108 of SEQ ID NO.:12; Residues 24-35 of SEQ ID NO.:13; Residues 51-57 of SEQ ID NO.:13; Residues 90-98 of SEQ ID NO.:13; Residues 31-35 of SEQ ID NO.:14; Residues 50-66 of SEQ ID NO.:14; Residues 99-111 of SEQ ID NO.:14; Residues 24-40 of SEQ ID NO.:15; Residues 56-62 of SEQ ID NO.:15; Residues 95-103 of SEQ ID NO.:15; Residues 31-37 of SEQ ID NO.:16;. Residues 52-67 of SEQ ID NO.:16; Residues 100-109 of SEQ ID NO.:16; Residues 24-35 of SEQ ID NO.:17; Residues 51-57 of SEQ ID NO.:17; Residues 90-98 of SEQ ID NO.:17; Residues 31-35 of SEQ ID NO.:18; Residues 20-36 of SEQ ID NO.:18; Residues 99-108 of SEQ ID NO.:18; Residues 24-34 of SEQ ID NO.:19; Residues 50-56 of SEQ ID NO.:19; Residues 89-97 of SEQ ID NO.:19; Residues 31-35 of SEQ ID NO.:20; Residues 52-67 of SEQ ID NO.:20; Residues 100-108 of SEQ ID NO.:20; Residues 24-35 of SEQ ID NO.:21; Residues 51-57 of SEQ ID NO.:21; Residues 90-98 of SEQ ID NO.:21; Residues 31-35 of SEQ ID NO.:22; Residues 50-66 of SEQ ID NO.:22; Residues 99-116 of SEQ ID NO.:22; Residues 24-39 of SEQ ID NO.:23; Residues 55-61 of SEQ ID NO.:23; Residues 94-102 of SEQ ID NO.:23; Residues 31-37 of SEQ ID NO.:24; Residues 52-67 of SEQ ID NO.:24; Residues 100-109 of SEQ ID NO.:24; Residues 24-35 of SEQ ID NO.:25; Residues 51-57 of SEQ ID NO.:25; Residues 90-98 of SEQ ID NO.:25; Residues 31-37 of SEQ ID NO.:26; Residues 52-67 of SEQ ID NO.:26; Residues 100-109 of SEQ ID NO.:26; Residues 24-35 of SEQ ID NO.:27; Residues 51-57 of SEQ ID NO.:27; Residues 90-98 of SEQ ID NO.:27; Residues 31-37 of SEQ ID NO.:28; Residues 52-67 of SEQ ID NO.:28; Residues 100-108 of SEQ ID NO.:28; Residues 24-35 of SEQ ID NO.:29; Residues 51-57 of SEQ ID NO.:29; Residues 90-98 of SEQ ID NO.:29; Residues 31-37 of SEQ ID NO.:30; Residues 52-67 of SEQ ID NO.:30; Residues 99-109 of SEQ ID NO.:30; Residues 24-35 of SEQ ID NO.:31; Residues 51-57 of SEQ ID NO.:31; Residues 90-98 of SEQ ID NO.:31; Residues 31-37 of SEQ ID NO.:32; Residues 52-67 of SEQ ID NO.:32; Residues 100-109 of SEQ ID NO.:32; Residues 24-35 of SEQ ID NO.:33; Residues 51-57 of SEQ ID NO.:33; Residues 90-98 of SEQ ID NO.:33; Residues 31-37 of SEQ ID NO.:34; Residues 52-67 of SEQ ID NO.:34; Residues 100-108 of SEQ ID NO.:34; Residues 24-35 of SEQ ID NO.:35; Residues 51-57 of SEQ ID NO.:35; Residues 90-98 of SEQ ID NO.:35; Residues 31-35 of SEQ ID NO.:36; Residues 50-66 of SEQ ID NO.:36; Residues 99-116 of SEQ ID NO.:36; Residues 24-39 of SEQ ID NO.:37; Residues 55-61 of SEQ ID NO.:37; Residues 94-102 of SEQ ID NO.:37; Residues 31-35 of SEQ ID NO.:38; Residues 50-66 of SEQ ID NO.:38; Residues 99-108 of SEQ ID NO.:38; Residues 24-35 of SEQ ID NO.:39; Residues 51-57 of SEQ ID NO.:39; Residues 90-98 of SEQ ID NO.:39; Residues 31-37 of SEQ ID NO.:40; Residues 52-67 of SEQ ID NO.:40; Residues 97-109 of SEQ ID NO.:40; Residues 24-40 of SEQ ID NO.:41; Residues 56-62 of SEQ ID NO.:41; Residues 95-103 of SEQ ID NO.:41. Preferably the binding protein comprises at least 3 CDRs.

In another preferred embodiment the binding protein comprises a $V_H$ domain. Preferably the $V_H$ domain comprises an amino acid sequence selected from the group consisting of SEQ ID NO: 6; SEQ ID NO: 8; SEQ ID NO:10; SEQ ID NO:12; SEQ ID NO:14; SEQ ID NO:16; SEQ ID NO:18; SEQ ID NO: 20; SEQ ID NO: 22; SEQ ID NO: 24; SEQ ID NO: 26; SEQ ID NO: 28; SEQ ID NO: 30; SEQ ID NO: 32; SEQ ID NO: 34; SEQ ID NO: 36; SEQ ID NO: 38; and SEQ ID NO: 40. In another embodiment the binding protein comprises a $V_L$ domain. Preferably the $V_L$ domain comprises an amino acid sequence selected from the group consisting of SEQ ID NO: 7; SEQ ID NO: 9; SEQ ID NO: 11; SEQ ID NO: 13; SEQ ID NO: 15; SEQ ID NO: 17; SEQ ID NO: 19; SEQ ID NO: 21; SEQ ID NO: 23; SEQ ID NO: 25; SEQ ID NO: 27; SEQ ID NO: 29; SEQ ID NO: 31; SEQ ID NO: 33; SEQ ID NO: 35; SEQ ID NO: 37; SEQ ID NO: 39; and SEQ ID NO: 41.

In a preferred embodiment the binding protein comprises a $V_H$ and a $V_L$ domain. More preferably the binding protein comprises a $V_H$ domain comprising an amino acid sequence selected from the group consisting of SEQ ID NO: 6; SEQ ID NO: 8; SEQ ID NO: 10; SEQ ID NO: 12; SEQ ID NO: 14; SEQ ID NO: 16; SEQ ID NO: 18; SEQ ID NO: 20; SEQ ID NO: 22; SEQ ID NO: 24; SEQ ID NO: 26; SEQ ID NO: 28; SEQ ID NO: 30; SEQ ID NO: 32; SEQ ID NO: 34; SEQ ID NO: 36; SEQ ID NO: 38; and SEQ ID NO: 40 and a $V_L$ domain comprising an amino acid sequence selected from the group consisting of SEQ ID NO: 7; SEQ ID NO: 9; SEQ ID NO: 11; SEQ ID NO: 13; SEQ ID NO: 15; SEQ ID NO: 17; SEQ ID NO: 19; SEQ ID NO: 21; SEQ ID NO: 23; SEQ ID NO: 25; SEQ ID NO: 27; SEQ ID NO: 29; SEQ ID NO: 31; SEQ ID NO: 33; SEQ ID NO: 35; SEQ ID NO: 37; SEQ ID NO: 39; and SEQ ID NO: 41. Most preferably the binding protein comprises a $V_L$ domain comprising an amino acid sequence of SEQ ID NO: 7, and a $V_H$ domain comprising an amino acid sequence of SEQ ID NO: 6.

In another embodiment the binding protein further comprises a heavy chain immunoglobulin constant domain selected from the group consisting of a human IgM constant domain; a human IgG1 constant domain; a human IgG2 constant domain; a human IgG3 constant domain; a human IgG4 constant domain; a human IgE constant domain and a human IgA constant domain. Preferably the heavy chain immunoglobulin constant region domain is a human IgG1 constant domain. Preferably at least one amino acid residue is replaced in the heavy chain constant region domain such that effector functions of the antibody are altered. More preferably the human IgG1 constant domain comprises amino acid sequence selected from the group consisting of SEQ ID NO.: 2, and SEQ ID NO.:3.

In another embodiment the binding protein further comprises a light chain immunoglobulin constant domain selected from the group consisting of a human Ig kappa constant domain; and a human Ig lambda constant domain. Preferably the human Ig kappa constant domain comprises amino acid sequence SEQ ID NO.:4 and the human Ig lambda constant domain comprises amino acid sequence SEQ ID NO.:5.

In another embodiment the binding protein comprises an Ig constant heavy region having an amino acid sequence selected from the group consisting of: SEQ ID NO:2, and SEQ ID NO: 3; an IG constant light region having an amino acid sequence selected from the group consisting of: SEQ ID NO:4, and SEQ ID NO: 5; an Ig variable heavy region having an amino acid sequence of SEQ ID NO:6; and an Ig variable light region having an amino acid sequence of SEQ ID NO:7

In another embodiment the binding protein comprises an Ig constant heavy region having an amino acid sequence of SEQ ID NO: 3; an IG constant light region having an amino acid sequence of SEQ ID NO:4; an Ig variable heavy region having an amino acid sequence of SEQ ID NO:6; and an Ig variable light region having an amino acid sequence of SEQ ID NO:7.

In another embodiment the binding is selected from the group consisting of an immunoglobulin molecule or functional variants thereof known in the art, which variants retain the characteristic binding property of the binding protein. Examples of specific immunoglobulin embodiments include but are not limited to an scFv; a monoclonal antibody; a human antibody; a chimeric antibody; a humanized antibody; a single domain antibody; a Fab fragment; an Fab' fragment; an F(ab')2; an Fv; a disulfide linked Fv, and a bispecific or dual specific antibody. Most preferably the binding protein is a human antibody.

Another aspect of the invention provides a neutralizing binding protein comprising any one of the binding proteins disclosed above wherein the neutralizing binding protein is capable of neutralizing IL-18. Preferably the neutralizing binding protein is capable of neutralizing any one of pro-human IL-18; mature-human IL-18 or truncated-human IL-18. In another embodiment the neutralizing binding protein diminishes the ability of IL-18 to bind to its receptor. Preferably the neutralizing binding protein diminishes the ability of pro-human IL-18; mature-human IL-18 or truncated-human IL-18 to bind to its receptor.

In another embodiment the neutralizing binding protein is capable of inhibiting one or more of IL-18 biological activities selected from the group consisting of, Th1 modulation; Th2 modulation (Nakanishi K., et al (2001) Cytokine and Growth Factor Rev. 12:53-72); Nk modulation; neutrophil modulation; monocyte-macrophage lineage modulation; neutrophil modulation; eosinophil modulation; B-cells modulation; cytokine modulation; chemokine modulation; adhesion molecule modulation; and cell recruitment modulation.

In a preferred embodiment the neutralizing binding protein has a dissociation constant ($K_D$) selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M.

In another embodiment the neutralizing binding protein has an on rate selected from the group consisting of: at least about $10^2$ $M^{-1}$ $s^{-1}$; at least about $10^3$ $M^{-1}$ $s^{-1}$; at least about $10^4$ $M^{-1}$ $s^{-1}$; at least about $10^5$ $M^{-1}$ $s^{-1}$; and at least about $10^6$ $M^{-1}$ $s^{-1}$.

In yet another embodiment the neutralizing binding protein has an off rate selected from the group consisting of: at most about $10^{-3}$ $s^{-1}$; at most about $10^{-4}$ $s^{-1}$; at most about $10^{-5}$ $s^{-1}$; and at most about $10^{-6}$ $s^{-1}$.

Another aspect of the invention provides a labeled binding protein comprising any one of the binding proteins disclosed above wherein the binding protein is conjugated to a detectable label. Preferably the detectable label is selected from the group consisting of a radiolabel, an enzyme, a fluorescent label, a luminescent label, a bioluminescent label, a magnetic label and biotin. More preferably the radiolabel is $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

Another aspect of the invention provides a conjugate protein comprising any one of the binding proteins disclosed above wherein said binding protein is conjugated to a therapeutic or cytotoxic agent. Preferably the therapeutic or cytotoxic agent is selected from the group consisting of an anti-metabolite; an alkylating agent; an antibiotic; a growth factor; a cytokine; an anti-angiogenic agent; an anti-mitotic agent; an anthracycline; toxin; and an apoptotic agent.

One embodiment pertains to an isolated nucleic acid encoding any one of the binding proteins disclosed above. A further embodiment provides a vector comprising the isolated nucleic acid disclosed above wherein said vector is selected from the group consisting of pcDNA; pTT (Durocher et al., *Nucleic Acids Research* 2002, Vol 30, No. 2); pTT3 (pTT with additional multiple cloning site; pEFBOS (Mizushima, S. and Nagata, S., (1990) *Nucleic acids Research* Vol 18, No. 17); pBV; pJV; and pBJ.

In another embodiment a host cell is transformed with the vector. Preferably the host cell is a prokaryotic cell. More preferably the host cell is *E. Coli*. In a related embodiment the host cell is an eukaryotic cell. Preferably the eukaryotic cell is selected from the group consisting of protist cell, animal cell, plant cell and fungal cell. More preferably the host cell is a mammalian cell including, but not limited to, CHO and COS; or a fungal cell such as *Saccharomyces cerevisiae*; or an insect cell such as Sf9.

Another aspect of the invention provides a method of producing a binding protein that binds human IL-18, comprising culturing any one of the host cells disclosed above in a culture medium under conditions sufficient to produce a binding protein that binds human IL-18. Another embodiment provides a binding protein produced according to the method disclosed above.

Another aspect of the invention provides a crystallized binding protein comprising any one of the binding proteins disclosed above, wherein the binding protein exists as a crystal. Preferably the crystal is a carrier-free pharmaceutical controlled release crystal. In one embodiment the binding protein that exists as a crystal has a greater half-life in vivo than the soluble counterpart of the binding protein. In another embodiment the binding protein retains its biological activity after crystallization.

One embodiment provides a composition for the release of a binding protein wherein the composition comprises a formulation which in turn comprises a crystallized binding protein as disclosed above and an ingredient; and at least one polymeric carrier. Preferably the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl) methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polyeaccharides, blends and copolymers thereof. Preferably the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed above.

Another aspect of the invention provides a method for regulating gene expression of a gene of interest comprising the steps of providing an IL-18 polypeptide or an IL-18 modulator; and contacting the polypeptide or modulator to a cell wherein the gene of interest is selected from the group consisting of genes identified by Genbank Identification numbers:

| | | | | | | |
|---|---|---|---|---|---|---|
| NM_000389, | NM_002198, | NM_002163, | NM_006144, | NM_006515, | NM_007185, | NM_002288, |
| NM_003661, | NM_021958, | NM_001335, | Hs.382006, | NM_020125, | NM_007210, | NM_021798, |
| NM_013324, | M11313, | D88152, | NM_001103, | U37519, | NM_000697, | J03600, |
| NM_014578, | S66793, | U47054, | L19871, | M81181, | NM_001188, | U15460, |
| NM_014417, | Z23115, | NM_001713, | U45878, | U37546, | U72649, | U49187, |
| J03507, | U50360 | XM_071866, | NM_005623, | Z32765, | Z11697, | XM_071866, |
| U51096, | M83667, | D87469, | L07765, | U66468, | X14830, | L29217, |
| X15880, | NM_001851, | M27691, | M37435, | X13589, | X16866, | X59131, |
| NM_004393, | U73328, | L19267, | U53445, | X68277, | U48807, | NM_001950, |
| U87269, | M57730, | X52541, | J04076, | X63741, | L07077, | M62831, |
| M60830, | U53786, | NM_001988, | NM_000141, | M23668, | U60062, | NM_000141, |
| U49973, | U89995, | U27326, | A28102, | M25667, | L34357, | U19523, |
| L01406, | U03486, | X68285, | Z18859, | D49958, | D43772, | AC000099, |
| M57731, | X53800, | M91036, | D16583, | X64877, | X58431, | M16937, |
| NM_014468, | X92814, | L19314, | M26665, | D10995, | L41147, | M24283, |
| S81914, | J03171, | J00219, | NM_000619, | NM_000585, | U31628, | X04500, |
| M27492, | X01057, | M26062, | Y00081, | Y00787, | Z31695, | X06256, |
| X57206, | U20734, | NM_014879, | D31762, | D42038, | NM_005551, | NM_014846, |
| X06182, | NM_005551, | X07730, | M13955, | M57710, | S83362, | NM_002314, |
| NM_005569, | U49957, | U89922, | X14008, | U59914, | D14497, | X59727, |
| NM_000429, | U43944, | X72755, | NM_021230, | NM_005951, | X78710, | X70991, |
| M32011, | S77763, | M58603, | S76638, | M69043, | U91616, | D86425, |
| L13740, | U44848, | U79251, | M27288, | AF000234, | D50640, | L20971, |
| L10343, | U77735, | NM_003579, | U17034, | AB000584, | X63131, | D11428, |
| NM_032940, | NM_005035, | NM_003579, | M18255, | L01087, | D38128, | Y10375, |
| D15049, | M31166, | U59877, | NM_003579, | U64675, | S57153, | NM_002903, |
| NG_000013, | X75042, | M83221, | NM_000537, | U22314, | S59049, | U70426, |
| U22377, | U38480, | L10338, | M23178, | M69203, | NM_005409, | D79206, |
| NM_005065, | NM_004186, | J03764, | NM_006802, | D89077, | NM_003037, | M91463, |
| D82326, | L05568, | U96094, | X83301, | D21267, | L31529, | M62800, |
| NM_021014, | Z35093, | NM_005816, | L25444, | M95787, | NM_005421, | L47345, |
| M57732, | NM_003205, | M96956, | U19878, | M92357, | M59465, | X83490, |
| U37518, | NM_003294, | U19261, | U78798, | S69790, | U53476, | L15309, |
| U78722, | X57809, | U79249, | AB000464, | X77744, | U79248, | AI420129, |
| HG2981-HT3127, | | HG3548-HT3749, | | HG870-HT870, | | HG4333-HT4603, |
| HG3111-HT3287, | | HG4593-HT4998, | | HG961-HT961, | | HG1877-HT1917, |
| HG3115-HT3291, | | HG4115-HT4385, | | and HG3925-HT4195. | | |

Preferably the modulator is an antagonist. More preferably the modulator is a binding protein or a neutralizing binding protein.

The invention also provides a pharmaceutical composition comprising a binding protein or a neutralizing binding protein as disclosed above and a pharmaceutically acceptable carrier. In a further embodiment the pharmaceutical composition comprises at least one additional therapeutic agent for treating a disorder in which IL-18 activity is detrimental. Preferably the additional agent is selected from the group consisting of: angiogenesis inhibitors (including but not limited to anti- VEGF antibodies or VEGF-trap); kinase inhibitors (including but not limited to KDR and TIE-2 inhibitors); co-stimulation molecule blockers (including but not limited to anti-B7.1, anti-B7.2, CTLA4-Ig, anti-CD20); adhesion molecule blockers (including but not limited to anti-LFA-1 Abs, anti-E/L selectin Abs, small molecule inhibitors); anti-cytokine antibody or functional fragment thereof (including but not limited to anti-IL-12, anti-TNF, anti-IL-6/cytokine receptor antibodies); methotrexate; corticosteroids; cyclosporin; rapamycin; FK506; and non-steroidal anti-inflammatory agents.

In another aspect, the invention provides a method for inhibiting human IL-18 activity comprising contacting human IL-18 with a binding protein disclosed above such that human IL-18 activity is inhibited. In a related aspect the invention provides a method for inhibiting human IL-18 activity in a human subject suffering from a disorder in which IL-18 activity is detrimental, comprising administering to the human subject a binding protein disclosed above such that human IL-18 activity in the human subject is inhibited and treatment is achieved. Preferably the disorder is selected from the group comprising rheumatoid arthritis, osteoarthritis, juvenile chronic arthritis, Lyme arthritis, psoriatic arthritis, reactive arthritis, and septic arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection (including but not limited to bone marrow and solid organ rejection), acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, *chlamydia, yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B *streptococci* (GBS) infection, mental disorders (e.g., depression and schizophrenia), Th2 Type and Th1 Type mediated diseases, and cancers such as lung, breast, stomach, bladder, colon, pancreas, ovarian, prostate and rectal cancer and hematopoietic malignancies (leukemia and lymphoma).

In another aspect the invention provides a method of treating a patient suffering from a disorder in which IL-18 is detrimental comprising the step of administering any one of the binding proteins disclosed above before, concurrent, or after the administration of a second agent, as discussed above.

Another aspect of the invention provides a neutralizing binding protein selected from the group consisting of a human antibody; a chimeric antibody; a humanized antibody and a CDR grafted antibody, wherein the neutralizing binding protein is capable of binding mature-human IL-18, but does not specifically bind pro-human IL-18.

Another aspect of the invention provides a neutralizing binding protein selected from the group consisting of a human antibody; a chimeric antibody; a humanized antibody and a CDR grafted antibody, wherein the neutralizing binding protein is capable of competing with 125-2H antibody for binding human IL-18.

Another aspect of the invention provides a neutralizing binding protein selected from the group consisting of a human antibody; a chimeric antibody; a humanized antibody and a CDR grafted antibody, wherein the neutralizing binding protein is not capable of competing with 125-2H antibody for binding human IL-18.

Another aspect of the invention provides a neutralizing binding protein selected from the group consisting of a human antibody; a chimeric antibody; a humanized antibody and a CDR grafted antibody, wherein the neutralizing binding protein is not capable of competing with a binding protein selected from the group consisting of 2.5(E)mg1 antibody and IL-18BP for binding human IL-18.

In a preferred embodiment the binding protein is capable of binding mature-human IL-18, but does not specifically bind pro-human IL-18. In yet another embodiment the binding protein is capable of competing with 125-2H antibody for binding human IL-18. In another embodiment the binding protein is not capable of competing with 125-2H antibody for binding human IL-18. In yet another embodiment the binding protein is not capable of competing a binding protein selected from the group consisting of 2.5(E)mg1 antibody, and IL-18BP for binding human IL-18.

In a preferred embodiment the binding protein comprises a $V_L$ domain comprising an amino acid sequence of SEQ ID NO: 9, and a $V_H$ domain comprising an amino acid sequence of SEQ ID NO: 8.

In another embodiment the binding protein comprises an Ig constant heavy region having an amino acid sequence selected from the group consisting of: SEQ ID NO:2, and SEQ ID NO: 3; an IG constant light region having an amino acid sequence selected from the group consisting of: SEQ ID NO:4, and SEQ ID NO: 5; an Ig variable heavy region having an amino acid sequence of SEQ ID NO:8; and an Ig variable light region having an amino acid sequence of SEQ ID NO:9.

In another embodiment the binding protein comprises an Ig constant heavy region having an amino acid sequence of SEQ ID NO: 3; an IG constant light region having an amino acid sequence of SEQ ID NO:4; an Ig variable heavy region having an amino acid sequence of SEQ ID NO:8; and an Ig variable light region having an amino acid sequence of SEQ ID NO:9.

DETAILED DESCRIPTION OF THE INVENTION

This invention pertains to IL-18 binding proteins, particularly anti-Il-18 antibodies, or antigen-binding portions thereof, that bind thereto. Various aspects of the invention relate to antibodies and antibody fragments, and pharmaceutical compositions thereof, as well as nucleic acids, recombinant expression vectors and host cells for making such antibodies and fragments. Methods of using the antibodies of the invention to detect human IL-18, to inhibit human IL-18 activity, either in vitro or in vivo, and to regulate gene expression are also encompassed by the invention. This invention also pertains to a truncated IL-18. In related aspects the invention also pertains to nucleic acids, recombinant expression vectors and host cells for making truncated IL-18.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "Polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The term "IL-18" as used herein, refers to the cytokine also known as interferon-gamma inducing factor (IGIF), that is a pro-inflammatory cytokine, that exhibits various functions in addition to an ability to induce interferon gamma. The term "human IL-18" used interchangeably with the term "hIL-18" encompasses polypeptide of SEQ ID NO: 1 and fragments thereof, including but not limited to, pro-human IL-18, mature human IL-18, and any truncated human IL-18 that retains a biological activity of IL-18 as described herein. The term "pro-human IL-18" as used herein, refers to a polypeptide of SEQ ID NO: 1. The term "mature human IL-18" as used herein, refers to residues 37-193 of SEQ ID NO: 1, and the term "truncated human IL-18 as used herein, refers to residues 59-193 of SEQ ID NO: 1. Preferably the IL-18, and fragments thereof, are biologically active. The term "recombinant human IL-18" or "rhIL-18" as used herein, refers to human IL-18 generated in vitro using recombinant DNA techniques.

"Biological activity of IL-18" as used herein, refers to all inherent biological properties of the cytokine IL-18. Biological properties of IL-18 include but are not limited to binding IL-18 receptor; promoting maturation and activation of Th1 and Tc1 cells; promoting production of cytokines such as TNF, IFNγ and IL-1β by several cell types; promoting macrophages to release cytokines such as TNF and IFNγ, produce NO; promoting FasL expression, cytotoxicity and cytokine release (IFNγ) from NK cells; promoting cytokine/chemokine release, respiratory burst, granule release, adhesion molecule expression in Neutrophils; promoting endothelial cells to migrate and thereby promote angiogenesis; promoting GAG release, MMP and NO production in Chondrocytes; promoting COX2 expression in some cells; and reducing cell proliferation in some cells.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or simply "antibody portion"), as used herein, refers to one or more fragments of an antibody that retain the ability to specifically bind to an antigen (e.g., hIL-18). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds hIL-18 is substantially free of antibodies that specifically bind antigens other than hIL-18). An isolated antibody that specifically binds hIL-18 may, however, have cross-reactivity to other antigens, such as IL-18 molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) *Current Opinion in Biotechnology* 13:593-597; Little M. et al (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of $V_H$ and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

As used herein, the term "hIL-18 neutralizing binding protein" refers to a protein that specifically binds hIL-18 and neutralizes a biological activity of hIL-18. Preferably a neutralizing binding protein is a neutralizing antibody whose binding to hIL-18 results in inhibition of a biological activity of hIL-18. Preferably the neutralizing binding protein binds hIL-18 and reduces a biologically activity of IL-18 by at least about 20%, 40%, 60%, 80%, 85% or more. This inhibition of a biological activity of hIL-18 by a neutralizing binding protein can be assessed by measuring one or more indicators of hIL-18 biological activity. These indicators of hIL-18 biological activity can be assessed by one or more of several standard in vitro or in vivo assays known in the art.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$K_{on}$", as used herein, is intended to refer to the on rate constant for association of an antibody to the antigen to form the antibody/antigen complex as is known in the art.

The term "$K_{off}$", as used herein, is intended to refer to the off rate constant for dissociation of an antibody from the antibody/antigen complex as is known in the art.

The term "$K_d$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "conjugate binding protein" refers to a binding protein chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The term "crystallized binding protein" as used herein, refers to a polypeptide that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of hIL-18). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of hIL-18). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, IL-18 polypeptides or polypeptides, nucleic acids, carbohydrates, or any other molecules that bind to hIL-18.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonist of interest include those that block or modulate the biological or immunological activity of hIL-18. Antagonists and inhibitors of hIL-18 may include, but are not limited to, proteins, nucleic acids, carbohydrates, or any other molecules which bind to hIL-18.

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

The term "competes" as used herein, and as generally known and used by practitioners skilled in the art, refers to the ability of one binding protein to interfere with, or otherwise hinder the binding of a second binding protein to a ligand common to both binding proteins (e.g., IL-18). Assays useful to determine competition characterisitics of binding proteins are well known in the art. Preferred competition assays are described herein.

I. Human Antibodies That Bind Human IL-18.

One aspect of the present invention provides isolated human antibodies, or antigen-binding portions thereof, that bind to IL-18 with high affinity, a low off rate and high neutralizing capacity. Preferably, the antibodies, or portions thereof, are isolated antibodies. Preferably, the human antibodies of the invention are neutralizing human anti-IL-18 antibodies.

A. Method of Making Anti IL-18 Antibodies

Antibodies of the present invention may be made by any of a number of techniques known in the art. A particularly preferred method for generating anti-IL-18 antibodies of the invention include using XENOMOUSE transgenic mice, and using hybridoma and SLAM cellular manipulation techniques (Abgenix, Inc., Fremont, Calif.) known in the art for preparing antibodies, and using antigens comprising the IL-18 peptide described in Example 3.2, i.e., human IL-18 comprising amino acid sequence of SEQ ID NO. 1 and fragments thereof.

In one embodiment of the instant invention, human antibodies are produced by immunizing a non-human animal comprising some, or all, of the human immunoglobulin locus with an IL-18 antigen. In a preferred embodiment, the non-human animal is a XENOMOUSE transgenic mouse, an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germline configuration YAC fragments of the human heavy chain loci and x light chain loci. See Mendez et al., *Nature Genetics* 15:146-156 (1997), Green and Jakobovits *J. Exp. Med.* 188:483-495 (1998), the disclosures of which are hereby incorporated by reference.

The invention also provides a method for making anti-IL-18 antibodies from non-human, non-mouse animals by immunizing non-human transgenic animals that comprise human immunoglobulin loci. One may produce such animals using the methods described immediately above. The methods disclosed in these patents may be modified as described in U.S. Pat. No. 5,994,619. In a preferred embodiment, the non-human animals may be rats, sheep, pigs, goats, cattle or horses.

In another embodiment, the non-human animal comprising human immunoglobulin gene loci are animals that have a "minilocus" of human immunoglobulins. In the minilocus approach, an exogenous Ig locus is mimicked through the inclusion of individual genes from the Ig locus. Thus, one or more $V_H$ genes, one or more DH genes, one or more JH genes, a mu constant region, and a second constant region (preferably a gamma constant region) are formed into a construct for insertion into an animal. This approach is described, inter alia, in U.S. Pat. Nos. 5,545,807, 5,545,806, 5,625,825, 5,625,126, 5,633,425, 5,661,016, 5,770,429, 5,789,650, 5,814,318, 5,591,669, 5,612,205, 5,721,367, 5,789,215, and 5,643,763, hereby incorporated by reference.

An advantage of the minilocus approach is the rapidity with which constructs including portions of the Ig locus can be generated and introduced into animals. However, a potential disadvantage of the minilocus approach is that there may not be sufficient immunoglobulin diversity to support full B-cell development, such that there may be lower antibody production.

In order to produce a human anti-IL-18 antibody, a non-human animal comprising some or all of the human immunoglobulin loci is immunized with an IL-18 antigen and the antibody or the antibody-producing cell is isolated from the animal. The IL-18 antigen may be isolated and/or purified IL-18 and is preferably a human IL-18. In another embodiment, the IL-18 antigen is a fragment of IL-18, preferably mature IL-18. In another embodiment, the IL-18 antigen is a fragment that comprises at least one epitope of IL-18.

Immunization of animals may be done by any method known in the art. See, e.g., Harlow and Lane, *Antibodies: A Laboratory Manual*, New York: Cold Spring Harbor Press, 1990. Methods for immunizing non-human animals such as mice, rats, sheep, goats, pigs, cattle and horses are well known in the art. See, e.g., Harlow and Lane and U.S. Pat. No. 5,994,619. In a preferred embodiment, the IL-18 antigen is administered with a adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

Example 2.2.A provides a protocol for immunizing a XENOMOUSE transgenic mouse with human IL-18 in phosphate-buffered saline.

B. Production of Antibodies and Antibody-Producing Cell Lines

After immunization of an animal with an IL-18 antigen, antibodies and/or antibody-producing cells may be obtained from the animal. An anti-IL-18 antibody-containing serum is obtained from the animal by bleeding or sacrificing the animal. The serum may be used as it is obtained from the animal, an immunoglobulin fraction may be obtained from the serum, or the anti-IL-18 antibodies may be purified from the serum. Serum or immunoglobulins obtained in this manner are polyclonal, thus having a heterogeneous array of properties.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using IL-18, or a portion thereof, or a cell expressing IL-18. In a preferred embodiment, the initial screening is performed using an enzyme-linked immunoassay (ELISA) or a radioimmunoassay (RIA), preferably an ELISA. An example of ELISA screening is provided in WO 00/37504, herein incorporated by reference.

Anti-IL-18 antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

Preferably, the immunized animal is a non-human animal that expresses human immunoglobulin genes and the splenic B cells are fused to a myeloma derived from the same species as the non-human animal. More preferably, the immunized animal is a XENOMOUSE transgenic mouse and the myeloma cell line is a non-secretory mouse myeloma, such as the myeloma cell line is P3X63Ag8.653 (see, e.g., Example 2.2.B).

In one aspect, the invention provides hybridomas that produce human anti-IL-18 antibodies. In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-IL-18 antibody.

In another aspect of the invention, recombinant antibodies are generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) *Proc. Natl. Acad. Sci. USA* 93:7843-7848. In this method, single cells secreting antibodies of interest, e.g., lymphocytes derived from any one of the immunized animals described in Section I (A), are screened using an antigen-specific hemolytic plaque assay, wherein the antigen IL-18, or a fragment thereof, is coupled to sheep red blood cells using a linker, such as biotin, and used to identify single cells that secrete antibodies with specificity for IL-18. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to IL-18. The amplified immunoglobulin sequences further can be manipulated in vitro, such as by in vitro affinity maturation methods such as those described in PCT Publication WO 97/29131 and PCT Publication WO 00/56772.

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131, the contents of each of which are incorporated herein by reference.

The recombinant antibody library may be from a subject immunized with IL-18, or a portion of IL-18. Alternatively, the recombinant antibody library may be from a naïve subject, i.e., one who has not been immunized with IL-18, such as a human antibody library from a human subject who has not been immunized with human IL-18. Antibodies of the invention are selected by screening the recombinant antibody library with the peptide comprising human IL-18 (e.g., a peptide corresponding to a portion of hIL-18) to thereby select those antibodies that recognize IL-18. Methods for conducting such screening and selection are well known in the art, such as described in the references in the preceding paragraph. To select antibodies of the invention having particular binding affinities for hIL-18, such as those that dissociate from human IL-18 with a particular $k_{off}$ rate constant, the art-known method of surface plasmon resonance can be used to select antibodies having the desired $k_{off}$ rate constant. To select antibodies of the invention having a particular neutralizing activity for hIL-18, such as those with a particular an $IC_{50}$, standard methods known in the art for assessing the inhibition of hIL-18 activity may be used.

In one aspect, the invention pertains to an isolated antibody, or an antigen-binding portion thereof, that binds human IL-18. Preferably, the antibody is a neutralizing antibody. Preferably, the antibody is a human antibody. In various embodiments, the antibody is a recombinant antibody or a monoclonal antibody. The most preferred neutralizing antibody of the invention is referred to herein as 2.5(E) and has VL with amino acid sequence of SEQ ID NO: 7 and VH with amino acid sequence of SEQ ID NO: 6. Most preferrably, the 2.5(E) antibody binds human IL-18 with a $K_d$ of less than $5 \times 10^{10}$ M (see Example 2.2.F).

Preferably, anti-IL-18 antibodies of the present invention, such as the 2.5(E) antibody and related antibodies, exhibit a capacity to reduce or to neutralize IL-18 activity, e.g., as assessed by any one of several in vitro and in vivo assays known in the art (e.g., see Example 3.2.F). For example, these antibodies neutralize IL-18-induced production of human interferon gamma in KG-1 cells with $IC_{50}$ values in the range of at least about $10^{-8}$ M, about $10^{-9}$ M, or about $10^{-10}$ M. Further these antibodies also neutralize IL-18-induced production of human interferon gamma in the whole blood cells with $IC_{50}$ values in the range of at least about $10^{-8}$ M, about $10^{-9}$ M, or about $10^{-10}$ M.

In a particularly preferred embodiment the anti-IL-18 antibody 2.5(E) binds to human IL-18 in various forms, including pro-IL-18, mature IL-18 and truncated IL-18. The antibody 2.5(E) does not specifically bind to other cytokines, such as IL-2, IL-3, IL-4, IL-5, IL-6, IL-7, IL-8, IL-9, IL-10, IL-11, IL-12, IL-13, IL-15, IL-16, IL-17, IL-21, TNF, LT (lymphotoxin), LTα1β2, and LTα2β1. However, the antibody 2.5(E) does exhibit cross reactivity to IL-18 from other species. For example, the antibody neutralizes the activity of IL-18 from cynomolgus monkey (IC50 for cyno IL-18=$9.1E \times 10^{-11}$; See Example 2.2.J1).

In one aspect, the invention pertains to 2.5(E) antibodies and functional antibody portions, 2.5(E) -related antibodies and functional antibody portions, and other human antibodies and functional antibody portions with equivalent properties to 2.5(E), such as high affinity binding to IL-18 with low dissociation kinetics and high neutralizing capacity. In preferred embodiments, the isolated antibody, or antigen-binding portion thereof, binds human IL-18, wherein the antibody, or antigen-binding portion thereof, dissociates from human IL-18 with a $k_{off}$ rate constant of about 0.1 s$^{-1}$ or less, as determined by surface plasmon resonance, or which inhibits human IL-18 activity with an $IC_{50}$ of about $1 \times 10^{-6}$ M or less. Alternatively, the antibody, or an antigen-binding portion thereof, may dissociate from human IL-18 with a $k_{off}$ rate constant of about $1 \times 10^{-2}$ s$^{-1}$ or less, as determined by surface plasmon resonance, or may inhibit human IL-18 activity with an $IC_{50}$ of about $1 \times 10^{-7}$ M or less. Alternatively, the antibody, or an antigen-binding portion thereof, may dissociate from human IL-18 with a $k_{off}$ rate constant of about $1 \times 10^{-3}$ s$^{-1}$ or less, as determined by surface plasmon resonance, or may inhibit human IL-18 activity with an $IC_{50}$ of about $1 \times 10^{-7}$ M or less. Alternatively, the antibody, or an antigen-binding portion thereof, may dissociate from human IL-18 with a $k_{off}$ rate constant of about $1 \times 10^{-4}$ s$^{-1}$ or less, as determined by surface plasmon resonance, or may inhibit human IL-18 activity with an $IC_{50}$ of about $1 \times 10^{-9}$ M or less. Alternatively, the antibody, or an antigen-binding portion thereof, may dissociate from human IL-18 with a $k_{off}$ rate constant of about $1 \times 10^{-5}$ s$^{-1}$ or less, as determined by surface plasmon resonance, or may inhibit human IL-18 activity with an $IC_{50}$ of about $1 \times 10^{-10}$ M or less. Alternatively, the antibody, or an antigen-binding portion thereof, may dissociate from human IL-18 with a $k_{off}$ rate constant of about $1 \times 10^{-5}$ s$^{-1}$ or less, as determined by surface plasmon resonance, or may inhibit human IL-18 activity with an $IC_{50}$ of about $1 \times 10^{-11}$ M or less.

In still another embodiment, the invention provides an isolated human antibody, or an antigen binding portion thereof, with a light chain variable region ($V_L$) comprising the amino acid sequence of SEQ ID NO: 7; SEQ ID NO: 9; SEQ ID NO: 11; SEQ ID NO: 13; SEQ ID NO: 15; SEQ ID NO: 17; SEQ ID NO: 19; SEQ ID NO: 21; SEQ ID NO: 23; SEQ ID NO: 25; SEQ ID NO: 27; SEQ ID NO: 29; SEQ ID NO: 31; SEQ ID NO: 33; SEQ ID NO: 35; SEQ ID NO: 37; SEQ ID NO: 39; or SEQ ID NO: 41, and a heavy chain variable region ($V_H$) comprising an amino acid sequence of SEQ ID NO: 6; SEQ ID NO: 8; SEQ ID NO: 10; SEQ ID NO: 12; SEQ ID NO: 14; SEQ ID NO: 16; SEQ ID NO: 18; SEQ ID NO: 20; SEQ ID NO: 22; SEQ ID NO: 24; SEQ ID NO: 26; SEQ ID NO: 28; SEQ ID NO: 30; SEQ ID NO: 32; SEQ ID NO: 34; SEQ ID NO: 36; SEQ ID NO: 38; or SEQ ID NO: 40.

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized binding protein. Preferably the invention relates to crystals of whole anti-IL-18 antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in WO 02072636, incorporated herein by reference. (Also see Example 2.2.M)

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S patent applications 20040018590 and 20020137134).

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

C. Production of Recombinant IL-18 Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody. Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Table 1 is a list of amino acid sequences of VH and VL regions of preferred anti-hIL-18 antibodies of the invention. In the VH region, the naturally occurring amino acid in position 1 of the amino terminus (N-terminus) is either Glutamate (E) or Glutamine (Q). However, to generate recombinant protein with homogeneous N-termini during large-scale production of protein comprising VH region, Glutamate (E) is preferred in position 1 of the N-terminus.

TABLE 1

List of Amino Acid Sequences of VH and VL regions

| Protein<br>Protein region | Sequence Identifier | Sequence<br>12345678901234567890 |
|---|---|---|
| VH 2.5(E) | SEQ ID NO.: 6 | EVQLVQSGTEVKKPGESLKI<br>SCKGSGYTVTSYWIGWVRQM<br>PGKGLEWMGFIYPGDSETRY<br>SPTFQGQVTISADKSFNTAF<br>LQWSSLKASDTAMYYCARVG<br>SGWYPYTFDIWGQGTMVTVS<br>S |
| VH 2.5 CDR-H1 | Residues 31-35 of SEQ ID NO.: 6 | SYWIG |
| VH 2.5 CDR-H2 | Residues 50-66 of SEQ ID NO.: 6 | FIYPGDSETRYSPTFQG |
| VH 2.5 CDR-H3 | Residues 99-110 of SEQ ID NO.: 6 | VGSGWYPYTFDI |
| VL 2.5(E) | SEQ ID NO.: 7 | EIVMTQSPATLSVSPGERAT<br>LSCRASESISSNLAWYQQKP<br>GQAPRLFIYTASTRATDIPA<br>RFSGSGSGTEFTLTISSLQS<br>EDFAVYYCQQYNNWPSITFG<br>QGTRLEIKR |
| VL 2.5 CDR-L1 | Residues 24-34 of SEQ ID NO.: 7 | RASESISSNLA |
| VL 2.5 CDR-L2 | Residues 50-56 of SEQ ID NO.: 7 | TASTRAT |
| VL 2.5 CDR-L3 | Residues 89-98 of SEQ ID NO.: 7 | QQYNNWPSIT |
| VH 2.13 | SEQ ID NO.: 8 | QVQLQESGPGLVTPSQTLSL<br>TCTVSGGSISSGGHYWTWIR<br>QHPGKGLEWIGYIYYSGSTY<br>YNPSLKSRLTISVDTSKNQF<br>SLKLSSVAAADTAVYYCARD<br>RGGSGSYWDYWGQGTLVTVS<br>S |
| VH 2.13 CDR-H1 | Residues 31-37 of SEQ ID NO.: 8 | SGGHYWT |
| VH 2.13 CDR-H2 | Residues 52-67 of SEQ ID NO.: 8 | YIYYSGSTYYNPSLKS |
| VH 2.13 CDR-H3 | Residues 100-110 of SEQ ID NO.: 8 | DRGGSGSYWDY |
| VL 2.13 | SEQ ID NO.: 9 | EIVLTQSPGTLSLSPGERAT<br>LSCRGSRSVSSGYLAWYQQK<br>PGQAPRLLIYGVSIRATGIP<br>DRFSGSGSGTDFTLTISRLE<br>PEDFAVYYCQQYHGSPLTFG<br>GGTKVEIKR |

TABLE 1-continued

List of Amino Acid Sequences of VH and VL regions

| Protein Protein region | Sequence Identifier | Sequence 12345678901234567890 |
|---|---|---|
| VL 2.13 CDR-L1 | Residues 24-35 of SEQ ID NO.: 9 | RGSRSVSSGYLA |
| VL 2.13 CDR-L2 | Residues 21-27 of SEQ ID NO.: 9 | GVSIRAT |
| VL 2.13 CDR-L3 | Residues 90-98 of SEQ ID NO.: 9 | QQYHGSPLT |
| VH 2.3 | SEQ ID NO.: 10 | QVQLQESGPGLVKPSETLSL TCTVSGGSIRNYYWSWIRQP PGKGLEWVGYIYSSGSTNYN PSLKSRVTISVDTSKNQFSL KLSSVTAADTAVYYCARDRG GASFFDYWGQGTLVTVSS |
| VH 2.3 CDR-H1 | Residues 31-35 of SEQ ID NO.: 10 | NYYWS |
| VH 2.3 CDR-H2 | Residues 50-65 of SEQ ID NO.: 10 | YIYSSGSTNYNPSLKS |
| VH 2.3 CDR-H3 | Residues 98-107 of SEQ ID NO.: 10 | DRGGASFFDY |
| VL 2.3 | SEQ ID NO.: 11 | DIQMTQSPSSLSASIGDRVT ITCRASQIIGGYLNWYQQRP GKAPKFLIYSTSILQSGVPS RFSGSGSGTDFTLTISSLQP EDFATYYCQQTYITPPTFGP GTKVDIKR |
| VL 2.3 CDR-L1 | Residues 24-34 of SEQ ID NO.: 11 | RASQIIGGYLN |
| VL 2.3 CDR-L2 | Residues 50-56 of SEQ ID NO.: 11 | STSILQS |
| VL 2.3 CDR-L3 | Residues 89-97 of SEQ ID NO.: 11 | QQTYITPPT |
| VH 215 | SEQ ID NO.: 12 | QVQLQESGPGLVKPSQTLSL TCTVSGGSINSGDYYWSWIR QHPGKGLEWIGHISYRGTTY YNPSLKSRVTISVDTSKNQF SLKLSSVTAADTAVYCCARD RGGGFFDLWGRGTLVTVSS |
| VH 215 CDR-H1 | Residues 31-37 of SEQ ID NO.: 12 | SGDYYWS |
| VH 215 CDR-H2 | Residues 52-67 of SEQ ID NO.: 12 | HISYRGTTYYNPSLKS |
| VH 215 CDR-H3 | Residues 100-108 of SEQ ID NO.: 12 | DRGGGFFDL |
| VL 215 | SEQ ID NO.: 13 | EIVLTQSPGTLSLSPGERAT LSCRASRSLSSGYLAWYQQK PGQAPRLLIYGASIRATGIP DRFSGSGSATDFTLTISRLE PEDFAVYYCQQYNYSPLTFG GGTRVEINR |
| VL 215 CDR-L1 | Residues 24-35 of SEQ ID NO.: 13 | RASRSLSSGYLA |
| VL 215 CDR-L2 | Residues 51-57 of SEQ ID NO.: 13 | GASIRAT |
| VL 215 CDR-L3 | Residues 90-98 of SEQ ID NO.: 13 | QQYNYSPLT |
| VH 231 | SEQ ID NO.: 14 | EVQLVESGGGSVQPRGSLRL SCAASGFTFSSYSMNWVRQA PGKGLEWVSYFSSSGGIIYY ADSVKGRFTISRDNAKNSLY LQNNSLRDEDTAVYYCARDD SSGYYPYFFDYWGQGTLVTV SS |
| VH 231 CDR-H1 | Residues 31-35 of SEQ ID NO.: 14 | SYSMN |
| VH 231 CDR-H2 | Residues 50-66 of SEQ ID NO.: 14 | YFSSSGGIIYYADSVKG |
| VH 231 CDR-H3 | Residues 99-111 of SEQ ID NO.: 14 | DDSSGYYPYFFDY |

TABLE 1-continued

List of Amino Acid Sequences of VH and VL regions

| Protein Protein region | Sequence Identifier | Sequence 12345678901234567890 |
|---|---|---|
| VL231 | SEQ ID NO.: 15 | DIVMTQSPDSLAVSLGERAT INCKSSQTVLYRSNNKNYLA WYQQKSGQPPKLLIYWASTR ESGVPDRFSGSGSGTDFTLT ISSLQAEDVAVYYCQQYYST PLTFGGGTKVEIKR |
| VL 231 CDR-L1 | Residues 24-40 of SEQ ID NO.: 15 | KSSQTVLYRSNNKNYLA |
| VL 231 CDR-L2 | Residues 56-62 of SEQ ID NO.: 15 | WASTRES |
| VL 231 CDR-L3 | Residues 95-103 of SEQ ID NO.: 15 | QQYYSTPLT |
| VH 251 | SEQ ID NO.: 16 | QLQLQESGPGLVKPSETLSL TCTVSGGSISSRVYYWGWIR QPPGKGLEWIGSIYYSGSTY YNPSLKSRVTISVDASKNQF SLKLSSVTAADTAIYYCARE DSSAWVFEHWGQGTLVTVSS |
| VH 251 CDR-H1 | Residues 31-37 of SEQ ID NO.: 16 | SRVYYWG |
| VH 251 CDR-H2 | Residues 52-67 of SEQ ID NO.: 16 | SIYYSGSTYYNPSLKS |
| VH 251 CDR-H3 | Residues 100-109 of SEQ ID NO.: 16 | EDSSAWVFEH |
| VL 251 | SEQ ID NO.: 17 | ETVLTQSPDTLSLSPGERAT LSCRASHILSRNYLAWYQQK PGQAPRLLMYGISIRATGIP DRFSGSGSGADFTLTINRLE PEDFAVYYCQHYDNSLCSEG QGTKLEVKR |
| VL 251 CDR-L1 | Residues 24-35 of SEQ ID NO.: 17 | RASHILSRNYLA |
| VL 251 CDR-L2 | Residues 51-57 of SEQ ID NO.: 17 | GISIRAT |
| VL 251 CDR-L3 | Residues 90-98 of SEQ ID NO.: 17 | QHYDNSLCS |
| VH 268 | SEQ ID NO.: 18 | QVQLVESGGGVVQPGRSLRL SCAASGFTFRNYGLHWVRQA PGKGLEWVAVIWYDGSNKYY ADSVKGRFTISRDNSKNTLY LQMNSLRAEDTAVYYCARES YYYYGMDVWGQGTTVTVSS |
| VH 268 CDR-H1 | Residues 31-35 of SEQ ID NO.: 18 | NYGLH |
| VH 268 CDR-H2 | Residues 20-36 of SEQ ID NO.: 18 | VIWYDGSNKYYADSVKG |
| VH 268 CDR-H3 | Residues 99-108 of SEQ ID NO.: 18 | ESYYYYGMDV |
| VL 268 | SEQ ID NO.: 19 | EIVMTQSPATLSVSPGERAT LSCRASQSFNSNLVWYQQKP GQAPRLLIYGASTRATGIPA RFSGSGSGTEFTLTISSLQS EDFAVYYCQQYNNWTWTFGQ GTKVEIKR |
| VL 268 CDR-L1 | Residues 24-34 of SEQ ID NO.: 19 | RASQSFNSNLV |
| VL 268 CDR-L2 | Residues 50-56 of SEQ ID NO.: 19 | GASTRAT |
| VL 268 CDR-L3 | Residues 89-97 of SEQ ID NO.: 19 | QQYNNWTWT |
| VH 336 | SEQ ID NO.: 20 | QVQLQESGPGLVKPSQTLSL TCTVSGGSINSGDYYWSWIR QHPGKGLEWIGHISYRGTTY YNPSLKSRVTISVDTSKNQF SLKLSSVTAADTAVYCCARD RGGGFFDLWGRGTLVTVSS |

TABLE 1-continued

List of Amino Acid Sequences of VH and VL regions

| Protein Protein region | Sequence Identifier | Sequence 12345678901234567890 |
|---|---|---|
| VH 336 CDR-H1 | Residues 31-35 of SEQ ID NO.: 20 | SGDYYWS |
| VH 336 CDR-H2 | Residues 52-67 of SEQ ID NO.: 20 | HISYRGTTYYNPSLKS |
| VH 336 CDR-H3 | Residues 100-108 of SEQ ID NO.: 20 | DRGGGFFDL |
| VL 336 | SEQ ID NO.: 21 | EIVLTQSPGTLSLSPGERAT LSCRASQSVSSGYLAWYQQK PGQAPRLLIYGASIRATGIP DRFSGSGSATDFTLTISRLE PEDFAVYYCQQYGYSPLTFG GGTRVEINR |
| VL 336 CDR-L1 | Residues 24-35 of SEQ ID NO.: 21 | RASQSVSSGYLA |
| VL 336 CDR-L2 | Residues 51-57 of SEQ ID NO.: 21 | GASIRAT |
| VL 336 CDR-L3 | Residues 90-98 of SEQ ID NO.: 21 | QQYGYSPLT |
| VH 351 | SEQ ID NO.: 22 | QVQLVESGGGVVQPGRSLRL SCAASGFTFSHYGMHWVRQA PGKGLEWVAVISYDGRNKYY VDSVKGRFTISRDNSKNTLY LQMNSLRAEDTAVFYCAREK GGSGWPPFYYYYGMDVWGQG TTVTVSS |
| VH 351 CDR-H1 | Residues 31-35 of SEQ ID NO.: 22 | HYGMH |
| VH 351 CDR-H2 | Residues 50-66 of SEQ ID NO.: 22 | VISYDGRNKYYVDSVKG |
| VH 351 CDR-H3 | Residues 99-116 of SEQ ID NO.: 22 | EKGGSGWPPFYYYYGMDV |
| VL 351 | SEQ ID NO.: 23 | DIVMTQTPLSLSVTPGQPAS ISCKSSQNLLYSDGETYLCW YLQKPGQPPQLLIYEVSNRF SGVPERFSGSGSGTDFTLKI SRVEAEDVGIYYCMQNVQLP LTFGGCTRVEIKR |
| VL 351 CDR-L1 | Residues 24-39 of SEQ ID NO.: 23 | KSSQNLLYSDGETYLC |
| VL 351 CDR-L2 | Residues 55-61 of SEQ ID NO.: 23 | EVSNRFS |
| VL 351 CDR-L3 | Residues 94-102 of SEQ ID NO.: 23 | MQNVQLPLT |
| VH 413 | SEQ ID NO.: 24 | QTQLQESGPGLVKPSETLSL TCTVSGGSISSRVYYWGWIR QPPGKGLEWIGSIYYSGSTY YSPSLKSRVTISVDTSKNQF SLKLSSVTAADTAIYYCARE DSSAWVFEHWGQGTLVTVSS |
| VH 413 CDR-H1 | Residues 31-37 of SEQ ID NO.: 24 | SRVYYWG |
| VH 413 CDR-H2 | Residues 52-67 of SEQ ID NO.: 24 | SIYYSGSTYYSPSLKS |
| VH 413 CDR-H3 | Residues 100-109 of SEQ ID NO.: 24 | EDSSAWVFEH |
| VL 413 | SEQ ID NO.: 25 | EIVLTQSPDTLSLSPGERAT LSCRASQILSPNYLAWYQQK PGQAPRLLIYGISIRATGIP DRFSGSGSGADFTLTINRLE PEDFAVYYCQHYDNSLCSFG QGTKLEVKR |
| VL 413 CDR-L1 | Residues 24-35 of SEQ ID NO.: 25 | RASQILSRNYLA |
| VL 413 CDR-L2 | Residues 51-57 of SEQ ID NO.: 25 | GISIRAT |
| VL 413 CDR-L3 | Residues 90-98 of SEQ ID NO.: 25 | QHYDNSLCS |

TABLE 1-continued

List of Amino Acid Sequences of VH and VL regions

| Protein<br>Protein region | Sequence Identifier | Sequence<br>12345678901234567890 |
|---|---|---|
| VH 435 | SEQ ID NO.: 26 | QLQLQESGPGLVKPSETLSL<br>TCTVSGGSTDSRIYYWGWIR<br>QPPGKGLEWIGSIYYRGSTY<br>YNPSLKSRVTISVDTPKNQF<br>SLKLNSVTAADTAVYYCARE<br>DSSAWVFDYWGQGTLATVSS |
| VH 435 CDR-H1 | Residues 31-37 of SEQ ID NO.: 26 | SRIYYWG |
| VH 435 CDR-H2 | Residues 52-67 of SEQ ID NO.: 26 | SIYYRGSTYYNPSLKS |
| VH 435 CDR-H3 | Residues 100-109 of SEQ ID NO.: 26 | EDSSAWVFDY |
| VL 435 | SEQ ID NO.: 27 | EIVLTQSPGTLSLSPGERAT<br>LSCRASQSVRNNYLNWYQQK<br>PGQAPRLLIYGAFSRATGIP<br>DRFSGSGSGTDFTLTISSLE<br>PEDFVVYYCQQYGNSIDSFG<br>QGTKLEINR |
| VL 435 CDR-L1 | Residues 24-35 of SEQ ID NO.: 27 | RASQSVRNNYLN |
| VL 435 CDR-L2 | Residues 51-57 of SEQ ID NO.: 27 | GAFSRAT |
| VL 435 CDR-L3 | Residues 90-98 of SEQ ID NO.: 27 | QYGNSIDS |
| VH 444 | SEQ ID NO.: 28 | QVQLQESGPGLVKPSQTLSL<br>TCTVSGGSINSGDYYWSYIR<br>QHPGKGLEWIGHISYRGTTY<br>YNPSLKSRVTISVDTSKNQF<br>SLKLSSVTAADTAVYCCARD<br>RGGGFFDLWGRGTLVTVSS |
| VH 444 CDR-H1 | Residues 31-37 of SEQ ID NO.: 28 | SGDYYWS |
| VH 444 CDR-H2 | Residues 52-67 of SEQ ID NO.: 28 | HISYRGTTYYNPSLKS |
| VH 444 CDR-H3 | Residues 100-108 of SEQ ID NO.: 28 | DRGGGFFDL |
| VL 444 | SEQ ID NO.: 29 | EIVLTQSPGTLSLSPGEPAT<br>LSCRASQSVSSGYLAWYQRK<br>PGQAPRLLIYGTSIRATGIP<br>DRFSGSGSATDFTLSISRLG<br>PEDFAVYYCQQYGYSPLTFG<br>GGTRVEINR |
| VL 444 CDR-L1 | Residues 24-35 of SEQ ID NO.: 29 | RASQSVSSGYLA |
| VL 444 CDR-L2 | Residues 51-57 of SEQ ID NO.: 29 | GTSIRAT |
| VL 444 CDR-L3 | Residues 90-98 of SEQ ID NO.: 29 | QQYGYSPLT |
| VH 478 | SEQ ID NO.: 30 | QVQLQESGPGLVKPSQTLSL<br>TCTVSGGSISSGGHYWSWIR<br>QHPGKGLEWIGYIYYSGSTH<br>YNPSLKSRVTISVDTSKNQF<br>SLKLRSVSAADTAGYYCASL<br>YNGNGYFDLWGRGTLVTVSS |
| VH 478 CDR-H1 | Residues 31-37 of SEQ ID NO.: 30 | SGGHYWS |
| VH 478 CDR-H2 | Residues 52-67 of SEQ ID NO.: 30 | YIYYSGSTHYNPSLKS |
| VH 478 CDR-H3 | Residues 99-109 of SEQ ID NO.: 30 | SLYNGNGYFDL |
| VL 478 | SEQ ID NO.: 31 | EIVLTQSPGTLSLSPGERAT<br>LSCRASQSISSGYLAWYQQK<br>PGQAPRLIIYGVSRRATGIP<br>DRFSGSGSGADFTLTISRLD<br>PEDFVVYYCQQYGFSPLTFG<br>GGTKVEIKR |

TABLE 1-continued

List of Amino Acid Sequences of VH and VL regions

| Protein Protein region | Sequence Identifier | Sequence 12345678901234567890 |
|---|---|---|
| VL 478 CDR-L1 | Residues 24-35 of SEQ ID NO.: 31 | RASQSISSCYLA |
| VL 478 CDR-L2 | Residues 51-57 of SEQ ID NO.: 31 | GVSRRAT |
| VL 478 CDR-L3 | Residues 90-98 of SEQ ID NO.: 31 | QQYGFSPLT |
| VH 521 | SEQ ID NO.: 32 | QLQLQESGPGLVKPSETLSL TCTVSGGSISRSYDYWGWIR QPPGKGLEWTGSIYYRGSTY YNPSLKSRVTISVDTSKNQF SLKLSSVTAADTAVYYCARE YSTTWSIDYWGQGTLVTVSS |
| VH 521 CDR-H1 | Residues 31-37 of SEQ ID NO.: 32 | RSYDYWG |
| VH 521 CDR-H2 | Residues 52-67 of SEQ ID NO.: 32 | SIYYRGSTYYNPSLKS |
| VH 521 CDR-H3 | Residues 100-109 of SEQ ID NO.: 32 | EYSTTWSIDY |
| VL 521 | SEQ ID NO.: 33 | ENVLTQSPGTLSLSPGERAT LSCRASQSIRNNYLAWYQQK PGQAPRLLIHGASSRATGIP DRFGGSGSGTDFTLTISRLE PEDFAVYFCQQYGNSIITFG PGTKVDVNR |
| VL 521 CDR-L1 | Residues 24-35 of SEQ ID NO.: 33 | RASQSIRNNYLA |
| VL 521 CDR-L2 | Residues 51-57 of SEQ ID NO.: 33 | GASSRAT |
| VL 521 CDR-L3 | Residues 90-98 of SEQ ID NO.: 33 | QQYGNSIIT |
| VH 550 | SEQ ID NO.: 34 | QVQLQESGPGLVKPSQTLSL TCTVSGGSINSGGYYWSWIR QHPGKGLEWIGHISYRGTTY SNPSLKSRVTISVDTSKNQF SLKLSSVTAADTAVYYCARD RGGGFFDLWGRGTLVTVSS |
| VH 550 CDR-H1 | Residues 31-37 of SEQ ID NO.: 34 | SGGYYWS |
| VH 550 CDR-H2 | Residues 52-67 of SEQ ID NO.: 34 | HISYRGTTYSNPSLKS |
| VH 550 CDR-H3 | Residues 100-108 of SEQ ID NO.: 34 | DRGGGFFDL |
| VL 550 | SEQ ID NO.: 35 | EIVLTQSPGTLSLSPGERAT LSCRASQSVNSGYLAWYQQK PGQAPRLLIYGVSIRATDIP DRFSGSGSATDFTLTISRLE PEDFAVYYCQQYGFSPLTFG GGTRVEINR |
| VL 550 CDR-L1 | Residues 24-35 of SEQ ID NO.: 35 | RASQSVNSGYLA |
| VL 550 CDR-L2 | Residues 51-57 of SEQ ID NO.: 35 | GVSIRAT |
| VL 550 CDR-L3 | Residues 90-98 of SEQ ID NO.: 35 | QQYGFSPLT |
| VH 581 | SEQ ID NO.: 36 | QVQLVESGGGVVQPGRSLRL SCAASGFTFSHCGMHWVRQA PGKGLEWVAVISYDGSNKYY ADSVKGRFTISRDNSKNTLY LQMNSLPAEDTAVYYCAKDH GGSGSPPFYYYYGMDVWGQG TTVTVSS |
| VH 581 CDR-H1 | Residues 31-35 of SEQ ID NO.: 36 | HCGMH |
| VH 581 CDR-H2 | Residues 50-66 of SEQ ID NO.: 36 | VISYDGSNKYYADSVKG |
| VH 581 CDR-H3 | Residues 99-116 of SEQ ID NO.: 36 | DHGGSGSPPFYYYYGMDV |

TABLE 1-continued

List of Amino Acid Sequences of VH and VL regions

| Protein<br>Protein region | Sequence Identifier | Sequence<br>12345678901234567890 |
|---|---|---|
| VL 581 | SEQ ID NO.: 37 | DILMTQTPLSLSVTPGQPAS<br>ISCKSSQSLLHGDGKTYLYW<br>YLQKPGQPPQFLIQELSNRF<br>SGVPDRFSGSGSGTDFTLKI<br>SRXEAEDVGVYYCMQSLQLP<br>LTFGGGTKVQIKR |
| VL 581 CDR-L1 | Residues 24-39 of SEQ ID NO.: 37 | KSSQSLLHGDGKTYLY |
| VL 581 CDR-L2 | Residues 55-61 of SEQ ID NO.: 37 | ELSNRFS |
| VL 581 CDR-L3 | Residues 94-102 of SEQ ID NO.: 37 | MQSLQLPLT |
| VH 7.5 | SEQ ID NO.: 38 | QVQLVESGGGVVQPGRSLRL<br>SCAASGFTFSYYGMHWVRQA<br>PGKGLEWVAVIWYDGRNKYY<br>ADSVKGRVTISRDNSKKTLY<br>LQMNSLRAEDTAVYYCAREG<br>GYYYGMDVWGQGTTVTVSS |
| VH 7.5 CDR-H1 | Residues 31-35 of SEQ ID NO.: 38 | YYGMH |
| VH 7.5 CDR-H2 | Residues 50-66 of SEQ ID NO.: 38 | VIWYDGRNKYYADSVKG |
| VH 7.5 CDR-H3 | Residues 99-108 of SEQ ID NO.: 38 | EGGYYYGNDV |
| VL 7.5 | SEQ ID NO.: 39 | EILLTQSPGTLSLSPGERAT<br>LSCRASQNVSSSYLAWYQQN<br>PGQAPRLLIYGASSRATGIP<br>DRFSGSGSGTDFTLTISRLE<br>PEDFEVYYCQQSGSSLFTFG<br>PGTKVDIKR |
| VL 7.5 CDR-L1 | Residues 24-35 of SEQ ID NO.: 39 | RASQNVSSSYLA |
| VL 7.5 CDR-L2 | Residues 51-57 of SEQ ID NO.: 39 | GASSRAT |
| VL 7.5 CDR-L3 | Residues 90-98 of SEQ ID NO.: 39 | QQSGSSLFT |
| VH 2.11 | SEQ ID NO.: 40 | QVQLQESGPGLVKPSQTLSL<br>TCTVSGGSIRSGDHYWTWIR<br>QHPGKGLEWIGHIYYSGSTY<br>YNPSLKSRLTISIDTSKNQF<br>SLKLSSVTAADTAVYYCARD<br>YGGNGYFDYWGQGTLVTVSS |
| VH 2.11 CDR-H1 | Residues 31-37 of SEQ ID NO.: 40 | SGDHYWT |
| VH 2.11 CDR-H2 | Residues 52-67 of SEQ ID NO.: 40 | HIYYSGSTYYNPSLKS |
| VH 2.11 CDR-H3 | Residues 97-109 of SEQ ID NO.: 40 | CARDYGGNGYFDY |
| VL 2.11 | SEQ ID NO.: 41 | DIVMTQTPLSLPVTPGEPAS<br>ISCRSSQSLLDSDDGNTYLD<br>WYLQKPGQSPQLLIYTLSYR<br>ASGVPDRFSGSGSGTDFTLN<br>ISRVEAEDVGVYYCMQRIEF<br>PITFGQGTRLEIKR |
| VL 2.11 CDR-L1 | Residues 24-40 of SEQ ID NO.: 41 | RSSQSLLDSDDGNTYLD |
| VL 2.11 CDR-L2 | Residues 56-62 of SEQ ID NO.: 41 | TLSYRAS |
| VL 2.11 CDR-L3 | Residues 95-103 of SEQ ID NO.: 41 | MQRIEFPIT |

The foregoing isolated anti-IL-18 antibody CDR sequences establish a novel family of IL-18 binding proteins, isolated in accordance with this invention, and comprising polypeptides that include the CDR sequences listed in Table 2 below. To generate and to select CDR's of the invention having preferred IL-18 binding and/or neutralizing activity, standard methods known in the art for generating binding proteins of the present invention and assessing the IL-18 binding and/or neutralizing characteristics of those binding protein may be used, including but not limited to those specifically described herein.

TABLE 2

Consensus IL-18 CDR affinity ligands
(alternative residues are listed below each amino
acid position; — indicates residue may be absent).

| CDR region | Sequence Identifier | Consensus Sequence |
|---|---|---|
| CDR-H1 | SEQ ID NO.: 42 | $X_1$ $X_2$ $X_3$ $X_4$ $X_5$ $X_6$ $X_7$ |

```
                        X1  X2  X3  X4  X5  X6  X7
                        S   Y   W   I   G   —   —
                        N   G   G   H   Y   W   T
                        H   R   Y   W   S       S
                        R   S   D   Y   N       G
                        Y   C   S   M   H
                            V   L
                            I   D
```

CDR-H2 SEQ ID NO.: 43  $X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $X_{17}$

```
    F   I   Y   P   G   D   S   E   T   R   Y   S   P   T   F   Q   —
    Y   F   S   Y   S   G   T   T   Y   N   P   S   L   K   S   G
    H       W   S   R       G   I   N   S   S   A   D   S   V   K
    S                   D           R   N   I           V
    V                                       K
                                            H
```

CDR-H3 SEQ ID NO.: 44  $X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $X_{17}$ $X_{18}$

```
    V   G   S   G   W   Y   P   Y   T   —   —   —   —   —   —   —   —   —
    D   R   G   S   S   G   S   F   W   F   D   I   Y   Y   G   M   D   V
    E   D   Y   Y   A   S   F   D   D   D   Y   D
    S   S   R   N   G   F   Y   P   L   Y   F   Y
    C   K       T   Y   W   V   M   Y   H   L
                L       D   T   N   G   I   E   V
                Y               W   N   P   Y
                A                   V   F
                                        G
```

CDR-L1 SEQ ID NO.: 45  $X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $X_{17}$

```
    R   A   S   E   S   I   S   S   N   L   A   —   —   —   —   —   —
    K   G       R   I   V   G   G   G   Y   L   A   K   N   Y   L   A
    S           Q   T   L   L   Y   Y   S   N   N   T   Y   L   C   D
                H   N   F   N   R   R   D   V   E   N   T       Y
                            R   N   S       G   K
                                H           D   G
                                D
```

CDR-L2 SEQ ID NO.: 46  $X_1$ $X_2$ $X_3$ $X_4$ $X_5$ $X_6$ $X_7$

```
    T   A   S   T   R   A   T
    G   V   F   I   L   Q   S
    S   T       N       E
    W   I       S       F
    E   L       R
            Y
```

CDR-L3 SEQ ID NO.: 47  X1 X2 X3 X4 X5 X6 X7 X8 X9 X10

```
    Q   Q   Y   N   N   W   P   S   —   —
    M   H   N   H   G   S   L   L   I   T
        Y   G   Y   I   T   T   P   T
            S   D   Y   L   D   C   S
            R   G   S   I   I   W
                V   Q   F       I
                L   F           F
                I   E
```

D. Uses of Anti-IL-18 Antibodies

Given their ability to bind to human IL-18, the anti-human IL-18 antibodies, or portions thereof, of the invention can be used to detect human IL-18 (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting human IL-18 in a biological sample comprising contacting a biological sample with an antibody, or antibody portion, of the invention and detecting either the antibody (or antibody portion) bound to human IL-18 or unbound antibody (or antibody portion), to thereby detect human IL-18 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

Alternative to labeling the antibody, human IL-18 can be assayed in biological fluids by a competition immunoassay utilizing rhIL-18 standards labeled with a detectable substance and an unlabeled anti-human IL-18 antibody. In this assay, the biological sample, the labeled rhIL-18 standards and the anti-human IL-18 antibody are combined and the amount of labeled rhIL-18 standard bound to the unlabeled antibody is determined. The amount of human IL-18 in the biological sample is inversely proportional to the amount of labeled rhIL-18 standard bound to the anti-IL-18 antibody.

The antibodies and antibody portions of the invention preferably are capable of neutralizing human IL-18 activity both in vitro and in vivo. Accordingly, such antibodies and antibody portions of the invention can be used to inhibit hIL-18 activity, e.g., in a cell culture containing hIL-18, in human subjects or in other mammalian subjects having IL-18 with which an antibody of the invention cross-reacts. In one embodiment, the invention provides a method for inhibiting IL-18 activity comprising contacting IL-18 with an antibody or antibody portion of the invention such that IL-18 activity is inhibited. Preferably, the IL-18 is human IL-18. For example, in a cell culture containing, or suspected of containing hIL-18, an antibody or antibody portion of the invention can be added to the culture medium to inhibit hIL-18 activity in the culture.

In another embodiment, the invention provides a method for reducing IL-18 activity in a subject, advantageously from a subject suffering from a disease or disorder in which IL-18 activity is detrimental. The invention provides methods for reducing IL-18 activity in a subject suffering from such a disease or disorder, which method comprises administering to the subject an antibody or antibody portion of the invention such that IL-18 activity in the subject is reduced. Preferably, the IL-18 is human IL-18 and the subject is a human subject. Alternatively, the subject can be a mammal expressing an IL-18 to which an antibody of the invention is capable of binding. Still further the subject can be a mammal into which hIL-18 has been introduced (e.g., by administration of hIL-18 or by expression of an hIL-18 transgene). An antibody of the invention can be administered to a human subject for therapeutic purposes. Moreover, an antibody of the invention can be administered to a non-human mammal expressing an IL-18 with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which IL-18 activity is detrimental" is intended to include diseases and other disorders in which the presence of IL-18 in a subject suffering from the disorder has been shown to be or is suspected of being either responsible for the pathophysiology of the disorder or a factor that contributes to a worsening of the disorder. Accordingly, a disorder in which IL-18 activity is detrimental is a disorder in which reduction of IL-18 activity is expected to alleviate the symptoms and/or progression of the disorder. Such disorders may be evidenced, for example, by an increase in the concentration of IL-18 in a biological fluid of a subject suffering from the disorder (e.g., an increase in the concentration of IL-18 in serum, plasma, synovial fluid, etc. of the subject), which can be detected, for example, using an anti-IL-18 antibody as described above. Non-limiting examples of disorders that can be treated with the antibodies of the invention include those disorders discussed in the section below pertaining to pharmaceutical compositions of the antibodies of the invention.

D. Pharmaceutical Composition

The invention also provides pharmaceutical compositions comprising an antibody, or antigen-binding portion thereof, of the invention and a pharmaceutically acceptable carrier. In one embodiment, the pharmaceutical composition further comprises at least one additional therapeutic agent for treating a disorder in which IL-18 activity is detrimental.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which IL-18 activity is detrimental. For example, an anti-hIL-18 antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to IL-18 or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

Interleukin 18 plays a critical role in the pathology associated with a variety of diseases involving immune and inflammatory elements. These diseases include, but are not limited to, rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, *chlamydia, yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B *streptococci* (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma). The human antibodies, and antibody portions of the invention can be used to treat humans suffering from autoimmune diseases, in particular those associated with inflammation, including, rheumatoid spondylitis, allergy, autoimmune diabetes, autoimmune uveitis.

Preferably, the antibodies of the invention or antigen-binding portions thereof, are used to treat rheumatoid arthritis, Crohn's disease, multiple sclerosis, insulin dependent diabetes, mellitus and psoriasis.

An antibody, or antibody portion, of the invention also can be administered with one or more additional therapeutic agents useful in the treatment of autoimmune and inflammatory diseases.

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the anti-IL-18 antibodies of this invention. Non-limiting examples of therapeutic agents for rheumatoid arthritis with which an antibody, or antibody portion, of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7, (PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The antibodies of the invention, or antigen binding portions thereof, may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFα converting enzyme (TACE) inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline hcl, sulfadiazine, oxycodone hcl/acetaminophen, olopatadine hcl, misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine.

Non-limiting examples of therapeutic agents for inflammatory bowel disease with which an antibody, or antibody portion, of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90 or their ligands. The antibodies of the invention, or antigen binding portions thereof, may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TNFα converting enzyme inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ).

Preferred examples of therapeutic agents for Crohn's disease in which an antibody or an antigen binding portion can be combined include the following: TNF antagonists, for example, anti-TNF antibodies, D2E7 (PCT Publication No. WO 97/29131; HUMIRA), CA2 (REMICADE), CDP 571, TNFR-Ig constructs, (p75TNFRIgG (ENBREL) and p55TNFRIgG (LENERCEPT)) inhibitors and PDE4 inhibitors. Antibodies of the invention, or antigen binding portions thereof, can be combined with corticosteroids, for example, budenoside and dexamethasone. Antibodies of the invention or antigen binding portions thereof, may also be combined with agents such as sulfasalazine, 5-aminosalicylic acid and olsalazine, and agents which interfere with synthesis or action of proinflammatory cytokines such as IL-1, for example, IL-1β converting enzyme inhibitors and IL-1ra. Antibodies of the invention or antigen binding portion thereof may also be used with T cell signaling inhibitors, for example, tyrosine kinase inhibitors 6-mercaptopurines. Antibodies of the invention, or antigen binding portions thereof, can be combined with IL-11. Antibodies of the invention, or antigen binding portions thereof, can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab and interferon-gamma Non-limiting examples of therapeutic agents for multiple sclerosis with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (AVONEX; Biogen); interferon-β1b (BETASERON; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. Antibodies of the invention, or antigen binding portions thereof, can be combined with antibodies to cell surface molecules such as CD2, CD3, CD4, CD8, CD19, CD20, CD25, CD28, CD30, CD40, CD45, CD69, CD80, CD86, CD90 or their ligands. The antibodies of the invention, or antigen binding portions thereof, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adenssosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL4, IL-10, IL-13 and TGFβ).

Preferred examples of therapeutic agents for multiple sclerosis in which the antibody or antigen binding portion thereof can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

The antibodies of the invention, or antigen binding portions thereof, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists.

Non-limiting examples of therapeutic agents for Angina with which an antibody, or antibody portion, of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil hcl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, bisoprolol fumarate.

Non-limiting examples of therapeutic agents for Ankylosing Spondylitis with which an antibody, or antibody portion, of the invention can be combined include the following: ibuprofen, diclofenac and misoprostol, naproxen, meloxicam, indomethacin, diclofenac, celecoxib, rofecoxib, Sulfasalazine, Methotrexate, azathioprine, minocyclin, prednisone, etanercept, infliximab.

Non-limiting examples of therapeutic agents for Asthma with which an antibody, or antibody portion, of the invention can be combined include the following: albuterol, salmeterol/fluticasone, montelukast sodium, fluticasone propionate, budesonide, prednisone, salmeterol xinafoate, levalbuterol hcl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin hcl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine hcl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate.

Non-limiting examples of therapeutic agents for COPD with which an antibody, or antibody portion, of the invention can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol hcl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, Cilomilast, Roflumilast.

Non-limiting examples of therapeutic agents for HCV with which an antibody, or antibody portion, of the invention can be combined include the following: Interferon-alpha-2a, Interferon-alpha-2b, Interferon-alpha con1, Interferon-alpha-n1, Pegylated interferon-alpha-2a, Pegylated interferon-alpha-2b, ribavirin, Peginterferon alfa-2b+ribavirin, Ursodeoxycholic Acid, Glycyrrhizic Acid, Thymalfasin, Maxamine, VX-497 and any compounds that are used to treat HCV through intervention with the following targets: HCV polymerase, HCV protease, HCV helicase, HCV IRES (internal ribosome entry site).

Non-limiting examples of therapeutic agents for Idiopathic Pulmonary. Fibrosis with which an antibody, or antibody portion, of the invention can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone hcl, potassium chloride, triamcinolone acetonide, tacrolimus anhydrous, calcium, interferon-alpha, methotrexate, mycophenolate mofetil, Interferon-gamma-1β.

Non-limiting examples of therapeutic agents for Myocardial Infarction with which an antibody, or antibody portion, of the invention can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, cariporide.

Non-limiting examples of therapeutic agents for Psoriasis with which an antibody, or antibody portion, of the invention can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine.

Non-limiting examples of therapeutic agents for Psoriatic Arthritis with which an antibody, or antibody portion, of the invention can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab.

Non-limiting examples of therapeutic agents for Restenosis with which an antibody, or antibody portion, of the invention can be combined include the following: sirolimus, paclitaxel, everolimus, tacrolimus, ABT-578, acetaminophen.

Non-limiting examples of therapeutic agents for Sciatica with which an antibody, or antibody portion, of the invention can be combined include the following: hydrocodone bitartrate/apap, rofecoxib, cyclobenzaprine hcl, methylprednisolone, naproxen, ibuprofen, oxycodone hcl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone hcl, tizanidine hcl, diclofenac sodium/misoprostol, propoxyphene napsylate/apap, asa/oxycod/oxycodone ter, ibuprofen/hydrocodone bit, tramadol hcl, etodolac, propoxyphene hcl, amitriptyline hcl, carisoprodol/codeine phos/asa, morphine sulfate, multivitamins, naproxen sodium, orphenadrine citrate, temazepam.

Preferred examples of therapeutic agents for SLE (Lupus) in which an antibody or an antigen binding portion can be combined include the following: NSAIDS, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; Cytotoxics, for example, azathioprine, cyclophosphamide, mycophenolate mofetil, methotrexate; inhibitors of PDE4 or purine synthesis inhibitor, for example Cellcept. Antibodies of the invention or antigen binding portions thereof, may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. Antibodies of the invention or antigen binding portion thereof may also be used with T cell signaling inhibitors, for example, tyrosine kinase inhibitors; or molecules that target T cell activation molecules, for example, CTLA-4-IgG or anti-B7 family antibodies, anti-PD-1 family antibodies. Antibodies of the invention, or antigen binding portions thereof, can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Antibodies of the invention or antigen binding portion thereof may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (PCT Publication No. WO 97/29131; HUMIRA), CA2 (REMICADE), CDP 571, TNFR-Ig constructs, (p75TNFRIgG (ENBREL) and p55TNFRIgG (LENERCEPT)).

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

II. IL-18 Responsive Genes

IL-18 is expressed in macrophages, dendritic cells, Kupffer cells, microglia, epithelial cells, keratinocytes, intestinal epithelial cells, chondrocytes, synovial fibroblasts and osteoblasts, as well as within the adrenal cortex and pituitary gland.

In some cells, such as human monocytes and dendritic cells, expression is constitutive, whereas in other cells it must be induced de novo.

Apart from interferon gamma expression, little is known about other genes induced by IL-18 alone or in concert with other cytokines.

One embodiment of the invention provides a method for regulating gene expression of a gene of interest comprising the steps of providing IL-18 or an IL-18 modulator; and contacting IL-18 or the modulator to a cell wherein the gene of interest is selected from the group consisting of the genes presented in the following table.

TABLE 3

IL-18 Responsive Genes

| Genbank ID | Gene Name | Unigene Comment |
|---|---|---|
| NM_000389 | p21 | cyclin-dependent kinase inhibitor 1A (p21, Cip1) |
| NM_002198 | IRF1 | interferon regulatory factor 1 |
| NM_002163 | ICSBP1 | interferon consensus sequence binding protein 1 |
| NM_006144 | GZMA | granzyme A |
| NM_006515 | SETMAR | SET domain and mariner transposase fusion gene |
| NM_007185 | TNRC4 | trinucleotide repeat containing 4 |
| NM_002288 | LAIR2 | leukocyte-associated Ig-like receptor 2 |
| NM_003661 | APOL1 | apolipoprotein L, 1 |
| NM_021958 | HLX1 | H2.0-like homeo box 1 (*Drosophila*) |
| NM_001335 | CTSW | cathepsin W (lymphopain) |
| Hs.382006 | FCGR1B | FcRI b form (AA 1-344) |
| NM_020125 | BLAME | leucine aminopeptidase 3 |
| NM_007210 | GALNT6 | UDP-N-acetyl-alpha-D-galactosamine |
| NM_021798 | IL21R | interleukin 21 receptor |
| NM_013324 | CISH | cytokine inducible SH2-containing protein |
| M11313 | A2M | alpha-2-macroglobulin |
| D88152 | ACATN | acetyl-Coenzyme A transporter |
| NM_001103 | ACTN2 | actinin, alpha 2 |
| U37519 | ALDH8 | aldehyde dehydrogenase 8 |
| NM_000697 | ALOX12 | arachidonate 12-lipoxygenase |
| J03600 | ALOX5 | arachidonate 5-lipoxygenase |
| NM_014578 | ARHD | ras homolog gene family, member |
| S66793 | ARR3 | arrestin 3, retinal (X-arrestin) |
| U47054 | ART3 | ADP-ribosyltransferase 3 |
| L19871 | ATF3 | activating transcription factor 3 |
| M81181 | ATP1B2 | ATPase, Na+/K+ transporting |
| NM_001188 | BAK1 | BCL2-antagonist/killer 1 |
| U15460 | BATF | basic leucine zipper transcription factor, ATF-like |
| NM_014417 | BBC3 | Bcl-2 binding component 3 |
| Z23115 | BCL2L1 | BCL2-like 1 |
| NM_001713 | BHMT | betaine-homocysteine methyltransferase |
| U45878 | BIRC3 | baculoviral IAP repeat-containing 3 |
| U37546 | BIRC3 | baculoviral IAP repeat-containing 3 |
| U72649 | BTG2 | BTG family, member 2 |
| U49187 | C6ORF32 | chromosome 6 open reading frame 32 |
| J03507 | C7 | complement component 7 |
| U50360 | CAMK2G | CaM kinase II gamma |
| XM_071866 | CAT56 | CAT56 protein |
| NM_005623 | CCL8 | |
| Z32765 | CD36 | CD36 antigen (collagen type I/TSP receptor) |
| HG2981-HT3127 | CD44 | CD44 antigen |
| Z11697 | CD83 | CD83 antigen |
| XM_071866 | CDR2 | cerebellar degeneration-related protein (62 kD) |
| U51096 | CDX2 | caudal type homeo box transcription factor 2 |
| M83667 | CEBPD | CCAAT/enhancer binding protein (C/EBP), delta |
| D87469 | CELSR2 | cadherin, EGF LAG seven-pass G-type receptor 2 |
| L07765 | CES1 | carboxylesterase 1 |
| U66468 | CGR11 | cell growth regulatory with EF-hand domain |
| X14830 | CHRNB1 | cholinergic receptor, nicotinic, beta polypeptide 1 |
| L29217 | CLK3 | CDC-like kinase 3 |
| X15880 | COL6A1 | collagen, type VI, alpha 1 |
| NM_001851 | COL9A1 | collagen, type IX, alpha 1 |
| M27691 | CREB1 | cAMP responsive element binding protein 1 |
| M37435 | CSF1 | colony stimulating factor 1 (macrophage) |
| HG3548-HT3749 | CUTL1 | cut (CCAAT displacement protein) |
| X13589 | CYP19 | cytochrome P450, subfamily XIX |
| X16866 | CYP2D7AP | cytochrome P450, subfamily IID |
| X59131 | D13S106E | highly charged protein |
| NM_004393 | DAG1 | dystroglycan 1 |
| U73328 | DLX4 | distal-less homeobox 4 |
| L19267 | DMWD | *dystrophia myotonica*, WD repeat motif |
| U53445 | DOC1 | downregulated in ovarian cancer 1 |
| X68277 | DUSP1 | dual specificity phosphatase 1 |
| U48807 | DUSP4 | dual specificity phosphatase 4 |
| NM_001950 | E2F4 | E2F transcription factor 4, p107/p130-binding |
| U87269 | E4F1 | E4F transcription factor 1 |

TABLE 3-continued

IL-18 Responsive Genes

| Genbank ID | Gene Name | Unigene Comment |
|---|---|---|
| M57730 | EFNA1 | ephrin-A1 |
| X52541 | EGR1 | early growth response 1 |
| J04076 | EGR2 | early growth response 2 (Krox-20 homolog) |
| X63741 | EGR3 | early growth response 3 |
| L07077 | EHHADH | enoyl-Coenzyme A |
| M62831 | ETR101 | immediate early protein |
| M60830 | EVI2B | ecotropic viral integration site 2B |
| U53786 | EVPL | envoplakin |
| NM_001988 | EVPL | envoplakin |
| NM_000141 | FCGBP | Fc fragment of IgG binding protein |
| M23668 | FDX1 | ferredoxin 1 |
| U60062 | FEZ1 | fasciculation & elongation protein zeta 1 (zygin I) |
| NM_000141 | FGFR2 | fibroblast growth factor receptor 2 |
| U49973 | FLJ10803 | hypothetical protein FLJ10803 |
| U89995 | FOXE1 | forkhead box E1 (thyroid transcription factor 2) |
| U27326 | FUT3 | fucosyltransferase 3 |
| A28102 | GABRA3 | gamma-aminobutyric acid (GABA) receptor |
| M25667 | GAP43 | growth associated protein 43 |
| L34357 | GATA4 | GATA-binding protein 4 |
| U19523 | GCH1 | GTP cyclohydrolase 1 |
| L01406 | GHRHR | growth hormone releasing hormone receptor |
| U03486 | GJA5 | gap junction protein, alpha 5, 40 kD (connexin 40) |
| X68285 | GK | glycerol kinase |
| Z18859 | GNAT2 | guanine nucleotide binding protein (G protein) |
| HG870-HT870 | GOLGA3 | golgi autoantigen, golgin subfamily a, 3 |
| D49958 | GPM6A | glycoprotein M6A |
| D43772 | GRB7 | growth factor receptor-bound protein 7 |
| AC000099 | GRM8 | glutamate receptor, metabotropic 8 |
| M57731 | GRO2 | GRO2 oncogene |
| X53800 | GRO3 | GRO3 oncogene |
| M91036 | HBG2 | hemoglobin, gamma G |
| D16583 | HDC | histidine decarboxylase |
| X64877 | HFL3 | H factor (complement)-like 3 |
| X58431 | HOXB6 | homeo box B6 |
| M16937 | HOXB7 | homeo box B7 |
| NM_014468 | HPX42B | haemopoietic progenitor homeobox |
| X92814 | HREV107 | similar to rat HREV 107 |
| L19314 | HRY | hairy (*Drosophila*)-homolog |
| M26665 | HTN3 | histatin 3 |
| D10995 | HTR1B | 5-hydroxytryptamine (serotonin) receptor 1B |
| L41147 | HTR6 | 5-hydroxytryptamine (serotonin) receptor 6 |
| M24283 | ICAM1 | intercellular adhesion molecule 1 (CD54) |
| S81914 | IER3 | immediate early response 3 |
| J03171 | IFNAR1 | interferon (alpha, beta and omega) receptor 1 |
| J00219 | IFNG | interferon, gamma |
| NM_000619 | IFNG | interferon, gamma |
| NM_000585 | IL15 | interleukin 15 |
| U31628 | IL15RA | interleukin 15 receptor, alpha |
| X04500 | IL1B | interleukin 1, beta |
| M27492 | IL1R1 | interleukin 1 receptor, type I |
| X01057 | IL2RA | interleukin 2 receptor, alpha |
| M26062 | IL2RB | interleukin 2 receptor, beta |
| Y00081 | IL6 | interleukin 6 (interferon, beta 2) |
| Y00787 | IL8 | interleukin 8 |
| Z31695 | INPP5A | inositol polyphosphate-5-phosphatase, 40 kD |
| X06256 | ITGA5 | integrin, alpha 5 |
| X57206 | ITPKB | inositol 1,4,5-trisphosphate 3-kinase B |
| U20734 | JUNB | jun B proto-oncogene |
| NM_014879 | KIAA0001 | putative G protein coupled receptor for UDP-glucose |
| D31762 | KIAA0057 | TRAM-like protein |
| D42038 | KIAA0087 | KIAA0087 gene product |
| NM_005551 | KIAA0133 | KIAA0133 gene product |
| NM_014846 | KIAA0196 | KIAA0196 gene product |
| X06182 | KIT | v-kit oncogene homolog |
| NM_005551 | KLK2 | kallikrein 2, prostatic |
| X07730 | KLK3 | kallikrein 3, (prostate specific antigen) |
| M13955 | KRT7 | keratin 7 |
| M57710 | LGALS3 | lectin, galactoside-binding, soluble, 3 (galectin 3) |
| S83362 | LIFR | leukemia inhibitory factor receptor |
| NM_002314 | LIMK1 | LIM domain kinase 1 |
| NM_005569 | LIMK2 | LIM domain kinase 2 |
| U49957 | LPP | LIM domain-containing |
| U89922 | LTB | lymphotoxin beta (TNF superfamily, member 3) |
| X14008 | LYZ | lysozyme (renal amyloidosis) |
| U59914 | MADH6 | MAD) homolog 6 |
| D14497 | MAP3K8 | mitogen-activated protein kinase kinase kinase 8 |

TABLE 3-continued

IL-18 Responsive Genes

| Genbank ID | Gene Name | Unigene Comment |
|---|---|---|
| X59727 | MAPK4 | mitogen-activated protein kinase 4 |
| NM_000429 | MAT1A | methionine adenosyltransferase I, alpha |
| HG1877-HT1917 | MBP | myelin basic protein |
| HG3115-HT3291 | MBP | myelin basic protein |
| U43944 | ME1 | malic enzyme 1, NADP(+)-dependent, cytosolic |
| X72755 | MIG | monokine induced by gamma interferon |
| NM_021230 | MLL3 | myeloid/lymphoid or mixed-lineage leukemia3 |
| NM_005951 | MT1H | metallothionein 1H |
| X78710 | MTF1 | metal-regulatory transcription factor 1 |
| X70991 | NAB2 | NGFI-A binding protein 2 (ERG1 bp 2) |
| M32011 | NCF2 | neutrophil cytosolic factor 2 |
| S77763 | NFE2 | nuclear factor (erythroid-derived 2), 45 kD |
| M58603 | NFKB1 | nuclear factor kappa B (p105) |
| S76638 | NFKB2 | nuclear factor kappa B |
| M69043 | NFKBIA | nuclear factor kappa B |
| U91616 | NFKBIE | nuclear factor kappa B |
| D86425 | NID2 | nidogen 2 |
| L13740 | NR4A1 | nuclear receptor subfamily 4, group A, member 1 |
| U44848 | NRF1 | nuclear respiratory factor 1 |
| U79251 | OPCML | opioid-binding protein/cell adhesion molecule-like |
| HG4115-HT4385 | OR1E3P | olfactory receptor |
| M27288 | OSM | oncostatin M |
| AF000234 | P2RX4 | purinergic receptor P2X |
| D50640 | PDE3B | phosphodiesterase 3B, cGMP-inhibited |
| L20971 | PDE4B | phosphodiesterase 4B, cAMP-specific |
| L10343 | PI3 | protease inhibitor 3, skin-derived (SKALP) |
| U77735 | PIM2 | pim-2 oncogene |
| NM_003579 | PIP5K2A | phosphatidylinositol-4-phosphate 5-kinase |
| U17034 | PLA2R1 | phospholipase A2 receptor 1, 180 kD |
| AB000584 | PLAB | prostate differentiation factor |
| X63131 | PML | promyelocytic leukemia |
| D11428 | PMP22 | peripheral myelin protein 22 |
| NM_032940 | POLR2C | polymerase (RNA) II polypeptide |
| NM_005035 | POLRMT | polymerase (RNA) mitochondrial (DNA directed) |
| NM_003579 | POU2F2 | POU domain, class 2, transcription factor 2 |
| M18255 | PRKCB1 | protein kinase C, beta 1 |
| L01087 | PRKCQ | protein kinase C, theta |
| D38128 | PTGIR | prostaglandin I2 (prostacyclin) receptor (IP) |
| Y10375 | PTPNS1 | tyrosine phosphatase, non-receptor substrate 1 |
| D15049 | PTPRH | protein tyrosine phosphatase, receptor type, H |
| M31166 | PTX3 | pentaxin-related gene, |
| U59877 | RAB31 | RAB31, member RAS oncogene family |
| NM_003579 | RAD54L | RAD54 (S. cerevisiae)-like |
| U64675 | RANBP2L1 | RAN binding protein 2-like 1 |
| S57153 | RBBP1 | retinoblastoma-binding protein 1 |
| NM_002903 | RCV1 | recoverin |
| NG_000013 | RDBP | RD RNA-binding protein |
| X75042 | REL | v-rel |
| M83221 | RELB | v-rel |
| NM_000537 | REN | renin |
| U22314 | REST | RE1-silencing transcription factor |
| S59049 | RGS1 | regulator of G-protein signalling 1 |
| U70426 | RGS16 | regulator of G-protein signalling 16 |
| U22377 | RLF | rearranged L-myc fusion sequence |
| U38480 | RXRG | retinoid X receptor, gamma |
| L10338 | SCN1B | sodium channel polypeptide |
| M23178 | SCYA3 | small inducible cytokine A3 |
| M69203 | SCYA4 | small inducible cytokine A4 |
| NM_005409 | SCYB11 | small inducible cytokine subfamily B: CXC11 |
| D79206 | SDC4 | syndecan 4 (amphiglycan, ryudocan) |
| NM_005065 | SEL1L | sel-1 (suppressor of lin-12, C. elegans)-like |
| NM_004186 | SEMA3F | semaphorin 3F |
| J03764 | SERPINE1 | nexin, plasminogen activator inhibitor type 1 |
| NM_006802 | SF3A3 | splicing factor 3a, subunit 3, 60 kD |
| HG3925-HT4195 | SFTPA2 | surfactant, pulmonary-associated protein A2 |
| D89077 | SLA | Src-like-adapter |
| NM_003037 | SLAM | signaling lymphocytic activation molecule |
| M91463 | SLC2A4 | solute carrier family 2 glucose transporter |
| D82326 | SLC3A1 | solute carrier family 3 |
| L05568 | SLC6A4 | solute carrier family 6 (serotonin), |
| U96094 | SLN | sarcolipin |
| X83301 | SMA3 | SMA3 |

TABLE 3-continued

IL-18 Responsive Genes

| Genbank ID | Gene Name | Unigene Comment |
|---|---|---|
| D21267 | SNAP25 | synaptosomal-associated protein, 25 kD |
| L31529 | SNTB1 | syntrophin, dystrophin-associated protein A1, |
| HG961-HT961 | SOS1 | son of sevenless (*Drosophila*) homolog 1 |
| M62800 | SSA1 | (52 kD, ribonucleoprotein autoantigen SS-A/Ro) |
| NM_021014 | SSX3 | synovial sarcoma, X breakpoint 3 |
| Z35093 | SURF1 | surfeit 1 |
| NM_005816 | TACTILE | T cell activation, increased late expression |
| L25444 | TAF2E | TATA box binding protein (TBP)-associated factor |
| M95787 | TAGLN | transgelin |
| NM_005421 | TAL2 | T-cell acute lymphocytic leukemia 2 |
| L47345 | TCEB3 | transcription elongation factor B (110 kD, elongin A) |
| M57732 | TCF1 | hepatic nuclear factor (HNF1) |
| NM_003205 | TCF12 | helix-loop-helix transcription factors 4 |
| M96956 | TDGF1 | teratocarcinoma-derived growth factor 1 |
| U19878 | TMEFF1 | transmembrane with EGF and follistatin like |
| M92357 | TNFAIP2 | tumor necrosis factor, alpha-induced protein 2 |
| M59465 | TNFAIP3 | tumor necrosis factor, alpha-induced protein 3 |
| X83490 | TNFRSF6 | tumor necrosis factor receptor member 6 |
| U37518 | TNFSF10 | tumor necrosis factor member 10 |
| NM_003294 | TPSB1 | tryptase beta 1 |
| U19261 | TRAF1 | TNF receptor-associated factor 1 |
| U78798 | TRAF6 | TNF receptor-associated factor 6 |
| S69790 | WASF3 | WAS protein family, member 3 |
| U53476 | WNT7A | wingless-type MMTV integration site family |
| L15309 | ZNF141 | zinc finger protein 141 (clone pHZ-44) |
| U78722 | ZNF165 | zinc finger protein 165 |
| HG4333-HT4603 | ZNF79 | zinc finger protein 79 (pT7) |
| X57809 | | lambda light chain variable region |
| HG3111-HT3287 | | *Homo sapiens* clone HH409 unknown |
| U79249 | | Human clone 23839 sequence |
| AB000464 | | clone: RES4-24A |
| HG4593-HT4998 | | voltage-gated sodium channel (SCN1A) |
| X77744 | | *Homo sapiens* for FLJ00032 protein, partial |
| U79248 | | Human clone 23826 sequence |
| AI420129 | | ESTs |

Method of identifying genes regulated by the IL-18 are disclosed in Example 3. These studies showed that IL-18 is a bona fide proinflammatory cytokine and can directly regulate the expression of several genes encoding other proinflammatory mediators. Studies using human blood samples show that many responses to IL-18 occur widely in the human population and demonstrate their utility as biochemical markers of IL-18, and consequently anti-IL18, function.

Modulators of IL-18 can be agonists and antagonist. Preferably the modulator is a binding protein or a neutralizing binding protein.

Exemplary IL-18 inhibitors include, but are not limited to, antibodies, and fragments thereof, that bind to IL-18; antibodies that bind to IL-18R; antibodies that bind to IL-18RAcP; IL-18bp; IL-18R fragments (e.g., a solubilized extracellular domain of the IL-18 receptor); peptides that bind to IL-18 and reduce or prevent its interaction with IL-18R; peptides that bind to IL-18R and reduce or prevent its interaction with IL-18 or with IL-18RAcP; peptides that bind to IL-18RAcP and reduce or prevent its interaction with IL-18R; and small molecules that reduce or prevent IL-18 production or the interaction between any of IL-18, IL-18R, and IL-18RAcP.

Certain IL-18 inhibitors are described, e.g., in U.S. Pat. No. 5,912,324, issued Jul. 14, 1994; EP 0 962 531, published Dec. 8, 1999; EP 712 931, published Nov. 15, 1994; U.S. Pat. No. 5,914,253, issued Jul. 14, 1994; WO 97/24441, published Jul. 10, 1997; U.S. Pat. No. 6,060,283, issued May 9, 2000; EP 850 952, published Dec. 26, 1996; EP 864 585, published Sep. 16, 1998; WO 98/41232, published Sep. 24, 1998; U.S. Pat. No. 6,054,487, issued Apr. 25, 2000; WO 99/09063, published Aug. 14, 1997; WO 99/22760, published Nov. 3, 1997; WO 99/37772, published Jan. 23, 1998; WO 99/37773, published Mar. 20, 1998; EP 0 974 600, published Jan. 26, 2000; WO 00112555, published Mar. 9, 2000; Japanese patent application JP 111, 399194, published Oct. 31, 1997; Israel patent application IL 121554 A0, published Feb. 8, 1998; which are incorporated herein by reference for any purpose.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Production and Characterization of Recombinant IL-18

Example 1.1

Assays to Determine Biological Activity of IL-18

Throughout Example 1 and Example 2 the following assays were used to determine biological activity of IL-18 unless otherwise stated.

Example 1.1A

KG-1 Bioassay

KG-1 (ATCC #CCL-246) is a human myelomonocytic cell line that constitutively expresses low levels of functional IL-18 receptor. Treatment with TNF up-regulates both the IL-18Rα and β subunits of the functional IL-18 receptor on these cells. The KG-1 bioassay was performed by incubating TNF-treated KG-1 cells with recombinant human IL-18 (rhu-IL-18) and determining the level of IL-18-induced human IFNγ production by an ELISA. (Konishi, K., et al (1997) *J. Immunol. Methods* 209:187-191). The KG-1 bioassay was used to determine the neutralization potency of IL-18 antagonists. For example, anti-IL-18 antibodies were incubated with different concentrations of rhu-IL-18 and then incubated with TNF-treated KG-1 cells in a 96-well plate for 16-18 hours at 37° C. The supernatants collected and assayed for human IFNγ levels by an ELISA. This assay can measure IC50 values down to $4 \times 10^{-11}$-$6 \times 10^{-11}$ M of an IL-18 antagonist.

Example 1.1B

Human Whole Blood Assay

Briefly, the Human Whole Blood Assay (WBA) determines neutralization potency of IL-18 antagonists against natural IL-18 within a physiological context. In this assay, the readout was inhibition of endogenous IL-18-dependent human IFNγ production. Whole blood was stimulated with LPS (1 µg/mL) plus IL-12 (50 pg/mL) in the presence or absence of IL-18 antagonists at 37° C. Human IFNγ concentrations were determined by ELISA 18-24 hrs post-LPS plus IL-12 stimulation.

Example 1.1.C

Receptor Binding Assay

Briefly, in the Receptor Binding Assay (RBA), $^{125}$I labeled rhu-IL-18 was used to determine binding of IL-18 to IL-18 receptor. $^{125}$I-rhu-IL-18 binds specifically to the IL-18Rαβ on TNF-treated KG-1 cells (~7,000 sites/cell). $^{125}$I-rhu-IL-18 has the same specific activity as unlabeled IL-18 and can be competed off by unlabeled IL-18.

Two modes of inhibition, A and B, were defined. In neutralization Mode A, binding of IL-18 to the high affinity IL-18 receptor (IL-18Rαβ) was not effected, but IL-18-mediated signal transduction (i.e. IFNγ production) was blocked. In neutralization Mode B binding of IL-18 to IL-18Rαβ was blocked and thereby no subsequent receptor-mediated signaling occurred.

Example 1.2

Production of Recombinant IL-18

Example 1.2.A

Plasmid Construction, Expression and Purification of Human ProIL-18

Recombinant human IL-18 was generated by expressing the precursor form of IL-18 in SF-9 insect cells. Using standard molecular biological methods well known in the art, full-length human pro-IL-18 cDNA was generated using specific PCR primers based on published sequence (Ushio, S., et al. (1996) *J. Immunol.* 156:4274-4279) and subsequently cloned into the baculovirus (BV) transfer vector pVL1393. (BD Biosciences, San Jose, Calif.; Cat# 51-21201P) The 5' PCR primer used to generate full-length human pro-IL-18 cDNA contained sequences encoding a 6-Histidine region such that the N-terminus of the proIL-18 contained a 6-HIS-tag. SF9 insect cells were infected with baculovirus harboring pVL1393 vector containing IL-18 cDNA. Infected SF9 cells were lysed and the lysates were run over a nickel column to purify recombinant HIS-tagged proIL-18 (rhu pro IL-18). (BD Biosciences, San Jose, Calif.; Cat# 554802) The recombinant HIS-tagged proIL-18 was processed further by digesting with human caspase-1 to generate biologically active IL-18 (mature IL-18). (Ghayur T., (1997) *Nature* 386:619-623).

Example 1.2.B

NEM Treatment of IL-18

Recombinant human IL-18 obtained from Hayashibara Biochemical Laboratories, Japan, displayed batch variation in specific activity and in IL-18 binding affinity. IL-18 contained disulphide bonds between various pairs of the four cysteines in mature IL-18. These caused structural and functional heterogeneity, and variations between batches. Homology modeling of human IL-18 using IL-1b coordinates showed that cysteine residues at positions 38 and 68 of mature human IL-18 are exposed and therefore reactive.

Recombinant human IL-18 from Example 1.2.A was treated with N-ethyl maleinamide (NEM) to protect the cysteines from oxidation. NEM-IL-18 was monomeric, did not form aggregates, was stable, and retained high specific activity over time. NEM-IL-18 retained neutralizing epitopes because anti-huIL-18 neutralizing antibodies bound and neutralized NEM-IL-18. Despite NEM treatment of IL-18, neutralizing epitopes on NEM-IL-18 were preserved as determined by the ability of anti-IL-18 antibodies to neutralize biological activity of both NEM-IL-18 and natural human IL-18 in human WBA. NEM-IL-18 was used for assay optimization and selection and initial characterization of fully human anti-human-IL-18 mAbs.

Example 1.2.C

Generation and Characterization of 4C/A Mutant of IL-18

The 4C/A mutant of IL-18 was generated by mutating the four Cysteine residues in mature IL-18 to Alanine ("4C/A-huL-18"). Comparison of 4C/A mutant of IL-18 with NEM-huIL-18, as summarized in Table 4 below, showed that the two proteins were indistinguishable in biological and biochemical properties. Both 4C/A mutant of IL-18 and NEM-huIL-18 were monomeric by dynamic light scattering (DLS) and size exclusion chromatography (SEC) analysis, and similar in conformation and physical stability by circular dichroism analysis. The biological activity of 4C/A mutant of IL-18 and NEM-huIL-18 were the same in the KG-1 assay, and both forms of IL-18 bound IL-18BP and anti-IL-18 antibodies with similar affinity. 4C/A-huL-18 was not subject to oxidative instability and was readily expressed at high levels in *E. coli*.

TABLE 4

Comparison of NEM-IL-18 and 4C/A-huIL-18 shows that they are equivalent in measurements of conformational and oligomeric purity, physical stability, and binding to antibodies or cell-bound receptors.

| Properties | Measurements | NEM-huIL-18 | (4C/A)-huIL-18 |
|---|---|---|---|
| Oligomeric state | SEC | Monomeric | Monomeric |
|  | DLS | Monomeric | Monomeric |
| Confirmation | CD (wavelength scan) | CD minimum at 210 nm | CD minimum at 210 nm |
| Stability | CD (temperature scan) | Stable up to 40° C. | Stable up to 40° C. |
| Bioactivity | IFNγ production by 2 ng/mL IL-18 | 8 ng/mL IFNγ | 8 ng/mL IFNγ |
| Epitopes | Neutralization of IFNγ production by reference binder | Neutralized by IL-18BP-Fc, 125-2H and IL-18Rα | Neutralized by IL-18BP-Fc, 125-2H and IL-18Rα |
|  | Biacore ($K_D$) | IL-18BP-Fc: 0.098 nM<br>125-2H: 0.2 nM<br>2.5(E)mg1: 0.3 nM | IL-18BP-Fc: 0.135 nM<br>125-2H: 0.2 nM<br>2.5(E)mg1: 0.2 nM |

Example 1.2.D

Generation and Characterization of Biotinylated RhuIL-18 (Biot-IL-18)

Biotinylation of NEM-IL-18 from Example 1.2.B was performed on lysine residues using standard techniques well known in the art, (Sulfo-NHS-LC-Biotin, Pierce, Rockford, Ill.; Cat#21335), and the biotinylated rhu-IL-18 (biot-IL-18) obtained was a heterogeneous mixture containing species with 1, 2, 3, or 4 biotins per huIL-18. Furthermore, species with 2 or 3 biotins per rhuIL-18 were the major species in biot-IL-18. Biot-IL-18 was biologically active, bound anti-IL-18 antibodies as determined by ELISA, and was neutralized by all neutralizing anti-huIL-18 antibodies tested. Biot-IL-18 bound KG-1 cells expressing IL-18Rαβ on their surface with high affinity, and the biot-IL-18 on the surface of KG-1 cells was detected by FACS analysis using anti-biotin antibodies (Sigma-Aldrich, St Louis, Mo.; cat# B 3640). Thus biotinylation does not interfere with receptor binding and does not mask neutralizing epitopes of rhuIL-18.

Example 1.2.E

Generation and Characterization of $^{125}$I Labeled RhuIL-18

The lysine residues on NEM-IL-18 from Example 1.2.B were labeled with $^{125}$I using conditions specified by Amersham (Piscataway, N.J.; Cat # IM5861). $^{125}$I-labeled IL-18 retained its specific activity, was competed by non-modified IL-18, and bound specifically to IL-18R on KG-1 cells. Binding of $^{125}$I-labeled IL-18 to IL-18 receptor was blocked by neutralizing anti-huIL-18 monoclonal antibodies. Thus iodination did not affect receptor binding of IL-18 and did not mask neutralizing epitopes on the IL-18. $^{125}$I-labeled IL-18 was used to determine the neutralization mode and potency of anti-IL-18 antibodies in the Receptor Binding Assay.

Example 2

Generation and Isolation of Anti IL-18 Antibodies

Example 2.1

Assays to Identify Anti-IL-18 Antibodies

Throughout Example 3 the following assays were used to identify and characterize anti-IL-18 antibodies unless otherwise stated.

Example 2.1.A

ELISA

An ELISA was developed to screen for antibodies that bind human IL-18. In this ELISA, biotinylated NEM-huIL-18 (see Example 1.2.B) was captured by either goat anti-biotinylated IgG or on to streptavidin coated plates. Hybridoma or B cell supernatants were applied and IL-18-bound antibodies were detected using HRP-conjugated anti-human IgGs, following standard ELISA protocols well known in the art.

Example 2.1.B

Affinity Determinations Using BIACORE Technology

The BIACORE assay (Biacore, Inc, Piscataway, N.J.) determines the affinity of antibodies with kinetic measurements of on-, off-rate constants. Antibodies are captured on a biosensor chip by means of a covalently linked secondary antibody (e.g. goat anti-human IgG or anti-mouse IgG) and then varying concentrations of recombinant IL-18 are applied. Binding is recorded as a function of time and kinetic rate constants are calculated. In this assay, on-rates as fast as $10^6$ $M^{-1}$ $s^{-1}$ and off-rates as slow as $10^{-6}$ $s^{-1}$ can be measured.

Example 2.1.C

Epitope Mapping

BIACORE technology was used for mapping the epitopes recognized by IL-18 antagonists such as anti-IL-18 antibodies. Briefly, one IL-18 antagonist was captured on the Biacore chip and rhuIL-18 was bound to the immobilized reagent. Binding of another anti-IL-18 antagonist to this complex was then tested. Simultaneous binding of two reagents demonstrates that the two recognize distinct epitopes.

Example 2.2

Generation of Anti-IL-18 HuMAbs Using XENOMOUSE

The XENOMOUSE transgenic mouse technology (Abgenix, Inc., Fremont, Calif.) was employed to obtain fully human anti-human IL-18 monoclonal antibodies (HuMAbs). This technology consists of transgenic mice carrying human variable heavy chain locus carrying VH, DH, and JH, Cmu, Cdelta and a single human IgG constant heavy chain locus and light chain gene loci. Upon immunization with an antigen of interest, these mice generate fully human antibodies to the antigen.

Example 2.2.A

Immunization of XENOMOUSE with IL-18 Antigen

XENOMOUSE animals were immunized via footpad route for all injections. Total volume of each injection was 50 ul per mouse, 25 ul per footpad. Initial immunization injection contained 40 ug human IL-18 (NEM-rhuIL-18) in pyrogen-free DPBS admixed 1:1 v/v with TiterMax Gold per mouse. Subsequent boosts were made with 40 ug Human IL-18 in pyrogen free DPBS admixed with 25 ug of Adju-Phos (aluminum phosphate gel) per mouse for six times, then a final boost of 40 ug Human IL-18 in pyrogen free DPBS without adjuvant per mouse. The animals were immunized on days 0, 4, 8, 11, 17, 21, 25 and 35 for this protocol. Fusions were performed on day 39. Following the immunization regimen described above, mice were euthanized, then inguinal and Lumbar lymph nodes were recovered.

Example 2.2.B

Generation of Hybridoma

Lymphocytes were released by mechanical disruption of the inguinal and Lumbar lymph nodes, obtained according to Example 2.2.A, using a tissue grinder, and depleted of T cells by CD90 negative selection. Hybridoma fusion was performed by mixing washed enriched B cells and non-secretory myeloma P3X63Ag8.653 cells purchased from ATCC, cat. # CRL 1580 (Kearney et al, J. Immunol. 123, 1979, 1548-1550) at a ratio of 1:1. The cell mixture was gently pelleted by centrifugation at 800 g. After complete removal of the supernatant, the cells were treated with 24 mL of Pronase solution (CalBiochem, San Diego, Calif.; cat. # 53702; 0.5 mg/ml in PBS) for no more than 2 minutes. Then 3-5 ml of FBS was added to stop the enzyme activity and the suspension was adjusted to 40 ml total volume using electro cell fusion solution, ECFS (0.3 M Sucrose, Sigma-Aldrich, St Louis, Mo.; Cat# S7903, 0.1 mM Magnesium Acetate, Sigma, Cat# M2545, 0.1 mM Calcium Acetate, Sigma-Aldrich, St Louis, Mo.; Cat# C4705). The supernatant was removed after centrifugation and the cells were resuspended in 40 ml ECFS. This wash step was repeated and the cells again were resuspended in ECFS to a concentration of $2 \times 10^6$ cells/ml. Electro-cell fusion was performed using a fusion generator, model ECM2001, Genetronic, Inc., San Diego, Calif. The fusion chamber size used was 2.0 ml using the following instrument settings: Alignment condition: voltage: 50 v, time: 50 s; Membrane breaking at: voltage: 3000 v, time: 30 μs; Post-fusion holding time: 3 s.

After fusion, the cells were resuspended in hybridoma fusion medium: DMEM (JRH Biosciences), 15% FBS (Hyclone), containing 0.5XHA (Sigma-Aldrich, St Louis, Mo.; cat. # A9666), and supplemented with L-glutamine, pen/strep, OPI (oxaloacetate, pyruvate, bovine insulin) (all from Sigma) and IL-6 (Boehringer Mannheim, Indianapolis, Ind.) for culture at 37° C. and 10% $CO^2$ in air. Cells were plated in flat bottomed 96-well tissue culture plates at $4 \times 10^4$ cells per well. Cultures were maintained in hybridoma fusion medium for 2 weeks before transfer to Hybridoma medium: DMEM (JRH Biosciences, Lenexa, Kans.), 15% FBS (Hyclone, Logan, Utah), and supplemented with L-glutamine, pen/strep, OPI (oxaloacetate, pyruvate, bovine insulin) (all from Sigma) and IL-6 (Boehringer Mannheim, Indianapolis, Ind.). Hybridomas were selected for by survival in 0.5XHA hybridoma fusion medium and supernatants from those wells containing hybridomas were screened for antigen reactivity by ELISA. The ELISA format entailed incubating supernatants on antigen coated plates (human IL-18 coated plates) and detecting human anti-human IL-18 binding antibodies using horseradish peroxidase (HRP) labeled mouse anti-human IgG, then the all positive samples were confirmed by two sets of ELISA in parallel, which entailed incubating supernatants on antigen coated plates (human IL-18 coated plates) and detecting human anti-Human IL-18 binding antibodies using horseradish peroxidase (HRP) labeled mouse anti-human Gamma and Kappa chain.

Cloning was performed on selected antigen-positive wells using limited dilution plating. Plates were visually inspected for the presence of single colony growth and supernatants from single colony wells then screened by antigen-specific ELISAs as described above. Highly reactive clones were assayed to verify purity of human gamma and kappa chain by multiplex ELISA using a Luminex instrument.

Example 2.2.C

XENOMAX Technology

Alternatively, lymphocytes obtained in Example 2.2.B were subjected to Selective Lymphocyte Antibody-generation Method (SLAM), which defines XENOMAX antibody selection technology (Abgenix, Inc., Fremont, Calif.). Single B cells were plated in 96 well plates B cells producing human monoclonal antibodies to desired antigen (human IL-18) were identified by a plaque forming cell assay (Babcook, J. S., Leslie, K. B., Olsen, O. A., Salmon, R. A., and Schrader, J. W. Isolation of functional antibody genes from single lymphocytes of defined antigen-specificity. *Proc. Natl. Acad. Sci. USA*, 93:7843-7848, 1996) and IgG genes were cloned by single-cell RT-PCR of isolated B cells using 5' primers for VH and Vk leader sequences and 3' primers specific for human Cgamma and Ckappa. The recombinant IgG genes obtained were expressed in mammalian cells as described in Examples 2.2.E and 2.2.G.

Example 2.2.D

Identification of Anti-IL-18 Antibodies

Hybridomas and B-cell producing antibodies that bound IL-18, generated according to Examples 2.2.B and 2.2.C, were identified using biotinylated IL-18 ELISA (see Example 2.1.A). Hybridomas and B-cell supernatants containing antibodies that bound IL-18 were then tested for IL-18 neutralization potency in the KG-1 bioassay performed according to Example 1.1.A. Neutralizing anti-IL-18 antibodies (from hybridoma and SLAM approaches) were subcloned into a mammalian expression vector, expressed in COS cells, purified and re-tested in the KG-1 bioassay (see Table 5).

TABLE 5

Neutralization Potency of Anti-IL-18 HuMAbs in KG-1 Bioassay

| HuMAb# | KG-1 Assays (IC$_{50}$, M) |
|---|---|
| | NEM-rhuIL-18 |
| Hybridoma | |
| 2.5.1 | 3E−10; 4E−10 |
| 2.13.1 | 2E−10; 1E−10; 7E−11 |
| 2.3.3 | 1E−9; 2E−10; 7E−10 |
| XENOMAX | |
| 215 | 1E−10; 3E−10; 1E−10; |
| 444 | 1E−10; 2E−10; 2E−10 |
| 478 | 7E−10; 2E−9; 3E−10 |
| 435 | 8E−10; 7E−10; 4E−10; |
| 413 | 1E−9; 7E−10; 7E−10 |
| 581 | 7E−10; 3E−10; 3E−9 |
| 231 | 1E−10; 3E−11; 2E−9 |
| 521 | 6E−10; 3E−10; 2E−9 |
| 336 | 7E−10 |
| 351 | 2E−10 |
| 490 | 5E−10 |
| 550 | TBD |
| 268 | 7E−9 |

The variable regions of the antibodies in Table 5 are described in Table 1

Example 2.2.E

Subloning of Neutralizing Anti-IL-18 HuMAbs into Mammalian Expression Vector

Genes for the heavy and light chains of antibodies were cloned in pCDNA (Invitrogen, Carlsbad, Calif.) vectors under control of the CMV promoter following manufacturer's instruction. These plasmids with human genomic Gamma-2 and kappa sequences were used to cotransfect COS cells by electroporation with heavy and light chains corresponding to each clone employing standard conditions well known in the art.

Cells were allowed to recover, grow, and secrete antibodies for 72 hours in serum free DMEM supplemented with glutamine. Culture supernatants were then collected, clarified by centrifugation and filtration, and put over Protein-A resin. Columns were washed with PBS, antibodies eluted with low pH buffer, and quickly neutralized with 1 M Tris solution. Antibody preps were buffer-exchanged with PBS on Amicon-30 spin filters. Concentration and purity of antibodies were analyzed by spectrometry at OD 280 and SDS-PAGE before they were tested for IL-18 neutralization potency.

To achieve greater expression levels of human antibodies in COS cells, the heavy and light chains of some antibodies were subcloned into vector pEF-BOS (Mizushima, S. and Nagata, S. (1990) Nucleic acids Research Vol 18, No. 17) under control of elongation factor promoter.

In short, PCR primers for heavy chain variable regions were designed in such a way that they could be inserted into a cassette pEF-BOS plasmid containing an IgG signal peptide and the sequence of human IgG1 constant region [wild type (SEQ ID No. 2) or inactive mutant (SEQ ID No. 3)]. The forward $V_H$ PCR primer contained restriction site NruI, as did the nucleotide sequence of the signal peptide. The reverse $V_H$ PCR primer contained SalI restriction site that was also engineered into the 5' end of the gamma-1 Fc sequence. The $V_H$ PCR fragments were digested with NruI/SalI and cloned into the pEF-BOS human IgG1 wild type or pEF-BOS human IgG1 mutant constructs. The entire light chain genes were moved into pEF-BOS vector in their existing Kappa format from pCDNA vectors by HindIII restriction digest, filling the overhangs with T4 polymerase, followed by NotI digest. These blunt/NotI light chain fragments were then cloned into SrfI/NotI digested pEF-BOS vector.

$V_H$ and $V_L$ regions of antibodies were cloned from original hybridoma lines. RNA was prepared from antibody-producing cells, RT-PCR performed with primers designed as described above, i.e NruI/SalI primers for $V_H$, and NruI/BsiWI primers for $V_L$. The full length IgG1 and Kappa chains were assembled into cassette vectors.

The selected antibodies were further modified. Naturally occurring antibodies have either glutamine (Q) or glutamate (E) as the heavy and/or light chain NH2-terminus. Production of antibodies with Q as the NH2-terminus yields NH2-terminal heterogenity due to the cyclization of the glutamine residue to a glutamate. Therefore, the glutamine residue at the NH2-terminus of some of the antibodies was mutated to glutamate. Also two residues, Leucine234 and Leucine235 in the hinge region of the Fc portion, were mutated to prevent the effector functions of the antibody. Briefly, Leucine 234 and Leucine 235 were each replaced by an Alanine residue using standard molecular biological techniques (Lund, J. et al., *J. Immunology* (1991)147: 2657-2662; Winter, et al. U.S. Pat. Nos. 5,648,260; 5,624,821; 5,624,821). These Fc-mutated antibodies were termed (mg1). These mutants are further characterized in Examples 2.2.J 6, below.

Example 2.2.F

Characterization of Selected Neutralizing Anti-IL-18 Antibodies

Several recombinant anti-human IL-18 antibodies with distinct germ line sequences were produced in mammalian cells, purified and functionally characterized in various assays (see Table 6).

TABLE 6

In vitro antigen binding, cell assay and backbone sequence characteristics of some anti-IL-18 antibodies.

| Antibody | Technology[a] | Biacore[b] ($K_D$, nM) | RBA (IC$_{50}$, nM) | KG-1[b] (IC$_{50}$, nM) | WBA (IC$_{50}$, nM) | Gene Families[c] Sequence Diversity | |
|---|---|---|---|---|---|---|---|
| 2.5(E)mg1 | Hybridoma | 0.31 | 2.38 | 0.20 | 3 | VL-L2 | VH5-51 |
| 2.5(E)wtg1 | Hybridoma | 0.40 | 2.38 | 0.30 | 3 | VL-L2 | VH5-51 |
| 215(E)mg1[d] | Xenomax | 0.23 | 1.17 | 0.17 | 3 | VL-A27 | VH4-31 |
| 444(Q)mg1[d] | Xenomax | 1.61 | 2.49 | 0.13 | 1 | VL-A27(7) | VH4-31(1) |
| 581(E)mg1[d] | Xenomax | 2.00 | 1.28 | 1.3 | 3 | VL-A2 | VH3-30 |

TABLE 6-continued

In vitro antigen binding, cell assay and backbone sequence characteristics of some anti-IL-18 antibodies.

| Antibody | Technology[a] | Biacore[b] ($K_D$, nM) | RBA ($IC_{50}$, nM) | KG-1[b] ($IC_{50}$, nM) | WBA ($IC_{50}$, nM) | Gene Families[c] Sequence Diversity | |
|---|---|---|---|---|---|---|---|
| 2.3.1(E)wtg1 | Hybridoma | 0.23 | 0.20 | 0.63 | 2 | VL-02 | VH4-59 |
| 2.13.1(E)wtg1 | Hybridoma | 0.20 | 0.20 | 0.12 | 2 | VL-A27(8) | VH4-31(18) |

NEM-cys protected rhuIL-18 was used.
Numbers in parenthesis indicate differences in amino acids from clone closet to germ line sequence Example 2.2.G Generation of CHO Cell Line Producing 2.5(E)mg1

Stable CHO cell lines expressing 2.5 (E)mg1 antibody were generated following the procedures outlined below.

Example 2.2.G 1

Construction of Expression Vector

The plasmid pA510 was constructed for high-level expression of antibodies in mammalian cell lines. This pUC19-derived plasmid contained the *E. coli* ColE1 origin of replication and the beta-lactamase gene for ampicillin resistance.

Briefly, cDNA corresponding to the VH and VL regions of the 2.5(E)mg1 antibody were cloned using standard molecular biological techniques, fused to mutated human gamma-1 and kappa constant region genes, respectively, such that DNA encoding a native, fully-human, IgG1/kappa antibody was produced. These DNAs were introduced into expression construct pA510. The resulting plasmid contained sequences (exclusive of pUC19) for the following genes or regulatory elements in the following order: 5'-CMV enhancer, adenovirus major late promoter, human immunoglobulin signal peptide, 2.5(E)mg1 heavy-chain immunoglobulin variable region, human gamma-1 immunoglobulin constant region, SV40 polyadenylation sequence, human gastrin transcription termination sequence, SV40 origin of replication (SV40 promoter/enhancer), murine dihydrofolate reductase sequence, thymidine kinase polyadenylation sequence from Herpes Simplex virus, CMV enhancer, adenovirus major late promoter, human immunoglobulin signal peptide, 2.5(E)mg1 light-chain immunoglobulin variable region, human immunoglobulin kappa constant region, and SV40 polyadenylation sequence-3'. The coding regions were inserted downstream from strong viral promoters that drove the antibody gene transcription. The vector also encoded the expression of the mouse DHFR gene, which enabled selection of transformed cells by virtue their ability to grow in culture in the absence of nucleosides.

Example 2.2.G 2

Transfection of Expression Vector into Parental Cell Line

The cell line, CHO DUX B11. (Urlaub, G. and Chasin L. A. *Proc Natl Acad Sci USA* 77: 4216-4220 (1980)), defective in the expression of the dihydrofolate reductase (DHFR) gene, was used for transfection of the expression vector described in Example 2.2.G 1. CHO DUX B11 cells were transfected with the vector using calcium phosphate precipitation method well known in the art (Current Protocols in Molecular Biology; Ausubel, F. V., Brent, R., Moore, D. M., Kingston, R. E., Seidman, J. G., Smith, J. A., and K. Struhl eds; Wiley Interscience, N.Y., N.Y. (1990)) with the following modifications. The plates were aspirated and 9 ml of F12 medium was added to each plate. The plates were incubated at 37° C. for two hours. One hundred and fifty micrograms of DNA were dissolved in 2.7 ml water in a 50 ml conical tube. Three hundred microliters of 2.5 M CaCl2 was added and this DNA mix was added one drop at a time to 3 ml of 2× Hepes buffered saline (HeBS) in a 50 ml conical tube.

The resulting mixture was vortexed for 5 seconds and incubated at room temperature for 20 minutes. One ml was distributed evenly over each plate (still in F12) and the plates were incubated at 37° C. for four hours. After incubation, the plates were aspirated, and 2 ml of 10% DMSO in F12 was added to each plate. The DMSO shock continued for one minute after which the DMSO was diluted by the addition of 5 ml of phosphate buffered saline (PBS) to each plate. The plates were aspirated and washed two more times in PBS. Ten ml of Gibco alpha MEM with nucleosides was added and the plates were incubated at 37° C. overnight. The next day, the medium was changed to Gibco alpha MEM without nucleosides with 5% dialyzed fetal bovine serum (FBS), and six hours later the cells were seeded into 96-well plates as follows. The cells from the 10 cm plates were harvested using trypsin digestion and resuspended in a total of 300 ml of Gibco alpha MEM without nucleosides with 5% serum. Twenty, 96-well plates were seeded at 10 ml/plate, 100 l/well. One hundred ml of the same medium was added to the remaining 100 ml of cells and 20 additional 96-well plates were seeded as above. (This was a second dilution.) The medium was changed in the 96-well plates one week later and again a week after that. The alpha MEM medium without nucleosides was used to select cells expressing DHFR and therefore the expression vector.

Example 2.2.G 3

Selection of 2.5(E)mg1 Producing Cells

Culture supernatants from transfected CHO cells were tested for the presence of secreted antibody 2.5(E)mg1 using an ELISA specific for human IgG. Once a set of CHO transfectants had been screened for expression of human antibody, an additional selection was used to isolate those cells that had amplified the number of copies of the expression vector integrated in the CHO genome. The drug methotrexate (MTX) was used for the selection of amplified lines. Cultures grown in the presence of MTX were tested for their ability to produce immunoglobulin. The MTX-resistant lines that expressed more antibody than their MTX-sensitive predecessors were taken through another cycle of selection in higher concentration MTX, and tested for immunoglobulin production. 2.5(E)mg1 expressing CHO cells were cultured in a 1 or 15 liter bioreactor and the yield of antibody was determined to be ~1.0 g/L in a two-week run.

Example 2.2.H

Physicochemical Characterization of CHO Cell-Derived 2.5(E)mg1

Preliminary physical and chemical characterization of CHO derived 2.5(E)mg1 was performed. The experimentally determined molecular weight of 2.5(E)mg1 was approximately 149 kDa, in good agreement with the theoretical molecular weight. Using Peptide mapping techniques (K Biemann Annu. Rev. Biochem. 1992 61 977-1010; D A. Lewis Accelerated Articles, Anal. Chem. 1994, 66, 585-595) it was confirmed that 2.5(E)mg1 had the correct N-termini for both light and heavy chains. There was very little heavy chain C terminal variability, as 99% of the 2.5(E)mg1 molecules lacked lysine at the heavy chain carboxy termini. Each 2.5(E)mg1 heavy chain contained a single N-linked glycosylation site with oligomannose and complex, fucosylated binatennary structures with 0, 1 or 2 terminal galactose residues.

Example 2.2.I

Solubility and Stability of CHO Cell-Derived 2.5(E)mg1

Purified 2.5(E)mg1 was soluble to at least 62 mg/mL in pH 5, 6 and 7 buffers for a minimum of 4 weeks. Accelerated stability studies with 2.5(E)mg1 at 37° C. in these buffers were performed to identify stability-indicating assays and the optimal long-term storage pH. Samples were taken at weekly intervals for analysis by size exclusion HPLC and SDS-PAGE to test for aggregation and fragmentation, LC-MS/MS peptide mapping for S—S bond detection, antigen-ELISA and/or cell based bioassay for activity measurement, and cation exchange HPLC and iso-Asp quantification for charge heterogeneity measurement. Preliminary analysis of the samples by SEC (size exclusion chromatography), SDS-PAGE and cation-exchange chromatography showed that all three assays indicated stability and therefore 2.5(E)mg1 is more stable at ~pH6.

Example 2.2.J

Characterization of CHO-Cell-Derived Anti-IL-18 HuMAb, 2.5(E)mg1

Example 2.2.J 1

IL-18 Species Specificity

The ability of 2.5(E)mg1 to bind and/or neutralize IL-18 from human, cynomolgus monkey, mouse, rat and dog was evaluated. Using the BIACORE assay following manufacturers instructions (see Example 2.1.B), it was shown that 2.5(E)mg1 bound mature human IL-18, but not mouse IL-18. In addition, immunoprecipitation data showed that 2.5(E)mg1 bound cynomolgus monkey IL-18 (IC50 for cyno IL-18=9.1E×10$^{-11}$), but not dog or rat IL-18. 2.5(E)mg1 functionally neutralized human and cynomolgus IL-18 bioactivity in a similar manner, but no inhibition of dog, rat or mouse IL-18 was seen.

Example 2.2.J 2

Human Cytokine Specificity

The specificity of 2.5(E)mg1 for IL-18 was evaluated using the BIACORE assay following manufacturers instructions (see Example 2.1.B). The 2.5(E)mg1 antibody was captured on the biosensor chip and its ability to bind a panel of known human cytokines in solution was determined. As shown in Table 7, 2.5(E)mg1 bound recombinant human mature IL-18 and pro-IL-18. In contrast, 2.5(E)mg1 did not bind to any of the other 23 human cytokines tested, including the IL-1 family members IL-1α and IL-1β.

TABLE 7

Biacore Analysis of Cytokine Binding by 2.5(E)mg1

| Soluble rec. human cytokines, (1 μM) | Captured 2.5(E)mg1 (25 mg/mL) 2.5(E)mg1 Binding |
|---|---|
| IFNγ | − |
| IL-1α | − |
| IL-1β | − |
| Other cytokines[a] | − |
| IL-18[b] | + |
| Pro-IL-18 | + |

[a]Additional cytokines tested for binding included IL-2, IL-3, IL-4, IL-5, IL-6, IL-7, IL-8, IL-9, IL-10, IL-11, IL-12, IL-13, IL-15, IL-16, IL-17, IL-21, TNF, LT, LTα1β2, and LTα2β1. 2.5(E)mg1 did not bind to any of these cytokines.
[b]Cysteine > Alanine mutant BV derived rec. human IL-18

Example 2.2.J 3

Affinity Measurements

Table 8 shows the in vitro IL-18 binding properties of 2.5(E)mg1 measured using the BIACORe assay according to manufacturer's instruction. The 2.5(E)mg1 antibody had a fast on-rate, slow off-rate with an overall affinity of 0.196 nM. The kinetic rate parameters of two reference IL-18 antagonists (125-2H and IL-18 binding protein) are shown for comparison.

TABLE 8

IL-18 Binding Properties of 2.5(E)mg1 and Reference Reagents

| | Biacore Parameters | | |
|---|---|---|---|
| Reagent | On-rate (×10$^3$ M$^{-1}$s$^{-1}$) | Off-rate (×10$^{-6}$ s$^{-1}$) | K$_D$ (nM) |
| 2.5(E)mg1[a] | 268 | 52.4 | 0.196 |
| Murine anti-human IL-18 (125-2H)[b] | 190 | 110 | 0.550 |
| IL-18BP-Fc[c] | 140 | 26 | 0.190 |

[a](4C/A)-HuIL-18 was tested in BIACORE.
[b]125-2H, a neutralizing mouse anti-human IL-18 IgG1 mAb
[c]IL-18BP-Fc, an Fc fusion of the natural IL-18 antagonist

Example 2.2.J 4

In Vitro IL-18 Neutralization Potency

The in vitro neutralization potency of 2.5(E)mg1 was determined in the KG-1 bioassay, the receptor binding assay (RBA) and the human WBA (see Examples 1.1.A-1.1.C). As shown in Table 8 the 2.5(E)mg1 antibody neutralized both recombinant (KG-1 and RBA) and natural IL-18 (WBA), ($IC_{50}$<0.5 nM in KG-1, <2 nM in RBA and <5 nM in WBA), and is consistent with its IL-18 binding affinity.

TABLE 8

Neutralization Potencies of 2.5(E)mg1 and Reference Reagents

| Reagent | Neutralization Potency in vitro (IC50, nM) | | |
|---|---|---|---|
| | KG-1[a] | RBA[b] | WBA[c] |
| 2.5(E)mg1 | 0.2 | 2.4 | 3.0 |
| Murine anti-human IL-18 mAb(125-2H) | 0.2 | >300[d] | 3.0 |
| IL-18BP-Fc | 0.03 | 1.0 | 5.7 |
| Anti-IL-18R mAb (M-840) | 1.5 | 1.7 | 2.7 |

[b]KG-1 bioassay, mean values
[c](4C/A)-huIL-18 was used in this assay
[d]Receptor Binding Assay Human Whole blood assay with 4-6 individual donors. Mean values given.

125-2H neutralizes IL-18 bioactivity despite failure to inhibit receptor binding Example 2.2.J 5

In Vivo Neutralization Potency of 2.5(E)mg1

To evaluate the ability of 2.5(E)mg1 to neutralize natural human IL-18-induced IFNγ in an inflammatory environment in vivo, the severe combined immunodeficient (SCID) mouse model was used, wherein human PBMCs were injected into the mouse and the cells were stimulated in vivo to produce human IL-18 (HuPBMC-SCID model). The results (Table 9) showed that 2.5(E)mg1 inhibited human IL-18-dependent human IFNγ production in vivo with a clear dose-response by either route of administration. The $ED_{50}$ of 2.5(E)mg1 was approximately 1 μg or 0.1 μg/per mouse (=0.05 mg/kg or 0.005 mg/kg) by ip or iv administration, respectively.

TABLE 9A

In vivo efficacy of 2.5(E)mg1 administered i.p. in HuPBMC-SCID mouse model

| Group | huIFNg (pg/ml) | % Inhibition |
|---|---|---|
| 2.5(E)mg1 0.025 μg/mouse | 70 ± 17 | 61 |
| 2.5(E)mg1 0.25 μg/mouse | 112 ± 29 | 36 |
| 2.5(E)mg1 2.5 μg/mouse | 36 ± 10 | 80 |
| 2.5(E)mg1 25 μg/mouse | 10 ± 8 | 94 |
| 2.5(E)mg1 250 μg/mouse | 3 ± 2 | 98 |
| No Treatment | 193 ± 59 | |
| HuIgG Control 250 μg/mouse | 177 ± 33 | |

TABLE 9B

In vivo efficacy of 2.5(E)mg1 administered i.v. in HuPBMC-SCID mouse model

| Group | huIFNg (pg/ml) | % Inhibition |
|---|---|---|
| 2.5(E)mg1 0.025 μg/mouse | 156 ± 45 | 36 |
| 2.5(E)mg1 0.25 μg/mouse | 27 ± 9 | 89 |
| 2.5(E)mg1 2.5 μg/mouse | 36 ± 8 | 85 |
| 2.5(E)mg1 25 μg/mouse | 11 ± 6 | 96 |
| 2.5(E)mg1 250 μg/mouse | 4 ± 2 | 98 |
| No Treatment | 279 ± 26 | |
| HuIgG Control 250 μg/mouse | 245 ± 22 | |

Example 2.2.J 6

Effector Functions

The Fc portion of an antibody mediates several important effector functions e.g. cytokine induction, antibody-dependent cell-mediated cytotoxicity (ADCC), phagocytosis, complement dependent cytotoxicity (CDC), and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies The L234A and L235A mutations in 2.5(E)mg1 did not influence the overall affinity or the neutralization potency of 2.5(E)mg1 HuMAb as compared with 2.5(E)wtg1 (Table 10). However, as expected, these mutations did abolish binding to FcγR and C1q.

TABLE 10

Mutations of residues L234 and L235 to Alanine does not affect affinity or neutralization potency of 2.5(E)mg1

| Ab | Kinetic Rate Parameters | | | KG-1 Bioassay |
|---|---|---|---|---|
| | On-rate ($10^3 M^{-1} s^{-1}$) | Off-rate ($\times 10^{-6} s^{-1}$) | $K_D$ (nM) | $IC_{50}$ (nM) |
| 2.5(E)wtg1 | 281 | 47.8 | 0.170 | 0.4 |
| 2.5(E)mg1 | 268 | 52.4 | 0.196 | 0.2 |

Example 2.2.J 6.1

FcγR I Binding

The human FcγR I (CD64) has a relatively high affinity for IgG1 immune complexes ($K_D$ 1E-8~1E-9 M). It is expressed on monocytes and macrophages and a number of myeloid cell lines including U937. The binding of 2.5(E)wtg1 and 2.5(E)mg1 to U937 cells was determined by fluorescence-activated cell sorting (FACS) (CURRENT PROTOCOLS IN IMMUNOLOGY. Vol (1) 5.3.1, Edited by J. E. Coligan et. al., Published by John Wiley & Sons, Inc., 2002). The data obtained (see Table 11) demonstrated that 2.5(E)wtg1 binds to U937 cells, but as expected, 2.5(E)mg1 did not. To confirm that this binding was mediated through FcγR I, a mouse anti-hFcγR I blocking antibody (10.1) was used for competition experiments. The result showed that antibody 10.1 blocked binding of 2.5(E)wtg1 to U937 cells in a dose-dependent manner at the concentrations tested below, and thus, 2.5(E)wtg1 binds FcγR I on U937 cells.

TABLE 11

Demonstration of the failure of 2.5(E)mg1, in contrast to 2.5(E)wtg1, to bind FcγR I on U937 cells (data shown as MFI +/− SD)

| Antibody Conc (μM) | 1.00E−09 | 1.00E−08 | 1.00E−07 | 1.00E−06 | 1.00E−05 | 1.00E−04 | 1.00E−03 | 1.00E−02 | 1.00E−01 |
|---|---|---|---|---|---|---|---|---|---|
| 2.5(E)wtg1 | 0.50 + 0.00 | 0.50 + 0.00 | 0.63 + 0.12 | 0.57 + 0.05 | 0.60 + 0.00 | 1.10 + 0.00 | 5.80 + 0.05 | 29.60 + 0.05 | 38.76 + 5.19 |
| 2.5(E)mg1 | 0.67 + 0.09 | 0.67 + 0.09 | 0.60 + 0.00 | 0.80 + 0.14 | 0.63 + 0.05 | 0.67 + 0.05 | 0.53 + 0.05 | 0.60 + 0.05 | 0.63 + 0.08 |

Example 2.2.J 6.2

FcγR II Binding

The human FcγR II (CD32) has a relatively low binding affinity for IgG1 immune complexes ($K_D$ 1E-5~1E-7 M). Under physiological conditions, it requires the formation of multivalent immune complexes for activation. Using fluorescein isothiocyanate (FITC) labeled antibodies specific for FcγR I, II or III and detection by flow cytometry, we validated the expression of FcγR II on K562 cells and used this cell line for the FcγR II binding assay. The binding of monomeric 2.5(E)wtg1 to K562 cells was very weak. Therefore, an anti-kappa chain antibody was used to pre-crosslink the IgG1 molecules to mimic multivalent immune complexes and tested their binding to FcγR II on K562 cells. After cross-linking, 2.5(E)wtg1 bound to K562 cells, but even after cross-linking 2.5(E)mg1 showed only minimal, if any, binding (Table 12). An anti-FcγR II antibody, clone IV3, blocked binding of 2.5(E)wtg1, and thus, the 2.5(E)wtg1 binding to K562 was FcγR II mediated.

Example 2.2.J 6.4

Neonatal Fc Receptor (FcRn) Binding

Interaction of IgG with the neonatal Fc receptor (also called Bramble receptor) in endothelial cells has been proposed to be an IgG quality control system and the critical determinant for the long half-life of IgGs [Ghetie, V., et al (1997) Nat. Biotechnol. 15:637-640]. IgG molecules taken up by pinocytosis and binding successfully to FcRn in endocytic vacuoles are returned to circulation. IgG molecules that fail to bind to FcRn are degraded.

The critical residues of human IgG for FcRn binding have been mapped to the junction of the CH2-CH3 domains (Kim J. K., et al (1999) Eur. J. Immunol. 29:2819-2825). Importantly, these FcRn binding residues are conserved between human and mouse immunoglobulins and human immunoglobulins bind to mouse FcRn allowing structure activity relationship studies in mice.

TABLE 12

Binding of 2.5(E)wtg1 and 2.5(E)mg1 to FcγR II on K562 cells after crosslinking (data shown as MFI +/− SD)

| Antibody Conc (μM) | 1.00E−08 | 1.00E−07 | 1.00E−06 | 1.00E−05 | 1.00E−04 | 1.00E−03 | 1.00E−02 | 1.00E−01 | 1.00E+00 |
|---|---|---|---|---|---|---|---|---|---|
| 2.5(E)wtg1 | 0.37 + 0.05 | 0.37 + 0.05 | 0.40 + 0.00 | 0.43 + 0.05 | 0.80 + 0.08 | 3.43 + 0.21 | 19.7 + 0.70 | 93.33 + 4.90 | 134.37 + 12.93 |
| 2.5(E)mg1 | 0.30 + 0.00 | 0.40 + 0.00 | 0.40 + 0.00 | 0.37 + 0.05 | 0.37 + 0.05 | 0.40 + 0.00 | 0.50 + 0.00 | 1.60 + 0.08 | 5.37 + 0.38 |

Example 2.2.J 6.3

C1q Binding

Complement activation and lysis of the cells via the classic pathway is activated through binding of C1q to the Fc portion of IgG molecule. The binding of C1q to 2.5(E)wtg1 and 2.5(E)mg1 was determined using standard ELISA techniques known in the art (Hezareh, M., et. al., (2001) *J. Virology*, 75(24):12161-12168). 2.5(E)wtg1 and 2.5(E)mg1 HuMAbs were coated onto plastic plates followed by incubation with human C1q. Bound C1q molecules were then detected by a mixture of goat-anti-human C1q and rabbit anti-goat IgG alkaline phosphate conjugate. The results showed that 2.5(E)wtg1 bound C1q, but the 2.5(E)mg1 did not (Table 13).

To test the effect of the L234A and L235A mutations on FcRn binding, binding of the wild-type 2.5(E)wtg1 and the mutant 2.5(E)mg1 to FcRn in vitro was determined using a FcRn expressing CHO cell line. 2.5(E)wtg1 and 2.5(E)mg1 were incubated with the FcRn expressing CHO cells at pH 6.5, followed by incubation with FITC-conjugated anti-human IgG (2° Ab). The cells were washed and analyzed by FACS.

The 500 nM concentration of 2.5(E)mg1 and 2.5(E)wtg1 showed significant binding to the FcRn compared to the 0.5 nM concentration, which was similar to background with cells alone.

TABLE 13

Demonstration of the failure of 2.5(E)mg1, in contrast to 2.5(E)wtg1, to bind to C1q by ELISA (data shown as $OD_{405}$ +/− SD)

| C1q Conc (μg/ml) | 0 | 20 | 40 | 60 | 80 | 100 | 120 |
|---|---|---|---|---|---|---|---|
| 2.5(E)wtg1 | 0.09 + 0.00 | 0.78 + 0.00 | 0.98 + 0.00 | 1.06 + 0.07 | 1.14 + 0.06 | 1.32 + 0.13 | 1.24 + 0.06 |
| 2.5(E)mg1 | 0.10 + 0.01 | 0.12 + 0.00 | 0.16 + 0.00 | 0.18 + 0.00 | 0.21 + 0.01 | 0.21 + 0.01 | 0.22 + 0.00 |

Example 2.2.K

Pharmacokinetics in Mice

Pharmacokinetics (PK) of 2.5(E)mg1 were assessed in a screening mouse study to determine if the Fc mutations (L234A, L235A) introduced to prevent binding of 2.5(E)mg1 to FcγR and C1q adversely affected the serum PK profile. The mouse FcRn bound mouse and human IgG equally well making the mouse a relevant species for structure activity relationship studies in mice (Ober, R. J., et al (2001) Int. Immunol. 13:1551-1559). In mice, the terminal half-life of 2.5(E)mg1 was estimated to be 12 days. In similar studies, the half-lives of other human monoclonal antibodies were 10-14 days.

The pharmacokinetics of 2.5(E)mg1 were evaluated in female mice (Jackson Labs, C57BL/6n) following a single intravenous dose of 0.2 mg (equivalent to an average of 10 mg/kg). A total of 24 mice were dosed and 3 samples were drawn from each mouse. The sampling scheme extended through seven days. 2.5(E)mg1 exhibited a distribution phase followed by an elimination phase. The distribution and elimination half-life estimates were approximately 1.6 hours and 12 days, based on a two compartment open model (Table 14).

TABLE 14

Summary of key pharmacokinetic parameters of 2.5(E)mg1 derived from a single intravenous dose in mice

| $t_{1/2\alpha}$ (hr) | $t_{1/2\beta}$ (days) | $C_{max}$ (g/mL) | CL (mL/hr) | $V_{ss}$ (mL) | $V_1$ (mL) | $V_2$ (mL) | MRT (days) | AUC (hr*μg/mL) |
|---|---|---|---|---|---|---|---|---|
| 1.58 | 12.2 | 63.2 | 0.0162 | 6.82 | 3.15 | 3.67 | 17.5 | 12250 |

Disease Models

Example 2.2.L

Effect of Anti-IL-18 Antibodies in Disease Models

Example 2.2.L.1

Inhibition of LPS-Induced IFNg Production by Anti-MuIL-18 MAbs

LPS-induced IFNγ production is dependent upon IL-18 expression (Ghayur, T., et al, 1997. Nature 386:619-623.). An LPS-induced IFNγ production assay was used to determine the efficacy of 93-10C to inhibit IL-18-dependent LPS-induced IFNγ production in vivo. Mice were given a single iv dose of 93-10C (50 μg). Thirty minutes later mice were challenged with LPS (20 mg/kg) and bled 4 h later. Serum IFNγ titers were determined by ELISA. As shown in Table 15, 93-10C inhibited LPS-induced IFNγ production by ~70%.

TABLE 15

93-10C inhibits LPS-induced IFNg production in vivo

| Group | muIFNg (pg/ml) | % Inhibition |
|---|---|---|
| Rat IgG 250 μg/mouse | 7239 ± 365 | N/A |
| MET 93-10C 250 μg/mouse | 2395 ± 711 | 67 |

Example 2.2.L.2

Inhibition of Carrageenan-Induced Paw Edema

IL-18 is involved in neutrophil recruitment to sites of inflammation. Carrageenan-induced foodpad edema is a monocyte and neutrophil-dependent inflammation model. Edema in this model can be significantly inhibited by neutralizing the biological activity of IL-18 (Leung, B. P., et al (2001) J. Immunol. 167:2879-2886). Mice were dosed (ip) with 1C5 (400 μg) (Hyashibara Laboratories, Japan) or 93-10C (100 μg) (Medical and Biological Laboratories (MBL) Co. Watertown Mass.) or control antibodies and then injected with carrageenan (sc) in the hind footpads. Carrageenan-induced edema was measured daily from 24 h to 96 h. 1C5 and 93-10C significantly suppressed carrageenan-induced edema (~50% inhibition) from 24 h to 96 h post challenge (Table 16). In addition to blocking neutrophil infiltration, 93-10C also blocks TNF expression at the site of inflammation in this model (Leung, B. P., et al (2001) J. Immunol. 167:2879-2886).).

TABLE 16

In vivo suppression of carrageenan-induced paw edema

| | Change in Paw Swelling (mm) Time (hrs) | | | |
|---|---|---|---|---|
| Carrageenan | 24 | 48 | 72 | 96 |
| 125-2H @ 400 | 0.357 | 0.557 | 0.543 | 0.414 |
| 1C5 @ 400 ug | 0.214 | 0.300 | 0.286 | 0.200 |
| Rat IgG @ 100 ug | 0.300 | 0.500 | 0.550 | 0.450 |
| 93-10C @ 100 ug | 0.157 | 0.271 | 0.243 | 0.157 |

P < 0.05 vs. Control IgG

Example 2.2.L.3

Collagen-Induced Arthritis

Rheumatoid arthritis (RA) is characterized by chronic inflammation of joints, and, loss of bone and articular cartilage. Although RA is thought to be an autoimmune disease, the autoantigen involved has not been identified and the precise etiology of disease is unknown. Collagen-induced arthritis (CIA) is a widely used model of RA and has histopathological features which are similar to the human disease (Bendele, A., et al (1999) Toxicol Pathol. 27:134-142; Trentham, D. E. et al (1977) J. Exp. Med. 146:857-868). In this model, genetically-susceptible mice or rats are immunized with type II collagen (CII) in complete Freund's adjuvant. The resulting polyarthritis is characterized by destruction of cartilage, bone resorption, synovitis, and periarticular inflammation (Bendele, A., et al (1999) Toxicol Pathol.

27:134-142). IL-18 KO mice on a DBA/1 background showed decreased incidence and severity of CIA when compared to wild-type mice (Wei, X. Q., et al (2000) J. Immunol. 166:517-521).

To address the role of endogenous IL-18 in the pathogenesis of CIA, mice were treated with a rabbit polyclonal IgG (BA77) that neutralizes mouse IL-18. When dosed for 14 days from the time of priming, BA77 delayed disease onset and resulted in a significant decrease in disease severity. BA77 also significantly inhibited production of IgG2a anti-collagen antibodies. These results are similar to those reported for IL-18 KO mice and confirm a role for IL-18 as an important proinflammatory cytokine in early CIA.

The data from IL-18 KO mice and anti-IL-18 IgG treated wild type mice indicate that IL-18 plays an important proinflammatory role during CII-induced primary T cell activation. To better understand the role of IL-18 during the onset of CIA, mice were immunized with CII and treatment with rat IgG or 93-10C initiated just prior to disease onset, which occurs around day 14. Treatment with 93-10C resulted in a significant delay in disease onset and severity when compared to control rat IgG (Table 17). These data show that IL-18 is a significant factor not only in T cell priming but also in promoting arthritogenic responses after activation of CII-specific T cells.

treated vs 2.5 in IgG control). In addition, 1C5 treatment also resulted in significant reduction in cytokine levels in the joints including IL-6 and IL-1β. (Data not shown)

Example 2.2.L. 5

SLE

The most studied models of lupus involve strains of mice (MRL/lpr and NZB/NZW F1) that spontaneously develop lupus-like syndrome with severe glomerulonephritis, autoantibody production (anti-DNA, anti RNP etc.), splenomegaly, lymphadenopathy, and to some extent arthritis and vasculitis. Kidney involvement is observed usually at 3-5 months of age, progresses rapidly, and by 6-10 months is fatal. Both mouse strains have been extensively studied to gain an understanding of clinical disease.

The NZB/NZW F1 (B/W) mouse model (The Jackson Laboratory, Maine, USA) was selected as the most relevant model to evaluate the effects of exogenous IL-18 on lupus-like disease progression. The onset of disease progression in B/W mice is observed usually at 7-9 months of age and by 12-14 months is fatal as a result of renal failure. To investigate the role of IL-18 in lupus pathogenesis, B/W mice were treated daily with r-muIL-18 or vehicle control beginning at 7

TABLE 17

Anti-IL-18 mAb 93-10C delayed the onset and decreased the severity of CIA

| Treatment | Mean Arthritic Score Day | | | | | | | |
|---|---|---|---|---|---|---|---|---|
|  | 11 | 12 | 13 | 14 | 15 | 16 | 17 | 18 |
| Rat IgG @200 μg | 0.00 | 0.13 | 0.13 | 0.13 | 0.27 | 0.53 | 1.20 | 1.20 |
| 93-10C @ 200 μg | 0.00 | 0.00 | 0.00 | 0.00 | 0.07 | 0.00 | 0.20 | 0.47 |
| Dexamethasone-21-P @ 1 mpk Treatment Period P < 0.05 vs. Rat IgG | 0.00 | 0.00 | 0.27 | 0.27 | 0.13 | 0.13 | 0.13 | 0.13 |
|  | 19 | 20 | 21 | 22 | 23 | 25 | 26 | 27 |
| Rat IgG @200 μg | 1.53 | 1.73 | 1.93 | 2.27 | 2.53 | 4.20 | 4.27 | 4.53 |
| 93-10C @ 200 μg | 0.47 | 0.80 | 1.00 | 1.00 | 1.13 | 2.20 | 2.27 | 2.87 |
| Dexamethasone-21-P @ 1 mpk Treatment Period P < 0.05 vs. Rat IgG | 0.07 | 0.07 | 0.07 | 0.00 | 0.00 | 0.00 | 0.07 | 0.20 |

Example 2.2.L.4

Septic Arthritis

IL-18 is an important factor in the pathogenesis of a mouse model of septic arthritis. This is generally not thought to be a model of RA, but shares some inflammatory components and pathology related to RA. In this model, disease is induced by injecting live group B *streptococci* (GBS) into knee joints. The severity of ensuing arthritis correlates with both systemic and local levels of IL-1β and IL-6, but not TNF (Tissi L., et al (1999) Infect. Immunol. 67:4545-50). Significant IL-18 levels in the joints were detected as early as 12 hours post injection with serotype IV (GBS) followed by peak IL-18 production after 5 days (~550 pg/ml in 1C5 treated vs ~30 pg/ml in IgG control). Elevated IL-18 levels were detected in the serum by day 5 post injection (~180 pg/ml in 1C5 treated vs ~20 pg/ml in IgG control).

When 1C5 was injected 1 hour prior to administration of GBS there was marked inhibition in the frequency of articular lesions from day 2 through day 10 (arthritic index: 1.0 in 1C5 months of age. Kidney function was assessed by determining the degree of proteinuria. Daily treatment of B/W mice with 50 μg/kg of IL-18 led to accelerated onset of severe proteinuria as compared to the PBS vehicle treated group. IL-18 treated B/W mice also exhibited accelerated deaths. These observations were consistent with those described above for the MRL/lpr mice and underscore a pro-inflammatory role for IL-18 in autoimmune disease.

To investigate the therapeutic effect of IL-18 blockade in a mouse model of SLE, an induction-maintenance treatment protocol in B/W mice that recapitulates clinical therapy for lupus nephritis was established. In this study, severely nephritic B/W mice received 5 weekly doses of cytoxan (induction phase) followed by chronic 1C5 or mouse IgG1 control (125-2H) treatment (maintenance phase).

Results demonstrate that in the ensuing 130 days of maintenance treatment, 1C5 significantly prolonged survival of BW mice as compared to control IgG1 125-2H. 125-2H is a mouse IgG1 mAb that does not recognize muIL-18 (P<0.05,). In addition to the prolongation of survival, the onset of severe proteinuria was delayed, and there was a reduction of IgG2a and IgG1 anti-dsDNA in 1C5 treated BW mice. The reduction of anti-ds DNA by 1C5 treatment was transient and not statistically significant. Antibody against 1C5 (mouse anti-mouse antibody [MAMA]) was detected, and preceded the loss of efficacy after day 130, as evidenced by a precipitous drop in survival and the loss of effect in the reduction of anti-ds DNA titer and proteinuria. In conclusion, despite the presence of antibody responses to 1C5, IL-18 blockade by 1C5 prolonged survival, delayed onset of severe proteinuria, and reduced anti-ds DNA titers in B/W mice. These data demonstrate a role for IL-18 in promoting inflammatory responses resulting in a loss of kidney function and ultimately death.

Example 2.2.L. 6

Multiple Sclerosis

The contribution of IL-18 to the pathogenesis of experimental allergic encephalomyelitis (EAE; a murine model of MS) was investigated. Relapsing-remitting EAE is considered to be a relevant model for the human disease due to similar disease course, clinical signs, and CNS pathology. In these studies the disease was induced in IL-18 KO mice and WT C57/B16 mice. The IL-18 KO mice showed a slight delay in onset of disease symptoms compared to WT mice, and developed significantly less severe disease at later time points (Table 18). Treatment of WT mice with BA77 (anti-mouse IL-18 IgG (250 mg, 2×/wk), at day 0 through day 14 post immunization delayed the onset of disease symptoms and significantly limited disease severity at later time points (Table 18). The protective effect of anti-IL-18 IgG could be observed at later time point even after cessation of treatment.

TABLE 18

Anti-IL-18 Ab treated mice and IL-18 knockout mice develop less severe EAE disease

|  |  | Mean Clinical Score |
|---|---|---|
|  |  | Day 14 Post Immunization |
| PLP Induced EAE in SJL/J mice | IgG(BA77) | 4 |
|  | anti-IL-18 ab | 2.7 |
|  |  | Day 18 |
| MOG Induced EAE in IL-18 KO and WT mice | WT | 3.6 |
|  | KO | 2.1 |

Example 2.2.L.7

Liver Damage

Concanavalin A (Con A)-induced liver inflammation/damage is an animal model of T-cell-mediated liver disease. Activation of intra-hepatic T-cells by Con A leads to local production of inflammatory mediators (e.g. IFNγ and Fas ligand). Fas-Fas ligand interaction results in production of IL-18 that induces further IFNγ, Fas ligand and TNF production. Thus, a positive feedback loop is established that results in liver damage and excessive production of liver enzymes such as ALT and AST from dying cells. 1C5 or 93-10C mAbs were injected (ip) 1 h prior to iv administration of 150 μg of Con A. Mice were bled 24 h post Con A injection and serum titers of liver enzymes (ALT & AST) were determined. Both 1C5 and 93-10C blocked LPS-induced elevation of liver enzymes, although 93-10C was effective at lower doses (Table 19).

TABLE 19

In vivo inhibition of ConA-induced liver inflammation by 93-10C

| Treatment | AST | stdv | ALT | stdv |
|---|---|---|---|---|
| PBS | 57 | 16 | 30 | 2 |
| ConA alone | 1138 | 416 | 1294 | 481 |
| ConA + 93-10C (50 ug) | 183 | 70 | 153 | 88 |
| ConA + 93-10C (12.5 ug) | 635 | 427 | 443 | 256 |
| ConA + rat IgG1(50 ug) | 3924 | 1062 | 3455 | 753 |

Example 2.2.L.8

Sepsis

IL-18 has emerged as an important mediator of endotoxic shock. IL-18 may be a critical mediator of endotoxin-induced lung, liver and multi-organ failure (Neeta, M. G., et al (2000) J. Immunol. 164:2644-2649). This effect of IL-18 may be dependent upon its ability to regulate production of cytotoxic mediators as well as its ability to activate innate immune responses and recruit neutrophils to the site of local inflammation. In addition, LPS challenge induces elevated serum levels of IFNγ, TNF and IL-1 and these cytokines may contribute towards LPS-induced lethality. IL-18 knockout mice challenged with LPS were deficient in LPS-induced IFNγ and produce significantly less TNF and IL-1 than WT mice (Takeda, K., et al. (1998) Immunity 8:383-390).

LPS induced lethality experiments were performed as follows. Animals were weighed on Day 0 and the appropriate dosage to be administered was determined. At T=−1 hour, animals were injected with anti-IL-18 antibodies or control antibodies in 500 μl of 0.9% saline, Intra-peritoneal (IP). At T=0, animals were injected with 20 mg/kg lipo poly saccharide (LPS) (*E. coli* serotype 0111:B4 Sigma Cat #L-4130 lot #71K4110) in 100 μl of 0.9% saline, Intra-venous (IV). Four hours later blood was obtained from the animals via cardiac puncture. Serum muIFNγ titer was determined by muIFNγ ELISA (R&D Systems).

WT mice treated with anti-muIL-18 mAbs, 1C5 or 93-10C, were protected from LPS-induced lethality (Table 20) (125-2H, which has the same inactive isotype as 1C5 but does not bind muIL-18, served as the control). In addition, anti-IL-18 IgG treated mice were reported to have reduced lung and liver damage after LPS challenge and this correlated with reduced neutrophil accumulation (Neeta, M. G., et al (2000) J. Immunol. 164:2644-2649).

TABLE 20

1C5 and 93-10C mAbs prevent high dose LPS lethality

|  | Percent Survival Time (hrs) | | | | | | | | |
|---|---|---|---|---|---|---|---|---|---|
| Lethality | 0 | 8 | 24 | 32 | 48 | 56 | 72 | 120 | 144 |
| Saline | 100 | 100 | 100 | 50 | 10 | 10 | 10 | 10 | 10 |
| 125-2H @ 400 | 100 | 100 | 80 | 70 | 10 | 10 | 10 | 10 | 10 |
| 1C5 @ 400 μg | 100 | 100 | 100 | 90 | 80 | 80 | 80 | 80 | 80 |

TABLE 20-continued

1C5 and 93-10C mAbs prevent high dose LPS lethality

| Lethality | Percent Survival Time (hrs) | | | | | | | | |
|---|---|---|---|---|---|---|---|---|---|
| | 0 | 8 | 24 | 32 | 48 | 56 | 72 | 120 | 144 |
| Saline | 100 | 100 | 90 | 40 | 10 | 10 | 10 | 10 | 10 |
| Rat IgG @ 100 μg | 100 | 100 | 100 | 100 | 70 | 40 | 40 | 40 | 40 |
| 93-10C @ 100 μg | 100 | 100 | 100 | 100 | 100 | 100 | 100 | 100 | 100 |

Example 2.2.M

Crystallization of 2.5(E) Fab Fragment

To demonstrate that the antibodies of the invention can be crystallized such that formulations and compositions comprising crystallized antibody can then be generated the following experiments were undertaken.

Example 2.2.M.1

Preparation and Purification of the 2.5(E) Antibody Fab Fragment

The 2.5(E) human IgG was expressed in CHO cells in SR-286 Media. The supernatant after lysis was filtered through a 0.5 micron filter and loaded onto a Protein A column pre-equilibrated in Protein A Buffer A (1×PBS). The IgG was then eluted with Protein A Buffer B (0.1 M Na Acetate pH 3.5, 150 mM NaCl). The pooled IgG was concentrated to 20 mg/ml, mixed with 50% papain gel slurry, and incubated at 37° C. for 24 hours with vigorous shaking. The antibody/slurry mixture was then dialyzed against 50 mM Tris buffer pH 7.0 overnight at 4° C. to remove cysteine from the buffer. A 25 mL Protein A Sepharose 4 Fast Flow affinity column (Amersham Pharmacia) was prepared by washing with 100 mL of Buffer A (50 mM Tris pH 7.0). The dialyzed supernatant was applied to the affinity column (2 mL/min flow rate). 2.5(E)Fab fractions (monitored by UV absorbance at 280 nm) were collected in the flow-thru. Fractions containing a 2.5(E) Fab concentration greater than 0.3 mg/mL (determined by UV absorbance at 280 nm) were pooled and concentrated to ~20 mg/mL using an Ultrafree-15 Biomax 10 kDa molecular weight cut-off (MWCO) centrifugal filter device (Millipore) and frozen at −80° C. This concentrated sample was used in crystallographic experiments described below. Sample purity was assessed with SDS-PAGE.

Example 2.2.M.2

Crystallization of the 2.5(E)Fab Fragment

Frozen 2.5(E)Fab stock solution (~20 mg/mL) was thawed on ice. The Fab (2 μL) was mixed with 2 μL of a reservoir solution consisting of 25-30% polyethyleneglycol (PEG) 400, 100 mM CAPS pH 10.5 and suspended over the reservoir on the underside of a siliconized glass cover slip at about 4° C. Rod-like crystals appeared within one day. The rod-like crystals were determined to be 2.5(E) Fab fragment crystals (Data not shown).

Example 3

IL-18 Responsive Genes

Example 3.1

Materials and Methods

Throughout Example 4, the following materials and methods are used unless otherwise stated.

Example 3.1.A

Cell Treatment and RNA Preparation

Example 3.1.A.1

KG-1 cells

Approximately $3.0 \times 10^7$ KG1 cells (ATCC #CCL-246) were used for each experimental condition in four treatment groups. In the first, cells were treated with 50 ng/mL recombinant IL18 with or without a 30 min. preincubation with 10 mg/mL cycloheximide. After 30 min. or two hours cells were harvested for RNA. In the second, cells were treated with 0, 0.5, 2.0, 10 or 50 ng/mL recombinant IL18 with or without a 30 min. preincubation with 10 mg/mL cycloheximide. After two hours cells were harvested for RNA. In the third, cells were treated with 0 or 10 ng/mL TNF. Following an overnight incubation, cells were then treated with 0, 0.5, 2.0, 10 or 50 ng/mL recombinant IL18 with or without a 30 min. preincubation with 10 mg/mL cycloheximide. After two hours cells were harvested for RNA. In the final treatment group, cells were treated simultaneously with 0 or 10 ng/mL TNF and 0 or 2.0 ng/mL recombinant IL18 with or without a 30 min. preincubation with 10 mg/mL cycloheximide. After two hours cells were harvested for RNA.

Total RNA was prepared using TRIZOL Reagent (Life Technologies, Rockville, Md.). An initial phase separation was performed according to the manufacturer's protocol and was followed by an additional extraction using a half volume of phenol:chloroform:isoamyl alcohol (25:24:1, Life Technologies, Rockville, Md.). RNA precipitation and wash were performed according to the manufacturer's TRIZOL protocol instructions. Approximately 3 micrograms of RNA were electrophoresed on a 1.0% agarose/formaldehyde denaturing gel to assess quality.

For experiments requiring TNF preincubation, KG-1 cells were incubated for 12 hours with 2 ng/ml TNF prior to stimulation with 2, 10 or 40 ng/ml of IL18. RNA was prepared as described above.

Example 3.1.A.2

Human Whole Blood Assays 2.5 mL human whole blood was aliquoted into 15 mL conical tubes and treated with IL18, IL12, IL18+IL12, IL18+IL12+anti-IL18 or IL18+IL12, IL18+IL12+control antibody. Final concentrations were as follows: IL12—500 pg/mL, IL18(YK27-1)—50 ng/mL, mIgG—5 ug/mL, anti-IL18 1252H—5 ug/mL, and anti-IL18 2.5-4 ug/mL. Mixtures were incubated at 37° C. for four hours with gentle intermittent inversion. After incubation, red blood cells were removed using ammonium chloride by adding 5 mL 1× lysis buffer (PharM Lyse Ammonium Chloride Lysing Reagent diluted 1:10 in Depc). After 5 minutes on ice the mixture was centrifuged at 1200 rpm for five minutes. This procedure was repeated once yielding a white pellet of blood leukocytes. RNA was isolated subsequently using the Trizol procedure described above. For micro array analysis, all sample volumes were increased by a factor of four.

Example 3.1.B

Preparation of Probe and Target Hybridization

Ten micrograms of total RNA and the SuperScript Choice System for cDNA Synthesis (Gibco BRL, Gaithersburg, Md.) were used to synthesize double stranded cDNA. The synthesis was carried out according to Affymetrix (Santa Clara, Calif.) protocol, which requires T7-(dT)$_{24}$ oligomer primers (GENSET) in place of the oligo (dT) or random primers provided with the kit and incubations at 42° C. during the temperature adjustment and first strand synthesis steps. The resulting cDNA was cleaned with Phase Lock Gel Light 2 ml tubes (Eppendorf AG, Hamburg, Del.), and the pellet was suspended in 12 µL of DEPC—H$_2$O. 5 µL of the cDNA was used in conjunction with the BioArray High Yield RNA Transcript Labeling Kit (Enzo, Farmingdale, N.Y.) to produce biotin-labeled cRNA targets by in vitro transcription (IVT) from T7 RNA polymerase promoters. Free nucleotides were removed from the IVT reaction with RNeasy Mini Columns (Qiagen, Hilden, Del.). 15 µg of biotin-labeled cRNA was then fragmented according to Affymetrix protocol. The entire fragmented sample was combined with 5 µL control oligonucleotide B2 (Affymetrix), 15 µL 20× Eukaryotic Hybridization Control (Affymetrix), 3 µL sonicated salmon sperm DNA (10 mg/mL, Stratagene, La Jolla, Calif.), 3 µL acetylated BSA (50 mg/mL, Gibco BRL), 150 µL 2×MES hybridization buffer, and water to a final volume of 300 µL. Following Affymetrix protocol, Genechip HuGeneFL Arrays (Affymetrix) were pre-wet with 1×MES. The hybridization cocktails were then heated and centrifuged, and 200 µL was loaded onto the chips. The chips were spun in a 45° C. rotisserie oven for 16 hours.

Example 3.1.C

Washing, Staining, and Scanning Probe Arrays

The hybridization cocktail was removed from the chips and replaced with a non-stringent wash buffer. Chips were washed and stained using the EukGE-WS2 protocol on the GeneChip Fluidics Station 400, according to manufacturer's instruction (Affymetrix); a protocol that stained the chips with both Streptavidin Phycoerythrin (SAPE) stain solution and antibody solution. All necessary wash buffers and stains were prepared according to Affymetrix protocols. A GeneArray Scanner (Agilent, Palo Alto, Calif.) was used in conjunction with GeneChip software (Affymetrix) to scan the stained arrays.

Example 3.1.D

Data Analysis

Genechip data was transferred from Affymetrix MAS4 to Microsoft Excel then uploaded into Spotfire Decisionsite 7.0.

Example 3.2

Gene Expression Regulated by IL-18

Example 3.2.1

IL18 Alone Directly Regulates a Cohort of Genes in KG1 Cells

To determine transcripts regulated directly by IL18, cytokine titration experiments were performed using KG1 cells in the presence and absence of the protein synthesis inhibitor cycloheximide. Shown in Table 1 is a list of 62 transcripts represented by 67 different probe sets (due to redundancies on the chip) found to have be regulated two fold or more with a p value of less than 0.05 (using Student's t test) under at least one condition in the presence and absence of cycloheximide. These genes comprised a variety of functional categories including transcription factors, kinases, and secreted proteins. Because these genes are regulated without de novo protein synthesis, these genes respond directly to IL18 induced signaling. Twelve genes encode secreted proteins, and thirteen encode surface molecules (making these feasible antibody targets). The remaining genes encode nuclear and cytoplasmic proteins (see Table 21).

TABLE 21

Genes induced by IL18.

| Genbank ID | Location/ function | Gene Name | Unigene Comment | 0.5 ng/ml | 2 ng/ml | 10 ng/ml | 50 ng/ml |
|---|---|---|---|---|---|---|---|
| L29217 | kinase | CLK3 | CDC-like kinase 3 | 9.1 | 7.4 | 8.1 | 15.0 |
| D14497 | kinase | MAP3K8 | mitogen-activated protein kinase kinase kinase 8 | 6.6 | 2.9 | 5.8 | 3.9 |
| L19871 | neither | ATF3 | activating transcription factor 3 | 1.0 | 1.1 | 3.3 | 2.6 |
| U15460 | neither | BATF | basic leucine zipper transcription factor, ATF-like | 1.5 | 1.7 | 2.4 | 2.8 |
| U45878 | neither | BIRC3 | baculoviral IAP repeat-containing 3 | 7.0 | 6.2 | 10.2 | 10.0 |
| U37546 | neither | BIRC3 | baculoviral IAP repeat-containing 3 | 29.4 | 26.9 | 76.6 | 63.6 |
| U72649 | neither | BTG2 | BTG family, member 2 | 3.1 | 4.7 | 6.6 | 5.9 |
| L07765 | neither | CES1 | carboxylesterase 1 | 1.0 | 1.3 | 2.1 | 2.1 |
| M27691 | neither | CREB1 | cAMP responsive element binding protein 1 | 0.9 | 2.4 | 4.9 | 3.1 |
| HG3548- | neither | CUTL1 | cut (CCAAT displacement protein) | 2.5 | 2.1 | 1.3 | 0.7 |

TABLE 21-continued

Genes induced by IL18.

| Genbank ID | Location/ function | Gene Name | Unigene Comment | 0.5 ng/ml | 2 ng/ml | 10 ng/ml | 50 ng/ml |
|---|---|---|---|---|---|---|---|
| HT3749 | | | | | | | |
| X59131 | neither | D13S106E | highly charged protein | 2.1 | 0.5 | 1.5 | 2.3 |
| U53445 | neither | DOC1 | downregulated in ovarian cancer 1 | 2.0 | 3.3 | 3.0 | 3.8 |
| X68277 | neither | DUSP1 | dual specificity phosphatase 1 | 2.5 | 3.1 | 4.1 | 3.3 |
| U48807 | neither | DUSP4 | dual specificity phosphatase 4 | 2.0 | 2.3 | 2.9 | 2.0 |
| X52541 | neither | EGR1 | early growth response 1 | 15.5 | 12.7 | 32.4 | 20.3 |
| X63741 | neither | EGR3 | early growth response 3 | 5.9 | 7.3 | 15.1 | 9.0 |
| L07077 | neither | EHHADH | enoyl-Coenzyme A | 3.4 | 2.3 | 1.8 | 2.5 |
| M62831 | neither | ETR101 | immediate early protein | 3.4 | 5.8 | 6.3 | 6.8 |
| L19314 | neither | HRY | hairy (*Drosophila*)-homolog | 2.3 | 2.5 | 2.3 | 2.0 |
| S81914 | neither | IER3 | immediate early response 3 | 17.0 | 18.6 | 32.9 | 29.6 |
| X51345 | neither | JUNB | jun B proto-oncogene | 7.2 | 6.1 | 10.7 | 9.6 |
| U20734 | neither | JUNB | jun B proto-oncogene | 10.2 | 21.8 | 25.0 | 25.4 |
| U49957 | neither | LPP | LIM domain-containing | 2.2 | 1.1 | 2.0 | 1.9 |
| M58603 | neither | NFKB1 | nuclear factor kappa B (p105) | 1.6 | 2.0 | 2.9 | 2.3 |
| S76638 | neither | NFKB2 | nuclear factor kappa B | 1.7 | 2.2 | 3.5 | 4.3 |
| M69043 | neither | NFKBIA | nuclear factor kappa B | 9.6 | 10.4 | 15.5 | 15.8 |
| U91616 | neither | NFKBIE | nuclear factor kappa B | 11.6 | 14.8 | 20.7 | 21.0 |
| L13740 | neither | NR4A1 | nuclear receptor subfamily 4, group A, member 1 | 2.0 | 2.7 | 2.4 | 2.5 |
| HG4115-HT4385 | neither | OR1E3P | olfactory receptor | 4.5 | 12.0 | 4.2 | 4.1 |
| L20971 | neither | PDE4B | phosphodiesterase 4B, cAMP-specific | 2.4 | 2.8 | 4.2 | 3.5 |
| U64675 | neither | RANBP2L1 | RAN binding protein 2-like 1 | 1.1 | 1.8 | 2.2 | 2.2 |
| S57153 | neither | RBBP1 | retinoblastoma-binding protein 1 | 2.5 | 3.4 | 5.0 | 4.1 |
| X75042 | neither | REL | v-rel | 1.6 | 2.5 | 3.9 | 3.7 |
| M83221 | neither | RELB | v-rel | 2.3 | 2.8 | 2.8 | 2.6 |
| S59049 | neither | RGS1 | regulator of G-protein signalling 1 | 10.9 | 12.7 | 22.4 | 17.8 |
| U70426 | neither | RGS16 | regulator of G-protein signalling 16 | 3.9 | 4.7 | 7.5 | 6.7 |
| U22377 | neither | RLF | rearranged L-myc fusion sequence | 2.5 | 2.0 | 2.5 | 2.6 |
| M95787 | neither | TAGLN | transgelin | 6.6 | 4.7 | 1.0 | 1.6 |
| L47345 | neither | TCEB3 | transcription elongation factor B (110 kD, elongin A) | 3.6 | 5.3 | 2.3 | 4.2 |
| M59465 | neither | TNFAIP3 | tumor necrosis factor, alpha-induced protein 3 | 9.9 | 12.4 | 25.4 | 20.6 |
| U19261 | neither | TRAF1 | TNF receptor-associated factor 1 | 2.8 | 2.8 | 4.9 | 4.1 |
| U78798 | neither | TRAF6 | TNF receptor-associated factor 6 | 1.2 | 2.0 | 2.1 | 2.2 |
| M37435 | secreted | CSF1 | colony stimulating factor 1 (macrophage) | 2.9 | 2.9 | 2.1 | 2.6 |
| M57731 | secreted | GRO2 | GRO2 oncogene | 15.2 | 20.9 | 26.3 | 27.0 |
| X53800 | secreted | GRO3 | GRO3 oncogene | 4.1 | 5.5 | 14.8 | 9.9 |
| X04500 | secreted | IL1B | interleukin 1, beta | 2.2 | 3.4 | 5.7 | 4.7 |
| M28130 | secreted | IL8 | interleukin 8 | 6.2 | 10.0 | 13.4 | 14.5 |
| Y00787 | secreted | IL8 | interleukin 8 | 5.8 | 7.4 | 8.3 | 8.5 |
| U89922 | secreted | LTB | lymphotoxin beta (TNF superfamily, member 3) | 5.0 | 5.7 | 11.0 | 12.8 |
| M31166 | secreted | PTX3 | pentaxin-related gene, rapidly induced by IL-1 beta | 3.1 | 5.2 | 10.3 | 6.4 |
| M23178 | secreted | SCYA3 | small inducible cytokine A3 | 1.8 | 2.0 | 5.0 | 3.8 |
| M69203 | secreted | SCYA4 | small inducible cytokine A4 | 0.9 | 1.9 | 7.0 | 5.6 |
| J04130 | secreted | SCYA4 | small inducible cytokine A4 | 1.0 | 2.6 | 5.9 | 4.5 |
| M92357 | secreted | TNFAIP2 | tumor necrosis factor, alpha-induced protein 2 | 4.2 | 6.4 | 20.3 | 19.3 |
| Z32765 | surface | CD36 | CD36 antigen (collagen type I/TSP receptor) | 1.6 | 2.0 | 1.4 | 1.2 |
| Z11697 | surface | CD83 | CD83 antigen | 4.7 | 8.2 | 19.6 | 16.7 |
| M57730 | surface | EFNA1 | ephrin-A1 | 9.8 | 6.0 | 9.5 | 15.2 |
| A28102 | surface | GABRA3 | gamma-aminobutyric acid (GABA) receptor | 3.0 | 2.5 | 1.6 | 2.7 |
| M24283 | surface | ICAM1 | intercellular adhesion molecule 1 (CD54) | 7.5 | 11.5 | 14.5 | 13.9 |
| M55024 | surface | ICAM1 | intercellular adhesion molecule 1 (CD54) | 2.5 | 3.4 | 3.2 | 3.7 |
| J03171 | surface | IFNAR1 | interferon (alpha, beta and omega) receptor 1 | 3.2 | 2.5 | 2.8 | 2.6 |
| X01057 | surface | IL2RA | interleukin 2 receptor, alpha | 0.7 | 0.4 | 3.9 | 3.6 |
| L10338 | surface | SCN1B | sodium channel polypeptide | 1.8 | 2.3 | 1.5 | 1.5 |
| D79206 | surface | SDC4 | syndecan 4 (amphiglycan, ryudocan) | 4.0 | 4.2 | 7.2 | 6.1 |
| HG961-HT961 | surface | SOS1 | son of sevenless (*Drosophila*) homolog 1 | 6.3 | 6.2 | 9.1 | 9.9 |
| X83490 | surface | TNFRSF6 | tumor necrosis factor receptor member 6 | 1.1 | 1.3 | 3.8 | 3.3 |
| U19523 | neither | GCH1 | GTP cyclohydrolase 1 | | 2.1 | | |
| U37518 | surface | TNFSF10 | tumor necrosis factor member 10 | 1.4 | 1.4 | 2.3 | 1.6 |

Example 3.2.2

Cytokine Exposure History Effects KG-1 Cell Response to IL-18

Since cytokines typically appear sequentially during an immune response, the effect of preincubating KG-1 cells with TNF prior to treating with IL18 were tested. This experiment also tested the hypothesis that the cytokine exposure history of cells may effect their response to subsequent cytokine exposure. Cells were treated with 2 ng TNF 12 hours prior to adding IL18 and harvested four hours later.

IL18 regulated the expression of approximately 125 genes under these conditions (Table 2). The filtering criteria used to obtain this set of genes was less than 50% change due to TNF and a two fold or greater change due to IL18 at the 10 ng/mL and 40 ng/mL. These genes comprised a variety of functional categories including transcription factors, kinases, and secreted proteins (Table 22). In contrast to other conditions tested here, we find interferon gamma mRNA and protein to be induced by IL18 following exposure to TNF.

TABLE 22

Genes regulated by IL18 following TNF treatment.

| Genbank ID | Gene Name | Unigene Comment | Fold 10 ng | Fold 40 ng |
|---|---|---|---|---|
| J00219 | IFNG | interferon, gamma | 26.3 | 31.8 |
| U17034 | PLA2R1 | phospholipase A2 receptor 1, 180 kD | 29.6 | 28.7 |
| M57710 | LGALS3 | lectin, galactoside-binding, soluble, 3 (galectin 3) | 27.5 | 25.4 |
| X97748 | PTX3 | pentaxin-related gene, IL-1 induced | 15.2 | 13.6 |
| M27288 | OSM | oncostatin M | 23.1 | 12.0 |
| X57809 | | lambda light chain variable region | 10.9 | 10.0 |
| Y00081 | IL6 | interleukin 6 (interferon, beta 2) | 9.2 | 9.4 |
| D16583 | HDC | histidine decarboxylase | 8.0 | 9.4 |
| X07730 | KLK3 | kallikrein 3, (prostate specific antigen) | 5.6 | 8.8 |
| HG3111-HT3287 | | Homo sapiens clone HH409 unknown | 9.5 | 7.5 |
| M57732 | TCF1 | hepatic nuclear factor (HNF1) | 2.0 | 7.2 |
| U77735 | PIM2 | pim-2 oncogene | 7.1 | 7.1 |
| U96094 | SLN | sarcolipin | 12.2 | 6.1 |
| D50640 | PDE3B | phosphodiesterase 3B, cGMP-inhibited | 4.0 | 5.4 |
| X14008 | LYZ | lysozyme (renal amyloidosis) | 3.0 | 5.4 |
| M91036 | HBG2 | hemoglobin, gamma G | 3.4 | 5.4 |
| X72755 | MIG | monokine induced by gamma interferon | 5.2 | 5.2 |
| AC000099 | GRM8 | glutamate receptor, metabotropic 8 | 2.3 | 4.3 |
| D11428 | PMP22 | peripheral myelin protein 22 | 5.0 | 4.0 |
| M83667 | CEBPD | CCAAT/enhancer binding protein (C/EBP), delta | 4.3 | 4.0 |
| L19267 | DMWD | dystrophia myotonica, WD repeat motif | 3.0 | 3.8 |
| M81181 | ATP1B2 | ATPase, Na+/K+ transporting | 3.5 | 3.8 |
| U79249 | | Human clone 23839 sequence | 3.1 | 3.7 |
| U49973 | FLJ10803 | hypothetical protein FLJ10803 | 3.2 | 3.6 |
| HG870-HT870 | GOLGA3 | golgi autoantigen, golgin subfamily a, 3 | 3.5 | 3.6 |
| X13589 | CYP19 | cytochrome P450, subfamily XIX | 3.0 | 3.5 |
| AB000464 | | clone: RES4-24A | 2.9 | 3.5 |
| M96956 | TDGF1 | teratocarcinoma-derived growth factor 1 | 2.6 | 3.5 |
| U31628 | IL15RA | interleukin 15 receptor, alpha | 6.4 | 3.3 |
| D38128 | PTGIR | prostaglandin I2 (prostacyclin) receptor (IP) | 8.8 | 3.3 |
| J03507 | C7 | complement component 7 | 2.3 | 3.1 |
| M32011 | NCF2 | neutrophil cytosolic factor 2 | 3.5 | 3.0 |
| X63131 | PML | promyelocytic leukemia | 4.7 | 3.0 |
| D82326 | SLC3A1 | solute carrier family 3 | 4.0 | 3.0 |
| L10343 | PI3 | protease inhibitor 3, skin-derived (SKALP) | 2.1 | 3.0 |
| U89995 | FOXE1 | forkhead box E1 (thyroid transcription factor 2) | 2.6 | 2.9 |
| M62800 | SSA1 | (52 kD, ribonucleoprotein autoantigen SS-A/Ro) | 3.1 | 2.9 |
| AB000584 | PLAB | prostate differentiation factor | 2.4 | 2.8 |
| U37519 | ALDH8 | aldehyde dehydrogenase 8 | 2.2 | 2.7 |
| D21267 | SNAP25 | synaptosomal-associated protein, 25 kD | 2.2 | 2.7 |
| M25667 | GAP43 | growth associated protein 43 | 2.5 | 2.7 |
| L34357 | GATA4 | GATA-binding protein 4 | 2.3 | 2.7 |
| U43944 | ME1 | malic enzyme 1, NADP(+)-dependent, cytosolic | 3.0 | 2.7 |
| M16937 | HOXB7 | homeo box B7 | 2.9 | 2.6 |
| U27326 | FUT3 | fucosyltransferase 3 | 2.6 | 2.6 |
| Z23115 | BCL2L1 | BCL2-like 1 | 2.2 | 2.6 |
| HG1877-HT1917 | MBP | myelin basic protein | 2.4 | 2.6 |
| D10995 | HTR1B | 5-hydroxytryptamine (serotonin) receptor 1B | 2.5 | 2.6 |
| M91463 | SLC2A4 | solute carrier family 2 glucose transporter | 3.1 | 2.5 |
| U19878 | TMEFF1 | transmembrane with EGF and follistatin like | 2.9 | 2.4 |
| U66468 | CGR11 | cell growth regulatory with EF-hand domain | 2.2 | 2.4 |
| U44848 | NRF1 | nuclear respiratory factor 1 | 3.5 | 2.4 |
| U73328 | DLX4 | distal-less homeobox 4 | 3.2 | 2.4 |
| HG4593-HT4998 | | voltage-gated sodium channel (SCN1A) | 2.3 | 2.4 |
| X78710 | MTF1 | metal-regulatory transcription factor 1 | 2.7 | 2.4 |
| X59727 | MAPK4 | mitogen-activated protein kinase 4 | 2.3 | 2.4 |
| J03600 | ALOX5 | arachidonate 5-lipoxygenase | 2.2 | 2.3 |
| U87269 | E4F1 | E4F transcription factor 1 | 3.4 | 2.3 |
| Y10375 | PTPNS1 | tyrosine phosphatase, non-receptor substrate 1 | 4.5 | 2.2 |
| D49958 | GPM6A | glycoprotein M6A | 3.3 | 2.2 |
| U60062 | FEZ1 | fasciculation & elongation protein zeta 1 (zygin I) | 3.3 | 2.2 |
| X14830 | CHRNB1 | cholinergic receptor, nicotinic, beta polypeptide 1 | 2.4 | 2.1 |
| J04076 | EGR2 | early growth response 2 (Krox-20 homolog) | 3.0 | 2.1 |
| HG2981-HT3127 | CD44 | CD44 antigen | 2.2 | 2.1 |
| U49187 | C6ORF32 | chromosome 6 open reading frame 32 | 3.8 | 2.1 |
| X77744 | | Homo sapiens for FLJ00032 protein, partial | 2.3 | 2.1 |
| X68285 | GK | glycerol kinase | 2.4 | 2.0 |
| HG3925-HT4195 | SFTPA2 | surfactant, pulmonary-associated protein A2 | 3.9 | 2.0 |
| M26062 | IL2RB | interleukin 2 receptor, beta | 0.2 | 0.5 |
| X06182 | KIT | v-kit oncogene homolog | 0.4 | 0.5 |
| U79251 | OPCML | opioid-binding protein/cell adhesion molecule-like | 0.5 | 0.5 |

TABLE 22-continued

Genes regulated by IL18 following TNF treatment.

| Genbank ID | Gene Name | Unigene Comment | Fold 10 ng | Fold 40 ng |
|---|---|---|---|---|
| J03764 | SERPINE1 | nexin, plasminogen activator inhibitor type 1 | 0.5 | 0.5 |
| X92814 | HREV107 | similar to rat HREV107 | 0.3 | 0.5 |
| L01087 | PRKCQ | protein kinase C, theta | 0.2 | 0.5 |
| D43772 | GRB7 | growth factor receptor-bound protein 7 | 0.2 | 0.5 |
| X15880 | COL6A1 | collagen, type VI, alpha 1 | 0.5 | 0.5 |
| HG3115-HT3291 | MBP | myelin basic protein | 0.4 | 0.5 |
| X83301 | SMA3 | SMA3 | 0.5 | 0.5 |
| D87469 | CELSR2 | cadherin, EGF LAG seven-pass G-type receptor 2 | 0.4 | 0.5 |
| M11313 | A2M | alpha-2-macroglobulin | 0.4 | 0.4 |
| X64877 | HFL3 | H factor (complement)-like 3 | 0.4 | 0.4 |
| Z18859 | GNAT2 | guanine nucleotide binding protein (G protein) | 0.4 | 0.4 |
| D89077 | SLA | Src-like-adapter | 0.4 | 0.4 |
| L25444 | TAF2E | TATA box binding protein (TBP)-associated factor | 0.2 | 0.4 |
| M26665 | HTN3 | histatin 3 | 0.4 | 0.4 |
| S69790 | WASF3 | WAS protein family, member 3 | 0.4 | 0.4 |
| U79248 | | Human clone 23826 sequence | 0.4 | 0.4 |
| L15309 | ZNF141 | zinc finger protein 141 (clone pHZ-44) | 0.3 | 0.4 |
| L41147 | HTR6 | 5-hydroxytryptamine (serotonin) receptor 6 | 0.4 | 0.4 |
| X58431 | HOXB6 | homeo box B6 | 0.4 | 0.4 |
| U50360 | CAMK2G | CaM kinase II gamma | 0.2 | 0.4 |
| D88152 | ACATN | acetyl-Coenzyme A transporter | 0.4 | 0.4 |
| U38480 | RXRG | retinoid X receptor, gamma | 0.3 | 0.4 |
| X16866 | CYP2D7AP | cytochrome P450, subfamily IID | 0.4 | 0.4 |
| X70991 | NAB2 | NGFI-A binding protein 2 (ERG1 bp 2) | 0.2 | 0.4 |
| M60830 | EVI2B | ecotropic viral integration site 2B | 0.4 | 0.4 |
| M27492 | IL1R1 | interleukin 1 receptor, type I | 0.4 | 0.4 |
| Z35093 | SURF1 | surfeit 1 | 0.4 | 0.4 |
| D86425 | NID2 | nidogen 2 | 0.3 | 0.3 |
| U59914 | MADH6 | MAD) homolog 6 | 0.4 | 0.3 |
| M18255 | PRKCB1 | protein kinase C, beta 1 | 0.4 | 0.3 |
| AF000234 | P2RX4 | purinergic receptor P2X | 0.3 | 0.3 |
| S77763 | NFE2 | nuclear factor (erythroid-derived 2), 45 kD | 0.4 | 0.3 |
| U78722 | ZNF165 | zinc finger protein 165 | 0.3 | 0.3 |
| L05568 | SLC6A4 | solute carrier family 6 (serotonin), | 0.3 | 0.3 |
| L31529 | SNTB1 | syntrophin, dystrophin-associated protein A1, | 0.3 | 0.3 |
| U47054 | ART3 | ADP-ribosyltransferase 3 | 0.4 | 0.3 |
| M13955 | KRT7 | keratin 7 | 0.4 | 0.3 |
| D15049 | PTPRH | protein tyrosine phosphatase, receptor type, H | 0.4 | 0.3 |
| U03486 | GJA5 | gap junction protein, alpha 5, 40 kD (connexin 40) | 0.5 | 0.3 |
| X06256 | ITGA5 | integrin, alpha 5 | 0.4 | 0.3 |
| U22314 | REST | RE1-silencing transcription factor | 0.3 | 0.3 |
| U51096 | CDX2 | caudal type homeo box transcription factor 2 | 0.2 | 0.2 |
| D31762 | KIAA0057 | TRAM-like protein | 0.4 | 0.2 |
| M23668 | FDX1 | ferredoxin 1 | 0.2 | 0.2 |
| U53476 | WNT7A | wingless-type MMTV integration site family | 0.2 | 0.2 |
| X57206 | ITPKB | inositol 1,4,5-trisphosphate 3-kinase B | 0.2 | 0.2 |
| Z31695 | INPP5A | inositol polyphosphate-5-phosphatase, 40 kD | 0.4 | 0.2 |
| S66793 | ARR3 | arrestin 3, retinal (X-arrestin) | 0.2 | 0.2 |
| U59877 | RAB31 | RAB31, member RAS oncogene family | 0.2 | 0.2 |
| U53786 | EVPL | envoplakin | 0.2 | 0.2 |
| S83362 | LIFR | leukemia inhibitory factor receptor | 0.3 | 0.2 |
| D42038 | KIAA0087 | KIAA0087 gene product | 0.3 | 0.2 |
| HG4333-HT4603 | ZNF79 | zinc finger protein 79 (pT7) | 0.1 | 0.1 |
| L01406 | GHRHR | growth hormone releasing hormone receptor | 0.4 | 0.1 |

Example 3.2.3

Human Leukocyte Response to IL18

The response of human leukocytes (isolated leukophoresis) to respond to IL18 alone or in combination with IL12 was tested. The ability of an anti-IL18 monoclonal antibody to inhibit the transcriptional response was also tested. Cells were treated as described Example 4.1. RNA was isolated and used to probe Affymetrix Genechips (Hugene, Fla.). The results are shown in Table 23, which lists 49 transcripts induced by IL18+IL12 and reversed by anti-IL18 antibody. Several genes were relevant to the immune system. Many of these genes were also induced by IL18 in KG-1 cells.

TABLE 23

Other potential IL18/IL12 markers selected transcripts upregulated four fold or more by IL18 + IL12 and reversed by 1252H in a human leukocyte sample as determined using Affymetrix Genechips.

| Gene Name | Unigene Comment | Unigene |
|---|---|---|
| KIAA0001 | putative G protein coupled receptor for UDP-glucose | Hs.2465 |
| LIMK2 | LIM domain kinase 2 | Hs.278027 |

TABLE 23-continued

Other potential IL18/IL12 markers selected transcripts upregulated four fold or more by IL18 + IL12 and reversed by 1252H in a human leukocyte sample as determined using Affymetrix Genechips.

| Gene Name | Unigene Comment | Unigene |
|---|---|---|
| KIAA0196 | KIAA0196 gene product | Hs.8294 |
| IFNG | interferon, gamma | Hs.856 |
| POLR2C | polymerase (RNA) II polypeptide | Hs.79402 |
| DAG1 | dystroglycan 1 | Hs.76111 |
| TPSB1 | tryptase beta 1 | Hs.250700 |
| CDR2 | cerebellar degeneration-related protein (62 kD) | Hs.75124 |
| TCF12 | helix-loop-helix transcription factors 4 | Hs.21704 |
| TACTILE | T cell activation, increased late expression | Hs.142023 |
| PIP5K2A | phosphatidylinositol-4-phosphate 5-kinase | Hs.108966 |
| SF3A3 | splicing factor 3a, subunit 3, 60 kD | Hs.77897 |
| SEL1L | sel-1 (suppressor of lin-12, C. elegans)-like | Hs.181300 |
| IL15 | interleukin 15 | Hs.168132 |
| BAK1 | BCL2-antagonist/killer 1 | Hs.93213 |
| SLAM | signaling lymphocytic activation molecule | Hs.32970 |
| SCYB11 | small inducible cytokine subfamily B (Cys-X-Cys), member 11 | Hs.103982 |
| LIMK1 | LIM domain kinase 1 | Hs.36566 |
| CAT56 | CAT56 protein | Hs.118354 |
| POLRMT | polymerase (RNA) mitochondrial (DNA directed) | Hs.153880 |
| SCYA4 | small inducible cytokine A4/Mip-1b | Hs.75703 |
| MIG | monokine induced by gamma interferon | Hs.77367 |
| SSX3 | synovial sarcoma, X breakpoint 3 | Hs.178749 |
| TNFRSF6 | tumor necrosis factor receptor superfamily, member 6 | Hs.82359 |
| MAT1A | methionine adenosyltransferase I, alpha | Hs.323715 |
| KIAA0133 | KIAA0133 gene product | Hs.57730 |
| FCGBP | Fc fragment of IgG binding protein | Hs.111732 |
| ARHD | ras homolog gene family, member | Hs.15114 |
| FGFR2 | fibroblast growth factor receptor 2 | Hs.278581 |
| COL9A1 | collagen, type IX, alpha 1 | Hs.154850 |
| HPX42B | haemopoietic progenitor homeobox | Hs.125231 |
| TAL2 | T-cell acute lymphocytic leukemia 2 | Hs.247978 |
|  | ESTs | Hs.196244 |
| REN | renin | Hs.3210 |
| POU2F2 | POU domain, class 2, transcription factor 2 | Hs.1101 |
| ALOX12 | arachidonate 12-lipoxygenase | Hs.1200 |
| ACTN2 | actinin, alpha 2 | Hs.83672 |
| KLK2 | kallikrein 2, prostatic | Hs.181350 |
| RCV1 | recoverin | Hs.80539 |
| E2F4 | E2F transcription factor 4, p107/p130-binding | Hs.108371 |
| SEMA3F | immunoglobulin domain (Ig), short basic domain, secreted, (semaphorin) 3F | Hs.32981 |
| BHMT | betaine-homocysteine methyltransferase | Hs.80756 |
| EVPL | envoplakin | Hs.25482 |
| BBC3 | Bcl-2 binding component 3 | Hs.87246 |
| SLN | sarcolipin | Hs.15219 |
| RDBP | RD RNA-binding protein | Hs.106061 |
| MT1H | metallothionein 1H | Hs.2667 |
| RAD54L | RAD54 (S. cerevisiae)-like | Hs.66718 |
| MLL3 | myeloid/lymphoid or mixed-lineage leukemia3 | Hs.288971 |

Example 3.2.4

Human Whole Blood Response to IL18

The response of whole human blood to respond to IL18 alone or in combination with IL12 was tested. The ability of an anti-IL18 monoclonal antibody to inhibit the transcriptional response was also tested. Normal donor blood samples were treated as described in Example 4.1. RNA was isolated and used to probe Affymetrix Genechips (Hugene Fla.). The results are shown in Table 24 which lists 16 transcripts that were significantly regulated by IL18+IL12 and reversed by anti-IL18 antibody in whole blood samples isolated from two healthy donors. Several genes were relevant to the immune system. We went on to test the response of three of these genes in panel of 10 normal donors using quantitative PCR. The results of this human variability study are shown in Table 25, for interferon gamma; Table 26, CXCL9 and Table 27, CCL8. The results of the variability study indicated that regulation of these transcripts by IL18 in human blood is likely to be a common among humans.

TABLE 24

Other potential IL18/IL12 markers selected from transcripts up-regulated in whole blood isolated from two donors then treated with IL18 + IL12.

| Probe Set ID | Title | Unigene |
|---|---|---|
| 202284_s_at | cyclin-dependent kinase inhibitor 1A (p21, Cip1) | Hs.179665 |
| 202531_at | interferon regulatory factor 1 | Hs.80645 |
| 204057_at | interferon consensus sequence binding protein 1 | Hs.14453 |
| 205488_at | granzyme A (granzyme 1, cytotoxic T-lymphocyte-associated serine esterase 3) | Hs.90708 |
| 206554_x_at | SET domain and mariner transposase fusion gene | Hs.265855 |
| 206817_x_at | trinucleotide repeat containing 4 | Hs.26047 |
| 207509_s_at | leukocyte-associated Ig-like receptor 2 | Hs.43803 |
| 209546_s_at | apolipoprotein L, 1 | Hs.114309 |
| 214438_at | H2.0-like homeo box 1 (Drosophila) | Hs.74870 |

TABLE 24-continued

Other potential IL18/IL12 markers selected from transcripts up-regulated in whole blood isolated from two donors then treated with IL18 + IL12.

| Probe Set ID | Title | Unigene |
|---|---|---|
| 214450_at | cathepsin W (lymphopain) | Hs.87450 |
| 216950_s_at | FcRI b form (AA 1-344) [*Homo sapiens*], mRNA sequence | Hs.382006 |
| 217933_s_at | leucine aminopeptidase 3 | Hs.182579 |
| 219386_s_at | B lymphocyte activator macrophage expressed | Hs.20450 |
| 219956_at | UDP-N-acetyl-alpha-D-galactosamine: polypeptide N-acetylgalactosaminyl-transferase 6 | Hs.151678 |
| 219971_at | interleukin 21 receptor | Hs.210546 |
| 221223_x_at | cytokine inducible SH2-containing protein | Hs.8257 |

TABLE 25

Interferon γ performance in ten human blood samples. $p < 0.05$ for inhibition by either antibody

| IFN | Unstimulated | Stimulated | Anti-IL18 2.5 | Anti-IL18 125-2H |
|---|---|---|---|---|
| donor 3n | 0.001 | 0.187 | 0.014 | 0.026 |
| donor 5n | 0.003 | 0.012 | 0.006 | 0.006 |
| donor 9n | 0.001 | 1.250 | 0.037 | 0.000 |
| donor10n | 0.002 | 0.361 | 0.024 | 0.002 |
| donor1n | 0.002 | 0.339 | 0.022 | 0.070 |
| donor2n | 0.001 | 0.032 | 0.003 | 0.003 |
| donor4n | 0.001 | 0.082 | 0.011 | 0.027 |
| donor6n | 0.002 | 0.076 | 0.006 | 0.010 |
| donor7n | 0.002 | 0.049 | 0.009 | 0.012 |
| donor8n | 0.002 | 0.049 | 0.009 | 0.012 |

TABLE 26

MIG/CXCL9 performance in ten human blood samples. $p < 0.05$ for inhibition by either antibody.

| CXCL9 | Unstimulated | Stimulated | Anti-IL18 2.5 | Anti-IL18 125-2H |
|---|---|---|---|---|
| donor1 | 0.000 | 0.170 | 0.082 | 0.010 |
| donor10 | 0.000 | 0.015 | 0.000 | 0.000 |
| donor2 | 0.001 | 0.006 | 0.001 | 0.001 |
| donor3 | 0.000 | 0.067 | 0.010 | 0.006 |
| donor4 | 0.000 | 0.023 | 0.012 | 0.003 |
| donor5 | 0.000 | 0.004 | 0.000 | 0.000 |
| donor6 | 0.000 | 0.070 | 0.001 | 0.001 |
| donor7 | 0.001 | 0.034 | 0.001 | 0.000 |
| donor8 | 0.001 | 0.034 | 0.001 | 0.000 |
| donor9 | 0.000 | 0.035 | 0.000 | 0.001 |

TABLE 27

MCP2/CCL8 performance in ten human blood samples. $p < 0.05$ for inhibition by either antibody.

| CCL8 | Unstimulated | Stimulated | Anti-IL18 2.5 | Anti-IL18 125-2H |
|---|---|---|---|---|
| donor1 | 0.036 | 8.941 | 4.054 | 1.051 |
| donor10 | 0.004 | 0.987 | 0.009 | 0.025 |
| donor2 | 0.036 | 1.225 | 0.105 | 0.057 |
| donor3 | 0.012 | 3.923 | 0.648 | 0.663 |
| donor4 | 0.021 | 2.227 | 0.994 | 0.630 |
| donor5 | 0.001 | 0.005 | 0.001 | 0.001 |
| donor6 | 0.000 | 0.023 | 0.002 | 0.001 |
| donor7 | 0.001 | 0.009 | 0.001 | 0.001 |
| donor8 | 0.001 | 0.009 | 0.001 | 0.001 |
| donor9 | 0.001 | 2.438 | 0.003 | 0.059 |

Example 4

Characterization of Anti-IL-18 HuMAb, 2.13(E)mg1

Example 4.1

Human Cytokine Specificity

The specificity of 2.13(E)mg1 for human IL-18 was evaluated using the BIACORE assay following manufacturer's instructions (see Example 2.1.B). The 2.13(E)mg1 was captured on a biosensor chip and its ability to bind a panel of known human cytokines in solution was determined. As shown in Table 28, 2.13(E)mg1 bound recombinant mature human IL-18. However, 2.13(E)mg1 did not bind human proIL-18 nor did it bind any of the other 23 human cytokines tested, including the IL-1 family members IL-1α and IL-1β̃

TABLE 28

Biacore Analysis of Cytokine Binding by 2.13(E)mg1 and 2.5(E)mg1

| Soluble rec. human cytokines, (1 μM) | Captured 2.13(E)mg1 (25 mg/mL) 2.13(E)mg1 Binding | Captured 2.5(E)mg1 (25 mg/mL) 2.5(E)mg1 Binding |
|---|---|---|
| IFNγ | − | − |
| IL-1α | − | − |
| IL-1β | − | − |
| Other cytokines[a] | − | − |
| IL-18[b] | + | + |
| Pro-IL-18 | − | + |

[a] Additional cytokines tested for binding included IL-2, IL-3, IL-4, IL-5, IL-6, IL-7, IL-8, IL-9, IL-10, IL-11, IL-12, IL-13, IL-15, IL-16, IL-17, IL-21, TNF, LT, LTα1β2, and LTα2β1. 2.13(E)mg1 did not bind to any of these cytokines.

Example 4.2

Competition with Other Antibodies to Bind Human IL-18

The ability of several anti-IL-18 antibodies to compete with 2.13(E)mg1 for binding to human IL-18 was evaluated using the BIACORE assay following manufacturer's instructions (see Example 2.1.B). Briefly, polyclonal anti-human or anti-mouse antibodies were captured on a biosensor chip. Thereafter, anti-IL-18 antibodies were introduced and captured by the polyclonal anti-human or anti-mouse (only for 125-2H) antibodies immobilized on the biosensor chip described above (primary immobilized antibody). Then, recombinant human IL-18 was introduced and captured by the primary immobilized antibody. Finally, secondary soluble anti-IL-18 antibodies were introduced. The assay measured the ability of the secondary soluble anti-IL-18 to bind the recombinant IL-18 and compete with the primary antibody. 2.13(E)mg1 did not compete with either 2.5(E)mg1 or IL-18BP Murine anti-huIL-18 monoclonal antibody 125-2H competed with 2.13(E)mg1 for binding to human IL-18.

TABLE 29

BIACORE analysis of Antibody Competition for binding to human IL-18

| 2° soluble AB | 1° Immobilized Ab | | | | | | | | |
|---|---|---|---|---|---|---|---|---|---|
| | 125-2H | 2.5(E)mg1 | 215 | 444 | 581 | 435 | 2.13(E)mg1 | 2.3 | IL-18BP |
| 125-2H | − | + | − | − | + | + | − | − | + |
| 2.5(E)mg1 | + | − | + | + | − | − | + | + | + |
| 215 | − | + | − | − | + | + | − | − | + |
| 444 | − | + | − | − | + | + | − | − | + |
| 581 | + | − | + | + | − | − | + | + | + |
| 435 | + | − | + | + | − | − | + | + | + |
| 2.13(E)mg1 | − | + | − | − | + | + | − | − | + |
| 2.3 | − | + | − | − | + | + | − | − | + |
| IL-18BP | + | + | + | + | + | + | + | + | − |

+ indicates that the primary and the secondary antibodies bind simultaneously
− indicates that the secondary antibody cannot bind to the captured IL-18

The present invention incorporates by reference in their entirety techniques well known in the field of molecular biology. These techniques include, but are not limited to, techniques described in the following publications:

Ausubel, F. M. et al. eds., *Short Protocols In Molecular Biology* (4th Ed. 1999) John Wiley & Sons, NY. (ISBN 0-471-32938-X).

Lu and Weiner eds., *Cloning and Expression Vectors for Gene Function Analysis* (2001) BioTechniques Press. Westborough, Mass. 298 pp. (ISBN 1-881299-21-X).

Kontermann and Dubel eds., *Antibody Engineering* (2001) Springer-Verlag. New York. 790 pp. (ISBN 3-540-41354-5).

Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4).

Sambrook, J. et al. eds., *Molecular Cloning: A Laboratory Manual* (2d Ed. 1989) Cold Spring Harbor Laboratory Press, NY. Vols. 1-3. (ISBN 0-87969-309-6).

Winnacker, E. L. *From Genes To Clones: Introduction To Gene Technology* (1987) VCH Publishers, NY (translated by Horst Ibelgaufts). 634 pp. (ISBN 0-89573-614-4).

REFERENCRES

U.S. Patents

| 5,545,806 | 5,545,807 | 5,591,669 | 5,612,205 | 5,625,126 | 5,625,825 | 5,627,052 |
| 5,633,425 | 5,643,763 | 5,661,016 | 5,721,367 | 5,770,429 | 5,789,215 | 5,789,650 |
| 5,814,318 | 5,912,324 | 5,916,771 | 5,939,598 | 5,985,615 | 5,994,619 | 5,998,209 |
| 6,054,487 | 6,060,283 | 6,075,181 | 6,091,001 | 6,114,598 | 6,130,364 | |

U.S. patent application publication 20030186374
U.S. application Ser. No. 09/428,082

Other References

Adachi O., et al. (1998) *Immunity* 9:143-150
Akita, K. et al., (1997) *J. Biol. Chem.* 272, 26595-26603
Azzazy H., and Highsmith W. E., (2002) *Clin. Biochem.* 35:425-445
Babcock, J. S. et al. (1996) *Proc. Natl. Acad. Sci. USA* 93:7843-7848
Barbas et al. (1991) *PNAS* 88:7978-7982
Bendele, A., et al (1999) Toxicol Pathol. 27:134-142
Bird et al. (1988) *Science* 242:423-426
Clackson et al. (1991) *Nature* 352:624-628
Dinarello, C. et al. (1998) *J. Leukoc. Biol.* 63:658-654
Dinarello, C. A. (1999) *Methods* 19:121-132
Dinarello, C. A. (1999) *J. Allergy Clin. Immunol.* 103:11-24;
Durocher et al., *Nucleic Acids Research* 2002, Vol 30, No. 2
Fuchs et al. (1991) *Bio/Technology* 9:1370-1372
Garrad et al. (1991) *Bio/Technology* 9:1373-1377
Gavilondo J. V., and Larrick J. W. (2002) *BioTechniques* 29:128-145
Giege, R. and Ducruix, A. Barrett, Crystallization of Nucleic Acids and Proteins, a Practical Approach, 2nd ea., pp. 20 1-16, Oxford University Press, New York, N.Y., (1999).
Ghayur, T. et al., (1997) *Nature* 386:619-623
Ghetie, V., et al (1997) Nat. Biotechnol. 15:637-640
Gracie J. A., et al., (2003) *Journal of Leukocyte Biology* 73, 213-224

Foreign Patent Documents

| EP 712 931 | EP 850 952, | EP 864 585, | EP 0 962 531 | EP 0 974 600 | JP 111,399194, |
| IL 121554 A0 | WO 91/10741 | WO 91/17271 | WO 92/01047 | WO 92/02551 | WO 92/09690 |
| WO 92/15679 | WO 92/18619 | WO 92/20791 | WO 93/01288 | WO 94/02602 | WO 96/33735 |
| WO 96/34096 | WO 97/24441 | WO 97/29131 | WO 98/16654 | WO 98/24893 | WO 98/41232 |
| WO 98/50433 | WO 99/09063 | WO 99/22760 | WO 99/25044 | WO 99/37772 | WO 99/37773 |
| WO 99/45031 | WO 99/53049 | WO 00/37504 | WO 00/09560 | WO 00/12555 | WO 00/37504, |
| WO 00/56772 | WO 01/58956 | WO 01/83525 | WO 02/72636 | | |

Gram et al. (1992) *PNAS* 89:3576-3580
Green et al. *Nature Genetics* 7:13-21 (1994)
Green and Jakobovits *J. Exp. Med.* 188:483-495 (1998)
Griffiths et al. (1993) *EMBO J* 12:725-734
Gu, Y. et al., (1997) *Science* 275:206-209)
Hay et al. (1992) *Hum Antibod Hybridomas* 3:81-85
Harlow and Lane, *Antibodies: A Laboratory Manual*, New York: Cold Spring Harbor Press, 1990.
Hawkins et al. (1992) *J Mol Biol* 226:889-896
Hezareh, M., et. al., (2001) *J. Virology,* 75 (24):12161-12168
Holliger, P., et al. (1993) *Proc. Natl. Acad. Sci. USA* 90:6444-6448
Hoogenboom et al. (1991) *Nuc Acid Res* 19:4133-4137
Hoogenboom H. R., (1997) *TIB Tech.* 15:62-70
Hoogenboom H., and Chames P. (2000) *Immunology Today* 21:371-378
Huston et al. (1988) *Proc. Natl. Acad. Sci. USA* 85:5879-5883
Hoshino K., et al (1999) *J. Immunol.* 162:5041-5044
Huse et al. (1989) *Science* 246:1275-1281
Johnnson, B., et al. (1991) *Anal. Biochem.* 198:268-277.
Johnsson, B., et al. (1995) *J. Mol. Recognit.* 8:125-131
Jönsson, U., et al. (1991) *Biotechniques* 11:620-627
Jönsson, U., et al. (1993) *Ann. Biol. Clin.* 51:19-26
Kanakaraj P., (1999) *J. Exp. Med.* 189:1129-1138
Kaufman, R. J. and Sharp, P. A., (1982) *Mol. Biol.* 159:601-621
Kearney et al, J. Immunol. 123, 1979, 1548-1550
Kellermann S. A. and Green L. L. (2002) *Current Opinion in Biotechnology* 13:593-597
Kim J. K., et al (1999) Eur. J. Immunol. 29:2819-2825
Konishi, K., et al (1997) *J. Immunol. Methods* 209:187-191
Kipriyanov, S. M., et al. (1994) *Mol. Immunol.* 31:1047-1058
Kipriyanov, S. M., et al. (1995) *Human Antibodies and Hybridomas* 6:93-101
Leung, B. P., et al (2001) J. Immunol. 167:2879-2886
Little M. et al (2000) *Immunology Today* 21:364-370
BioTechniques Press. Westborough, Mass. 298 pp. (ISBN 1-881299-21-X).
Lund, J. et al., *J. Immunology* (1991) 147: 2657-2662
McCafferty et al., *Nature* (1990) 348:552-554
McInnes, I. B. et. al. (2000) *Immunology Today* 21:312-315;
Mendez et al., *Nature Genetics* 15:146-156 (1997)
Mizushima, S. and Nagata, S., (1990) *Nucleic acids Research* Vol 18, No. 17
Nakanishi, K. et al (2001) *Ann. Rev. Immunol* 19:423-474.
Nakanishi K., et al (2001) Cytokine and Growth Factor Rev. 12:53-72
Neeta, M. G., et al (2000) J. Immunol. 164:2644-2649
Ober, R. J., et al (2001) Int. Immunol. 13:1551-1559
Poljak, R. J., et al. (1994) *Structure* 2:1121-1123
Seidman, J. G., Smith, J. A., and K. Struhl eds; Wiley Interscience, N.Y., N.Y. (1990)
Sims, J. E., (2002) *Current Opin Immunol.* 14:117-122
Sugawara, S. et al., (2001) *J. Immunol.,* 167, 6568-6575
*Sustained and Controlled Release Drug Delivery Systems,* J. R. Robinson, ed., Marcel Dekker, Inc., New York, 1978.
Takeda, K., et al. (1998) Immunity 8:383-390
Taylor, L. D., et al. (1992) Nucl. Acids Res. 20:6287-6295
Tissi L., et al (1999) Infect. Immunol. 67:4545-50
Trentham, D. E. et al (1977) J. Exp. Med. 146:857-868
Tsutsui, H. et al., (1999) *Immunity* 11:359-67
Urlaub and Chasin, (1980) *Proc. Natl. Acad. Sci. USA* 77:4216-4220
Ushio, S., et al. (1996) J. Immunol. 156:4274-4279
Ward et al., (1989) *Nature* 341:544-546
Wei, X. Q., et al (2000) J. Immunol. 166:517-521
Winnacker, E. L. *From Genes To Clones: Introduction To Gene Technology* (1987) VCH Publishers, NY (translated by Horst Ibelgaufts). 634 pp. (ISBN 0-89573-614-4).

Although a number of embodiments and features have been described above, it will be understood by those skilled in the art that modifications and variations of the described embodiments and features may be made without departing from the present disclosure or the invention as defined in the appended claims. Each of the publications mentioned herein is incorporated by reference.

We claim:

1. An isolated binding protein capable of binding human IL-18, said binding protein comprising:
    an Ig constant heavy region having the amino acid sequence selected from the group consisting of: SEQ ID NO:2, and SEQ ID NO: 3;
    an Ig constant light region having the amino acid sequence selected from the group consisting of: SEQ ID NO:4, and SEQ ID NO: 5;
    an Ig variable heavy region having the amino acid sequence of SEQ ID NO:6; and
    an Ig variable light region having the amino acid sequence of SEQ ID NO:7.

2. An isolated binding protein capable of binding human IL-18, said binding protein comprising:
    an Ig constant heavy region having the amino acid sequence of SEQ ID NO: 3;
    an Ig constant light region having the amino acid sequence of SEQ ID NO:4;
    an Ig variable heavy region having the amino acid sequence of SEQ ID NO:6; and
    an Ig variable light region having the amino acid sequence of SEQ ID NO:7.

3. An isolated neutralizing binding protein, wherein said neutralizing binding protein comprises a binding protein according to claim 1 or 2, and wherein said neutralizing binding protein is capable of neutralizing human IL-18.

4. The isolated neutralizing binding protein according to claim 3, wherein said IL-18 is selected from the group consisting of pro-human IL-18, mature-human IL-18, and truncated-human IL-18.

5. The isolated neutralizing binding protein according to claim 3, wherein said neutralizing binding protein diminishes the ability of human IL-18 to bind to its receptor.

6. The isolated neutralizing binding protein according to claim 5, wherein said neutralizing binding protein diminishes the ability of pro-human IL-18, mature-human IL-18, or truncated-human IL-18 to bind to its receptor.

7. The isolated neutralizing binding protein according to claim 3, wherein said neutralizing binding protein is capable of reducing one or more of human IL-18 biological activities selected from the group consisting of: Th1 modulation, Th2 modulation, NK modulation, neutrophil modulation, monocyte-macrophage lineage modulation, eosinophil modulation, B-cell modulation, cytokine modulation, chemokine modulation, adhesion molecule modulation, and cell recruitment modulation.

8. The isolated neutralizing binding protein according to claim 3, wherein said neutralizing binding protein has a dissociation constant ($K_D$) selected from the group consisting of: about $10^{-7}$ M, about $10^{-8}$ M, about $10^{-9}$ M, about $10^{-10}$ M, about $10^{-12}$ M, and about $10^{-13}$ M.

9. The isolated neutralizing binding protein according to claim 3, wherein said neutralizing binding protein has an on-rate selected from the group consisting of: about $10^2$ $M^{-1}$ $s^{-1}$, about $10^3$ $M^{-1}$ $s^{-1}$, about $10^4$ $M^{-1}$ $s^{-1}$, about $10^5$ $M^{-1}$ $s^{-1}$, and about $10^6$ $M^{-1}$ $s^{-1}$.

10. The isolated neutralizing binding protein according to claim 3, wherein said neutralizing binding protein has an off-rate selected from the group consisting of: about $10^{-3}$ $s^{-1}$, about $10^{-4}$ $s^{-1}$, about $10^{-5}$ $s^{-1}$, and about $10^{-6}$ $s^{-1}$.

11. A labeled binding protein comprising a binding protein of claim 1 or 2, wherein said binding protein is conjugated to a detectable label.

12. The labeled binding protein of claim 11, wherein the detectable label is selected from the group consisting of a radiolabel, an enzyme, a fluorescent label, a luminescent label, a bioluminescent label, a magnetic label, and biotin.

13. The labeled binding protein of claim 12, wherein said label is a radiolabel selected from the group consisting of: $^{3}$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm.

14. A conjugate binding protein comprising a binding protein of claim 1 or 2, wherein said binding protein is conjugated to a therapeutic or cytotoxic agent.

15. The conjugate binding protein of claim 14, wherein said therapeutic or cytotoxic agent is selected from the group consisting of: an anti-metabolite, an alkylating agent, an antibiotic, a growth factor, a cytokine, an anti-angiogenic agent, an anti-mitotic agent, an anthracycline, toxin, and an apoptotic agent.

16. A pharmaceutical composition comprising the binding protein of claim 1 or 2, and a pharmaceutically acceptable carrier.

17. The pharmaceutical composition of claim 16, which further comprises at least one additional therapeutic agent for treating a disorder in which IL-18 activity is detrimental.

18. The pharmaceutical composition of claim 17, wherein said additional agent is selected from the group consisting of: angiogenesis inhibitors; kinase inhibitors; co-stimulation molecule blockers; adhesion molecule blockers; anti-cytokine antibody or functional fragment thereof; methotrexate; corticosteroids; cyclosporin; rapamycin; FK506; and non-steroidal anti-inflammatory agents.

19. An isolated nucleic acid encoding the binding protein according to claim 1 or 2.

20. A vector comprising the isolated nucleic acid according to claim 19.

21. The vector of claim 20 wherein said vector is selected from the group consisting of pcDNA, pTT, pTT3, pEFBOS, pBV, pJV, and pBJ.

22. An isolated host cell comprising a vector according to claim 20.

23. The host cell according to claim 22, wherein said host cell is a prokaryotic cell.

24. The host cell according to claim 23, wherein said host cell is *E. coli*.

25. The host cell according to claim 22, wherein said host cell is an eukaryotic cell.

26. The host cell according to claim 25, wherein said eukaryotic cell is selected from the group consisting of animal cell, plant cell, and fungal cell.

27. The host cell according to claim 26, wherein said eukaryotic cell is an animal cell selected from the group consisting of a mammalian cell, an avian cell, and an insect cell.

28. The host cell according to claim 27, wherein said animal cell is a CHO cell.

29. The host cell according to claim 27, wherein said host cell is COS.

30. The host cell according to claim 26, wherein said eukaryotic cell is *Saccharomyces cerevisiae*.

31. The host cell according to claim 27, wherein said animal cell is an insect Sf9 cell.

32. A method of producing a binding protein that binds human IL-18, comprising culturing the host cell of claim 22 in a culture medium under conditions sufficient to produce a binding protein that binds human IL-18.

33. An isolated binding protein comprising an antigen binding domain capable of binding human IL-18, wherein said antigen binding domain comprises a CDR-H1 having Residues 31-35 of SEQ ID NO.:6; a CDR-H2 having Residues 50-66 of SEQ ID NO.:6; a CDR-H3 having Residues 99-110 of SEQ ID NO.:6; a CDR-L1 having Residues 24-34 of SEQ ID NO.:7; a CDR-L2 having Residues 50-56 of SEQ ID NO.:7; and a CDR-L3 having Residues 89-98 of SEQ ID NO.:7.

34. The isolated binding protein according to claim 33, wherein said antigen binding domain comprises a $V_H$.

35. The isolated binding protein according to claim 34, wherein said $V_H$ comprises the amino acid sequence of SEQ ID NO: 6.

36. The isolated binding protein according to claim 33, wherein said antigen binding domain comprises a $V_L$.

37. The isolated binding protein according to claim 36, wherein said $V_L$ comprises the amino acid sequence of SEQ ID NO: 7.

38. The isolated binding protein according to claim 33, wherein said antigen binding domain comprises a $V_H$ and a $V_L$.

39. The isolated binding protein according to claim 38, wherein said $V_L$ comprises the amino acid sequence of SEQ ID NO: 7, and said $V_H$ comprises the amino acid sequence of SEQ ID NO: 6.

40. The isolated binding protein according to claim 33, further comprising a heavy chain immunoglobulin constant domain selected from the group consisting of: a human IgM constant domain; a human IgG1 constant domain; a human IgG2 constant domain; a human IgG3 constant domain; a human IgG4 constant domain; a human IgE constant domain and a human IgA constant domain.

41. The isolated binding protein according to claim 40, wherein said heavy chain immunoglobulin constant domain is a human IgG1 constant domain.

42. The isolated binding protein according to claim 41, wherein said human IgG1 constant domain comprises the amino acid sequence selected from the group consisting of SEQ ID NO.:2 and SEQ ID NO.:3.

43. The isolated binding protein according to claim 33, further comprising a light chain immunoglobulin constant domain selected from the group consisting of: a human Ig kappa constant domain; and a human Ig lambda constant domain.

44. The isolated binding protein according to claim 43, wherein said light chain immunoglobulin constant domain is a human Ig kappa constant domain comprising the amino acid sequence of SEQ ID NO.: 4.

45. The isolated binding protein according to claim 43, wherein said light chain immunoglobulin constant domain is a human Ig lambda constant domain comprising the amino acid sequence of SEQ ID NO.: 5.

46. The isolated binding protein according to claim 33, wherein said binding protein is selected from the group consisting of: an immunoglobulin molecule; an scFv; a monoclonal antibody; a human antibody; a chimeric antibody; a humanized antibody; a Fab fragment; an Fab' fragment; an F(ab')$_2$; an Fv; and a disulfide linked Fv.

47. The isolated binding protein according to claim 46, wherein said binding protein is a human antibody.

48. The isolated binding protein according to claim 33, wherein said binding protein binds human IL-18 but is not capable of competing with a binding protein selected from the group consisting of 2.5(E)mg1 antibody and IL-18BP for binding human IL-18.

49. An isolated neutralizing binding protein, wherein said neutralizing binding protein comprises a binding protein according to any one of claims 33-47, and wherein said neutralizing binding protein is capable of neutralizing human IL-18.

50. The isolated neutralizing binding protein according to claim 49, wherein said IL-18 is selected from the group consisting of pro-human IL-18, mature-human IL-18, and truncated-human IL-18.

51. The isolated neutralizing binding protein according to claim 49, wherein said neutralizing binding protein diminishes the ability of human IL-18 to bind to its receptor.

52. The isolated neutralizing binding protein according to claim 51, wherein said neutralizing binding protein diminishes the ability of pro-human IL-18, mature-human IL-18, or truncated-human IL-18 to bind to its receptor.

53. The isolated neutralizing binding protein according to claim 49, wherein said neutralizing binding protein is capable of reducing one or more of human IL-18 biological activities selected from the group consisting of: Th1 modulation, Th2 modulation, NK modulation, neutrophil modulation, monocyte-macrophage lineage modulation, eosinophil modulation, B-cell modulation, cytokine modulation, chemokine modulation, adhesion molecule modulation, and cell recruitment modulation.

54. The isolated neutralizing binding protein according to claim 49, wherein said neutralizing binding protein has a dissociation constant ($K_D$) selected from the group consisting of: about $10^{-7}$ M; about $10^{-8}$ M; about $10^{-9}$ M; about $10^{-10}$ M; about $10^{-11}$ M; about $10^{-12}$ M; and about $10^{-13}$ M.

55. The isolated neutralizing binding protein according to claim 49, wherein said neutralizing binding protein has an on-rate selected from the group consisting of: about $10^2$ $M^{-1}$ $s^{-1}$, about $10^3$ $M^{-1}$ $s^{-1}$, about $10^4$ $M^{-1}$ $s^{-1}$, about $10^5$ $M^{-1}$ $s^{-1}$, and about $10^6$ $M^{-1}$ $s^{-1}$.

56. The isolated neutralizing binding protein according to claim 49, wherein said neutralizing binding protein has an off-rate selected from the group consisting of: about $10^{-3}$ $s^{-1}$, about $10^{-4}$ $s^{-1}$, about $10^5$ $s^{-1}$, and about $10^{-6}$ $s^{-1}$.

57. A labeled binding protein comprising a binding protein of any one of claims 33-47, wherein said binding protein is conjugated to a detectable label.

58. The labeled binding protein of claim 57, wherein the detectable label is selected from the group consisting of a radiolabel, an enzyme, a fluorescent label, a luminescent label, a bioluminescent label, a magnetic label, and biotin.

59. The labeled binding protein of claim 58, wherein said label is a, radiolabel selected from the group consisting of: $^3$H, $^{14}$C, $^{35}$S, $^{90}$Y, $^{99}$C, $^{111}$In, $^{125}$I, $^{131}$I, $^{177}$Lu, $^{166}$Ho, and $^{153}$Sm.

60. A conjugate binding protein comprising a binding protein of any one of claims 33-47, wherein said binding protein is conjugated to a therapeutic or cytotoxic agent.

61. The conjugate binding protein of claim 60, wherein said therapeutic or cytotoxic agent is selected from the group consisting of: an anti-metabolite, an alkylating agent, an antibiotic, a growth factor, a cytokine, an anti-angiogenic agent, an anti-mitotic agent, an anthracycline, toxin, and an apoptotic agent.

62. A pharmaceutical composition comprising the binding protein of any one of claims 33-47, and a pharmaceutically acceptable carrier.

63. The pharmaceutical composition of claim 62, which further comprises at least one additional therapeutic agent for treating a disorder in which IL-18 activity is detrimental.

64. The pharmaceutical composition of claim 63, wherein said additional agent is selected from the group consisting of: angiogenesis inhibitors; kinase inhibitors; co-stimulation molecule blockers; adhesion molecule blockers; anti-cytokine antibody or functional fragment thereof; methotrexate; corticosteroids; cyclosporin; rapamycin; FK506; and non-steroidal anti-inflammatory agents.

\* \* \* \* \*

UNITED STATES PATENT AND TRADEMARK OFFICE
CERTIFICATE OF CORRECTION

| | | |
|---|---|---|
| PATENT NO. | : 7,968,684 B2 | Page 1 of 1 |
| APPLICATION NO. | : 10/988360 | |
| DATED | : June 28, 2011 | |
| INVENTOR(S) | : Tariq Ghayur et al. | |

It is certified that error appears in the above-identified patent and that said Letters Patent is hereby corrected as shown below:

In the References Cited, FOREIGN PATENT DOCUMENTS, at page 2, Col. 2;
"WO2008060319 A1" should be changed to --WO2008060219 A1--

In the claims

Column 149, line 34, claim 56 "about $10^5 \text{ s}^{-1}$" should be changed to --about $10^{-5} \text{ s}^{-1}$--

Column 150, line 10, claim 59 "$^{99}\text{C}$" should be changed to --$^{99}\text{Tc}$--

Signed and Sealed this
Eleventh Day of October, 2011

David J. Kappos
*Director of the United States Patent and Trademark Office*

SEQUENCE LISTING

```
<160> NUMBER OF SEQ ID NOS: 47

<210> SEQ ID NO 1
<211> LENGTH: 193
<212> TYPE: PRT
<213> ORGANISM: Homo sapiens

<400> SEQUENCE: 1

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110
```

```
Glu Asn Lys Ile Ile Ser Phe Lys Glu Met Asn Pro Pro Asp Asn Ile
            115                 120                 125

Lys Asp Thr Lys Ser Asp Ile Ile Phe Phe Gln Arg Ser Val Pro Gly
            130                 135                 140

His Asp Asn Lys Met Gln Phe Glu Ser Ser Tyr Glu Gly Tyr Phe
145                 150                 155                 160

Leu Ala Cys Glu Lys Glu Arg Asp Leu Phe Lys Leu Ile Leu Lys Lys
            165                 170                 175

Glu Asp Glu Leu Gly Asp Arg Ser Ile Met Phe Thr Val Gln Asn Glu
            180                 185                 190

Asp

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Ala Ala Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330
```

```
<210> SEQ ID NO 4
<211> LENGTH: 106
<212> TYPE: PRT
<213> ORGANISM: Homo sapiens

<400> SEQUENCE: 4
```

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

```
<210> SEQ ID NO 5
<211> LENGTH: 105
<212> TYPE: PRT
<213> ORGANISM: Homo sapiens

<400> SEQUENCE: 5
```

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

```
<210> SEQ ID NO 6
<211> LENGTH: 121
<212> TYPE: PRT
<213> ORGANISM: Homo sapiens

<400> SEQUENCE: 6
```

Glx Val Gln Leu Val Gln Ser Gly Thr Glu Val Lys Lys Pro Gly Glu
1               5                   10                  15

Ser Leu Lys Ile Ser Cys Lys Gly Ser Gly Tyr Thr Thr Ser Tyr
            20                  25                  30

Trp Ile Gly Trp Val Arg Gln Met Pro Gly Lys Gly Leu Glu Trp Met
        35                  40                  45

Gly Phe Ile Tyr Pro Gly Asp Ser Glu Thr Arg Tyr Ser Pro Thr Phe
    50                  55                  60

Gln Gly Gln Val Thr Ile Ser Ala Asp Lys Ser Phe Asn Thr Ala Phe
65                  70                  75                  80

```
Leu Gln Trp Ser Ser Leu Lys Ala Ser Asp Thr Ala Met Tyr Tyr Cys
                85                  90                  95

Ala Arg Val Gly Ser Gly Trp Tyr Pro Tyr Thr Phe Asp Ile Trp Gly
            100                 105                 110

Gln Gly Thr Met Val Thr Val Ser Ser
        115                 120

<210> SEQ ID NO 7
<211> LENGTH: 109
<212> TYPE: PRT
<213> ORGANISM: Homo sapiens

<400> SEQUENCE: 7

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Ile Ser Ser Asn
            20                  25                  30

Leu Ala Trp Tyr Gln Gln Lys Pro Gly Gln Ala Pro Arg Leu Phe Ile
        35                  40                  45

Tyr Thr Ala Ser Thr Arg Ala Thr Asp Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ser
                85                  90                  95

Ile Thr Phe Gly Gln Gly Thr Arg Leu Glu Ile Lys Arg
            100                 105

<210> SEQ ID NO 8
<211> LENGTH: 121
<212> TYPE: PRT
<213> ORGANISM: Homo sapiens

<400> SEQUENCE: 8

Glx Val Gln Leu Gln Glu Ser Gly Pro Gly Leu Val Thr Pro Ser Gln
1               5                   10                  15

Thr Leu Ser Leu Thr Cys Thr Val Ser Gly Ser Ile Ser Ser Gly
            20                  25                  30

Gly His Tyr Trp Thr Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Leu Thr Ile Ser Val Asp Thr Ser Lys Asn Gln Phe
65                  70                  75                  80

Ser Leu Lys Leu Ser Ser Val Ala Ala Ala Asp Thr Ala Val Tyr Tyr
                85                  90                  95

Cys Ala Arg Asp Arg Gly Gly Ser Gly Ser Tyr Trp Tyr Trp Gly
            100                 105                 110

Gln Gly Thr Leu Val Thr Val Ser Ser
        115                 120

<210> SEQ ID NO 9
<211> LENGTH: 109
<212> TYPE: PRT
<213> ORGANISM: Homo sapiens

<400> SEQUENCE: 9

Glu Ile Val Leu Thr Gln Ser Pro Gly Thr Leu Ser Leu Ser Pro Gly
```

```
                 1               5                  10                  15
Glu Arg Ala Thr Leu Ser Cys Arg Gly Ser Arg Ser Val Ser Ser Gly
                20                  25                  30

Tyr Leu Ala Trp Tyr Gln Gln Lys Pro Gly Gln Ala Pro Arg Leu Leu
                35                  40                  45

Ile Tyr Gly Val Ser Ile Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                 70                  75                      80

Pro Glu Asp Phe Ala Val Tyr Tyr Cys Gln Gln Tyr His Gly Ser Pro
                85                  90                  95

Leu Thr Phe Gly Gly Gly Thr Lys Val Glu Ile Lys Arg
                100                 105

<210> SEQ ID NO 10
<211> LENGTH: 118
<212> TYPE: PRT
<213> ORGANISM: Homo sapiens

<400> SEQUENCE: 10

Glx Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Arg Asn Tyr
                20                  25                  30

Tyr Trp Ser Trp Ile Arg Gln Pro Pro Gly Lys Gly Leu Glu Trp Val
                35                  40                  45

Gly Tyr Ile Tyr Ser Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
 65                 70                  75                      80

Lys Leu Ser Ser Val Thr Ala Ala Asp Thr Ala Val Tyr Tyr Cys Ala
                85                  90                  95

Arg Asp Arg Gly Gly Ala Ser Phe Phe Asp Tyr Trp Gly Gln Gly Thr
                100                 105                 110

Leu Val Thr Val Ser Ser
        115

<210> SEQ ID NO 11
<211> LENGTH: 108
<212> TYPE: PRT
<213> ORGANISM: Homo sapiens

<400> SEQUENCE: 11

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Ile Ile Gly Gly Tyr
                20                  25                  30

Leu Asn Trp Tyr Gln Gln Arg Pro Gly Lys Ala Pro Lys Phe Leu Ile
                35                  40                  45

Tyr Ser Thr Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                      80

Glu Asp Phe Ala Thr Tyr Tyr Cys Gln Gln Thr Tyr Ile Thr Pro Pro
                85                  90                  95

Thr Phe Gly Pro Gly Thr Lys Val Asp Ile Lys Arg
                100                 105
```

<210> SEQ ID NO 12
<211> LENGTH: 119
<212> TYPE: PRT
<213> ORGANISM: Homo sapiens

<400> SEQUENCE: 12

```
Glx Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Asn Ser Gly
             20                  25                  30

Asp Tyr Tyr Trp Ser Trp Ile Arg Gln His Pro Gly Lys Gly Leu Glu
         35                  40                  45

Trp Ile Gly His Ile Ser Tyr Arg Gly Thr Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Cys
                 85                  90                  95

Cys Ala Arg Asp Arg Gly Gly Gly Phe Phe Asp Leu Trp Gly Arg Gly
            100                 105                 110

Thr Leu Val Thr Val Ser Ser
            115
```

<210> SEQ ID NO 13
<211> LENGTH: 109
<212> TYPE: PRT
<213> ORGANISM: Homo sapiens

<400> SEQUENCE: 13

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Arg Ser Leu Ser Ser Gly
             20                  25                  30

Tyr Leu Ala Trp Tyr Gln Gln Lys Pro Gly Gln Ala Pro Arg Leu Leu
         35                  40                  45

Ile Tyr Gly Ala Ser Ile Arg Ala Thr Gly Ile Pro Asp Arg Phe Ser
     50                  55                  60

Gly Ser Gly Ser Ala Thr Asp Phe Thr Leu Thr Ile Ser Arg Leu Glu
 65                  70                  75                  80

Pro Glu Asp Phe Ala Val Tyr Tyr Cys Gln Gln Tyr Asn Tyr Ser Pro
                 85                  90                  95

Leu Thr Phe Gly Gly Gly Thr Arg Val Glu Ile Asn Arg
            100                 105
```

<210> SEQ ID NO 14
<211> LENGTH: 122
<212> TYPE: PRT
<213> ORGANISM: Homo sapiens

<400> SEQUENCE: 14

```
Glx Val Gln Leu Val Glu Ser Gly Gly Gly Ser Val Gln Pro Arg Gly
  1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Phe Ser Ser Ser Gly Gly Ile Ile Tyr Tyr Ala Asp Ser Val
```

-continued

```
                    50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                     85                  90                  95

Ala Arg Asp Asp Ser Ser Gly Tyr Tyr Pro Tyr Phe Phe Asp Tyr Trp
                100                 105                 110

Gly Gln Gly Thr Leu Val Thr Val Ser Ser
            115                 120

<210> SEQ ID NO 15
<211> LENGTH: 114
<212> TYPE: PRT
<213> ORGANISM: Homo sapiens

<400> SEQUENCE: 15

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Val Leu Tyr Arg
                20                  25                  30

Ser Asn Asn Lys Asn Tyr Leu Ala Trp Tyr Gln Gln Lys Ser Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Leu Thr Phe Gly Gly Gly Thr Lys Val Glu Ile
                100                 105                 110

Lys Arg

<210> SEQ ID NO 16
<211> LENGTH: 120
<212> TYPE: PRT
<213> ORGANISM: Homo sapiens

<400> SEQUENCE: 16

Glx Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Arg
                20                  25                  30

Val Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Ala Ser Lys Asn Gln Phe
 65                  70                  75                  80

Ser Leu Lys Leu Ser Ser Val Thr Ala Ala Asp Thr Ala Ile Tyr Tyr
                 85                  90                  95

Cys Ala Arg Glu Asp Ser Ser Ala Trp Val Phe Glu His Trp Gly Gln
                100                 105                 110

Gly Thr Leu Val Thr Val Ser Ser
            115                 120

<210> SEQ ID NO 17
<211> LENGTH: 109
```

```
<212> TYPE: PRT
<213> ORGANISM: Homo sapiens

<400> SEQUENCE: 17

Glu Ile Val Leu Thr Gln Ser Pro Asp Thr Leu Ser Leu Ser Pro Gly
1               5                   10                  15

Glu Arg Ala Thr Leu Ser Cys Arg Ala Ser His Ile Leu Ser Arg Asn
            20                  25                  30

Tyr Leu Ala Trp Tyr Gln Lys Pro Gly Gln Ala Pro Arg Leu Leu
        35                  40                  45

Met Tyr Gly Ile Ser Ile Arg Ala Thr Gly Ile Pro Asp Arg Phe Ser
    50                  55                  60

Gly Ser Gly Ser Gly Ala Asp Phe Thr Leu Thr Ile Asn Arg Leu Glu
65                  70                  75                  80

Pro Glu Asp Phe Ala Val Tyr Tyr Cys Gln His Tyr Asp Asn Ser Leu
                85                  90                  95

Cys Ser Phe Gly Gln Gly Thr Lys Leu Glu Val Lys Arg
            100                 105

<210> SEQ ID NO 18
<211> LENGTH: 119
<212> TYPE: PRT
<213> ORGANISM: Homo sapiens

<400> SEQUENCE: 18

Glx Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Asn Tyr
            20                  25                  30

Gly Leu His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ser Tyr Tyr Tyr Tyr Gly Met Asp Val Trp Gly Gln Gly
            100                 105                 110

Thr Thr Val Thr Val Ser Ser
        115

<210> SEQ ID NO 19
<211> LENGTH: 108
<212> TYPE: PRT
<213> ORGANISM: Homo sapiens

<400> SEQUENCE: 19

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Phe Asn Ser Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80
```

```
Glu Asp Phe Ala Val Tyr Tyr Cys Gln Gln Tyr Asn Asn Trp Thr Trp
                85                  90                  95
Thr Phe Gly Gln Gly Thr Lys Val Glu Ile Lys Arg
            100                 105

<210> SEQ ID NO 20
<211> LENGTH: 119
<212> TYPE: PRT
<213> ORGANISM: Homo sapiens

<400> SEQUENCE: 20

Glx Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Asn Ser Gly
            20                  25                  30
Asp Tyr Tyr Trp Ser Trp Ile Arg Gln His Pro Gly Lys Gly Leu Glu
        35                  40                  45
Trp Ile Gly His Ile Ser Tyr Arg Gly Thr Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Cys
                85                  90                  95
Cys Ala Arg Asp Arg Gly Gly Gly Phe Phe Asp Leu Trp Gly Arg Gly
            100                 105                 110
Thr Leu Val Thr Val Ser Ser
            115

<210> SEQ ID NO 21
<211> LENGTH: 109
<212> TYPE: PRT
<213> ORGANISM: Homo sapiens

<400> SEQUENCE: 21

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Gly
            20                  25                  30
Tyr Leu Ala Trp Tyr Gln Gln Lys Pro Gly Gln Ala Pro Arg Leu Leu
        35                  40                  45
Ile Tyr Gly Ala Ser Ile Arg Ala Thr Gly Ile Pro Asp Arg Phe Ser
    50                  55                  60
Gly Ser Gly Ser Ala Thr Asp Phe Thr Leu Thr Ile Ser Arg Leu Glu
65                  70                  75                  80
Pro Glu Asp Phe Ala Val Tyr Tyr Cys Gln Gln Tyr Gly Tyr Ser Pro
                85                  90                  95
Leu Thr Phe Gly Gly Gly Thr Arg Val Glu Ile Asn Arg
            100                 105

<210> SEQ ID NO 22
<211> LENGTH: 127
<212> TYPE: PRT
<213> ORGANISM: Homo sapiens

<400> SEQUENCE: 22

Glx Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser His Tyr
```

```
                20                  25                  30
Gly Met His Trp Val Arg Gln Ala Pro Gly Lys Gly Leu Glu Trp Val
            35                  40                  45
Ala Val Ile Ser Tyr Asp Gly Arg Asn Lys Tyr Tyr Val Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Phe Tyr Cys
                85                  90                  95
Ala Arg Glu Lys Gly Gly Ser Gly Trp Pro Pro Phe Tyr Tyr Tyr Tyr
            100                 105                 110
Gly Met Asp Val Trp Gly Gln Gly Thr Thr Val Thr Val Ser Ser
        115                 120                 125

<210> SEQ ID NO 23
<211> LENGTH: 113
<212> TYPE: PRT
<213> ORGANISM: Homo sapiens

<400> SEQUENCE: 23

Asp Ile Val Met Thr Gln Thr Pro Leu Ser Leu Ser Val Thr Pro Gly
1               5                   10                  15
Gln Pro Ala Ser Ile Ser Cys Lys Ser Ser Gln Asn Leu Leu Tyr Ser
            20                  25                  30
Asp Gly Glu Thr Tyr Leu Cys Trp Tyr Leu Gln Lys Pro Gly Gln Pro
        35                  40                  45
Pro Gln Leu Leu Ile Tyr Glu Val Ser Asn Arg Phe Ser Gly Val Pro
    50                  55                  60
Glu Arg Phe Ser Gly Ser Gly Ser Gly Thr Asp Phe Thr Leu Lys Ile
65                  70                  75                  80
Ser Arg Val Glu Ala Glu Asp Val Gly Ile Tyr Tyr Cys Met Gln Asn
                85                  90                  95
Val Gln Leu Pro Leu Thr Phe Gly Gly Gly Thr Arg Val Glu Ile Lys
            100                 105                 110
Arg

<210> SEQ ID NO 24
<211> LENGTH: 120
<212> TYPE: PRT
<213> ORGANISM: Homo sapiens

<400> SEQUENCE: 24

Glx Thr Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Arg
            20                  25                  30
Val Tyr Tyr Trp Gly Trp Ile Arg Gln Pro Pro Gly Lys Gly Leu Glu
        35                  40                  45
Trp Ile Gly Ser Ile Tyr Tyr Ser Gly Ser Thr Tyr Tyr Ser Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Ile Tyr Tyr
                85                  90                  95
Cys Ala Arg Glu Asp Ser Ser Ala Trp Val Phe Glu His Trp Gly Gln
            100                 105                 110
```

```
Gly Thr Leu Val Thr Val Ser Ser
        115                 120
```

<210> SEQ ID NO 25
<211> LENGTH: 109
<212> TYPE: PRT
<213> ORGANISM: Homo sapiens

<400> SEQUENCE: 25

```
Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ile Leu Ser Arg Asn
            20                  25                  30

Tyr Leu Ala Trp Tyr Gln Gln Lys Pro Gly Gln Ala Pro Arg Leu Leu
        35                  40                  45

Ile Tyr Gly Ile Ser Ile Arg Ala Thr Gly Ile Pro Asp Arg Phe Ser
    50                  55                  60

Gly Ser Gly Ser Gly Ala Asp Phe Thr Leu Thr Ile Asn Arg Leu Glu
65                  70                  75                  80

Pro Glu Asp Phe Ala Val Tyr Tyr Cys Gln His Tyr Asp Asn Ser Leu
                85                  90                  95

Cys Ser Phe Gly Gln Gly Thr Lys Leu Glu Val Lys Arg
                100                 105
```

<210> SEQ ID NO 26
<211> LENGTH: 120
<212> TYPE: PRT
<213> ORGANISM: Homo sapiens

<400> SEQUENCE: 26

```
Glx Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asp Ser Arg
            20                  25                  30

Ile Tyr Tyr Trp Gly Trp Ile Arg Gln Pro Pro Gly Lys Gly Leu Glu
        35                  40                  45

Trp Ile Gly Ser Ile Tyr Tyr Arg Gly Ser Thr Tyr Tyr Asn Pro Ser
    50                  55                  60

Leu Lys Ser Arg Val Thr Ile Ser Val Asp Thr Pro Lys Asn Gln Phe
65                  70                  75                  80

Ser Leu Lys Leu Asn Ser Val Thr Ala Ala Asp Thr Ala Val Tyr Tyr
                85                  90                  95

Cys Ala Arg Glu Asp Ser Ser Ala Trp Val Phe Asp Tyr Trp Gly Gln
                100                 105                 110

Gly Thr Leu Ala Thr Val Ser Ser
        115                 120
```

<210> SEQ ID NO 27
<211> LENGTH: 109
<212> TYPE: PRT
<213> ORGANISM: Homo sapiens

<400> SEQUENCE: 27

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Asn Asn
            20                  25                  30

Tyr Leu Asn Trp Tyr Gln Gln Lys Pro Gly Gln Ala Pro Arg Leu Leu
        35                  40                  45
```

```
Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Val Val Tyr Tyr Cys Gln Gln Tyr Gly Asn Ser Ile
                85                  90                  95

Asp Ser Phe Gly Gln Gly Thr Lys Leu Glu Ile Asn Arg
            100                 105
```

<210> SEQ ID NO 28
<211> LENGTH: 119
<212> TYPE: PRT
<213> ORGANISM: Homo sapiens

<400> SEQUENCE: 28

```
Glx Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Asn Ser Gly
            20                  25                  30

Asp Tyr Tyr Trp Ser Tyr Ile Arg Gln His Pro Gly Lys Gly Leu Glu
            35                  40                  45

Trp Ile Gly His Ile Ser Tyr Arg Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Cys
                85                  90                  95

Cys Ala Arg Asp Arg Gly Gly Gly Phe Phe Asp Leu Trp Gly Arg Gly
            100                 105                 110

Thr Leu Val Thr Val Ser Ser
            115
```

<210> SEQ ID NO 29
<211> LENGTH: 109
<212> TYPE: PRT
<213> ORGANISM: Homo sapiens

<400> SEQUENCE: 29

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Gly
            20                  25                  30

Tyr Leu Ala Trp Tyr Gln Arg Lys Pro Gly Gln Ala Pro Arg Leu Leu
            35                  40                  45

Ile Tyr Gly Thr Ser Ile Arg Ala Thr Gly Ile Pro Asp Arg Phe Ser
    50                  55                  60

Gly Ser Gly Ser Ala Thr Asp Phe Thr Leu Ser Ile Ser Arg Leu Gly
65                  70                  75                  80

Pro Glu Asp Phe Ala Val Tyr Tyr Cys Gln Gln Tyr Gly Tyr Ser Pro
                85                  90                  95

Leu Thr Phe Gly Gly Gly Thr Arg Val Glu Ile Asn Arg
            100                 105
```

<210> SEQ ID NO 30
<211> LENGTH: 120
<212> TYPE: PRT
<213> ORGANISM: Homo sapiens

```
<400> SEQUENCE: 30

Glx Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
        35                  40                  45

Trp Ile Gly Tyr Ile Tyr Tyr Ser Gly Ser Thr His Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Arg Ser Val Ser Ala Ala Asp Thr Ala Gly Tyr Tyr
            85                  90                  95

Cys Ala Ser Leu Tyr Asn Gly Asn Gly Tyr Phe Asp Leu Trp Gly Arg
        100                 105                 110

Gly Thr Leu Val Thr Val Ser Ser
        115                 120

<210> SEQ ID NO 31
<211> LENGTH: 109
<212> TYPE: PRT
<213> ORGANISM: Homo sapiens

<400> SEQUENCE: 31

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Gly
            20                  25                  30

Tyr Leu Ala Trp Tyr Gln Gln Lys Pro Gly Gln Ala Pro Arg Leu Ile
        35                  40                  45

Ile Tyr Gly Val Ser Arg Arg Ala Thr Gly Ile Pro Asp Arg Phe Ser
50                  55                  60

Gly Ser Gly Ser Gly Ala Asp Phe Thr Leu Thr Ile Ser Arg Leu Asp
65                  70                  75                  80

Pro Glu Asp Phe Val Val Tyr Tyr Cys Gln Gln Tyr Gly Phe Ser Pro
            85                  90                  95

Leu Thr Phe Gly Gly Gly Thr Lys Val Glu Ile Lys Arg
        100                 105

<210> SEQ ID NO 32
<211> LENGTH: 120
<212> TYPE: PRT
<213> ORGANISM: Homo sapiens

<400> SEQUENCE: 32

Glx Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Ser
            20                  25                  30

Tyr Asp Tyr Trp Gly Trp Ile Arg Gln Pro Pro Gly Lys Gly Leu Glu
        35                  40                  45

Trp Ile Gly Ser Ile Tyr Tyr Arg Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95
```

```
Cys Ala Arg Glu Tyr Ser Thr Thr Trp Ser Ile Asp Tyr Trp Gly Gln
                100                 105                 110
Gly Thr Leu Val Thr Val Ser Ser
        115                 120

<210> SEQ ID NO 33
<211> LENGTH: 109
<212> TYPE: PRT
<213> ORGANISM: Homo sapiens

<400> SEQUENCE: 33

Glu Asn Val Leu Thr Gln Ser Pro Gly Thr Leu Ser Leu Ser Pro Gly
1               5                   10                  15
Glu Arg Ala Thr Leu Ser Cys Arg Ala Ser Gln Ser Ile Arg Asn Asn
            20                  25                  30
Tyr Leu Ala Trp Tyr Gln Gln Lys Pro Gly Gln Ala Pro Arg Leu Leu
        35                  40                  45
Ile His Gly Ala Ser Ser Arg Ala Thr Gly Ile Pro Asp Arg Phe Gly
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Phe Cys Gln Gln Tyr Gly Asn Ser Ile
                85                  90                  95
Ile Thr Phe Gly Pro Gly Thr Lys Val Asp Val Asn Arg
                100                 105

<210> SEQ ID NO 34
<211> LENGTH: 119
<212> TYPE: PRT
<213> ORGANISM: Homo sapiens

<400> SEQUENCE: 34

Glx Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Asn Ser Gly
            20                  25                  30
Gly Tyr Tyr Trp Ser Trp Ile Arg Gln His Pro Gly Lys Gly Leu Glu
        35                  40                  45
Trp Ile Gly His Ile Ser Tyr Arg Gly Thr Thr Tyr Ser Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg Asp Arg Gly Gly Phe Phe Asp Leu Trp Gly Arg Gly
                100                 105                 110
Thr Leu Val Thr Val Ser Ser
        115

<210> SEQ ID NO 35
<211> LENGTH: 109
<212> TYPE: PRT
<213> ORGANISM: Homo sapiens

<400> SEQUENCE: 35

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Asn Ser Gly
```

```
            20                  25                  30
Tyr Leu Ala Trp Tyr Gln Gln Lys Pro Gly Gln Ala Pro Arg Leu Leu
        35                  40                  45

Ile Tyr Gly Val Ser Ile Arg Ala Thr Asp Ile Pro Asp Arg Phe Ser
    50                  55                  60

Gly Ser Gly Ser Ala Thr Asp Phe Thr Leu Thr Ile Ser Arg Leu Glu
65                  70                  75                  80

Pro Glu Asp Phe Ala Val Tyr Tyr Cys Gln Gln Tyr Gly Phe Ser Pro
                85                  90                  95

Leu Thr Phe Gly Gly Gly Thr Arg Val Glu Ile Asn Arg
            100                 105

<210> SEQ ID NO 36
<211> LENGTH: 127
<212> TYPE: PRT
<213> ORGANISM: Homo sapiens

<400> SEQUENCE: 36

Glx Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Cys
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Gly Gly Ser Gly Ser Pro Pro Phe Tyr Tyr Tyr Tyr
            100                 105                 110

Gly Met Asp Val Trp Gly Gln Gly Thr Thr Val Thr Val Ser Ser
        115                 120                 125

<210> SEQ ID NO 37
<211> LENGTH: 113
<212> TYPE: PRT
<213> ORGANISM: Homo sapiens

<400> SEQUENCE: 37

Asp Ile Leu Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Gly
            20                  25                  30

Asp Gly Lys Thr Tyr Leu Tyr Trp Tyr Leu Gln Lys Pro Gly Gln Pro
        35                  40                  45

Pro Gln Phe Leu Ile Gln Glu Leu Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Gln Leu Pro Leu Thr Phe Gly Gly Gly Thr Lys Val Gln Ile Lys
            100                 105                 110

Arg
```

```
<210> SEQ ID NO 38
<211> LENGTH: 119
<212> TYPE: PRT
<213> ORGANISM: Homo sapiens

<400> SEQUENCE: 38

Glx Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Ala Asp Ser Val
    50                  55                  60

Lys Gly Arg Val Thr Ile Ser Arg Asp Asn Ser Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Tyr Tyr Tyr Gly Met Asp Val Trp Gly Gln Gly
            100                 105                 110

Thr Thr Val Thr Val Ser Ser
        115

<210> SEQ ID NO 39
<211> LENGTH: 109
<212> TYPE: PRT
<213> ORGANISM: Homo sapiens

<400> SEQUENCE: 39

Glu Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Asn Val Ser Ser Ser
            20                  25                  30

Tyr Leu Ala Trp Tyr Gln Gln Asn Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Glu Val Tyr Tyr Cys Gln Gln Ser Gly Ser Ser Leu
                85                  90                  95

Phe Thr Phe Gly Pro Gly Thr Lys Val Asp Ile Lys Arg
            100                 105

<210> SEQ ID NO 40
<211> LENGTH: 120
<212> TYPE: PRT
<213> ORGANISM: Homo sapiens

<400> SEQUENCE: 40

Glx Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Arg Ser Gly
            20                  25                  30

Asp His Tyr Trp Thr Trp Ile Arg Gln His Pro Gly Lys Gly Leu Glu
        35                  40                  45

Trp Ile Gly His Ile Tyr Tyr Ser Gly Ser Thr Tyr Tyr Asn Pro Ser
    50                  55                  60
```

-continued

Leu Lys Ser Arg Leu Thr Ile Ser Ile Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Tyr Gly Gly Asn Gly Tyr Phe Asp Tyr Trp Gly Gln
            100                 105                 110

Gly Thr Leu Val Thr Val Ser Ser
        115                 120

<210> SEQ ID NO 41
<211> LENGTH: 114
<212> TYPE: PRT
<213> ORGANISM: Homo sapiens

<400> SEQUENCE: 41

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
                20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
        50                  55                  60

Pro Asp Arg Phe Ser Gly Ser Gly Ser Gly Thr Asp Phe Thr Leu Asn
65                  70                  75                  80

Ile Ser Arg Val Glu Ala Glu Asp Val Gly Val Tyr Tyr Cys Met Gln
                85                  90                  95

Arg Ile Glu Phe Pro Ile Thr Phe Gly Gln Gly Thr Arg Leu Glu Ile
            100                 105                 110

Lys Arg

<210> SEQ ID NO 42
<211> LENGTH: 7
<212> TYPE: PRT
<213> ORGANISM: Artificial
<220> FEATURE:
<223> OTHER INFORMATION: Anti-IL-18 antibody CDR sequence
<220> FEATURE:
<221> NAME/KEY: misc_feature
<222> LOCATION: (1)
<223> OTHER INFORMATION: Xaa is Ser, Asn, His, Arg, or Tyr
<220> FEATURE:
<221> NAME/KEY: misc_feature
<222> LOCATION: (2)
<223> OTHER INFORMATION: Xaa is Tyr, Gly, Arg, Ser, or Cys
<220> FEATURE:
<221> NAME/KEY: misc_feature
<222> LOCATION: (3)
<223> OTHER INFORMATION: Xaa is Trp, Gly, Tyr, Asp, Ser, Val, or Ile
<220> FEATURE:
<221> NAME/KEY: misc_feature
<222> LOCATION: (4)
<223> OTHER INFORMATION: Xaa is Ile, His, Trp, Tyr, Met, Leu, or Asp
<220> FEATURE:
<221> NAME/KEY: misc_feature
<222> LOCATION: (5)
<223> OTHER INFORMATION: Xaa is Gly, Tyr, Ser, Asn, or His
<220> FEATURE:
<221> NAME/KEY: misc_feature
<222> LOCATION: (6)
<223> OTHER INFORMATION: Xaa is Trp, or is not present
<220> FEATURE:
<221> NAME/KEY: misc_feature
<222> LOCATION: (7)
<223> OTHER INFORMATION: Xaa is Thr, Ser, Gly, or is not present

<400> SEQUENCE: 42

Xaa Xaa Xaa Xaa Xaa Xaa Xaa
1               5

<210> SEQ ID NO 43
<211> LENGTH: 17
<212> TYPE: PRT
<213> ORGANISM: Artificial
<220> FEATURE:
<223> OTHER INFORMATION: Anti-IL-18 antibody CDR sequence
<220> FEATURE:
<221> NAME/KEY: misc_feature
<222> LOCATION: (1)
<223> OTHER INFORMATION: Xaa is Phe, Tyr, His, Ser, or Val
<220> FEATURE:
<221> NAME/KEY: misc_feature
<222> LOCATION: (2)
<223> OTHER INFORMATION: Xaa is Ile, or Phe
<220> FEATURE:
<221> NAME/KEY: misc_feature
<222> LOCATION: (3)
<223> OTHER INFORMATION: Xaa is Tyr, Ser, or Trp
<220> FEATURE:
<221> NAME/KEY: misc_feature
<222> LOCATION: (4)
<223> OTHER INFORMATION: Xaa is Pro, Tyr, or Ser
<220> FEATURE:
<221> NAME/KEY: misc_feature
<222> LOCATION: (5)
<223> OTHER INFORMATION: Xaa is Gly, Ser, Arg, or Asp
<220> FEATURE:
<221> NAME/KEY: misc_feature
<222> LOCATION: (6)
<223> OTHER INFORMATION: Xaa is Asp, or Gly
<220> FEATURE:
<221> NAME/KEY: misc_feature
<222> LOCATION: (7)
<223> OTHER INFORMATION: Xaa is Ser, Thr, Gly, or Arg
<220> FEATURE:
<221> NAME/KEY: misc_feature
<222> LOCATION: (8)
<223> OTHER INFORMATION: Xaa is Glu, Thr, Ile, or Asn
<220> FEATURE:
<221> NAME/KEY: misc_feature
<222> LOCATION: (9)
<223> OTHER INFORMATION: Xaa is Thr, Tyr, Asn, Ile, Lys, or His
<220> FEATURE:
<221> NAME/KEY: misc_feature
<222> LOCATION: (10)
<223> OTHER INFORMATION: Xaa is Arg , Tyr , or Ser
<220> FEATURE:
<221> NAME/KEY: misc_feature
<222> LOCATION: (11)
<223> OTHER INFORMATION: Xaa is Tyr, Asn, or Ser
<220> FEATURE:
<221> NAME/KEY: misc_feature
<222> LOCATION: (12)
<223> OTHER INFORMATION: Xaa is Ser, Pro, Ala, or Val
<220> FEATURE:
<221> NAME/KEY: misc_feature
<222> LOCATION: (13)
<223> OTHER INFORMATION: Xaa is Pro, Ser, or Asp
<220> FEATURE:
<221> NAME/KEY: misc_feature
<222> LOCATION: (14)
<223> OTHER INFORMATION: Xaa is Thr, Leu, or Ser
<220> FEATURE:
<221> NAME/KEY: misc_feature
<222> LOCATION: (15)
<223> OTHER INFORMATION: Xaa is Phe, Lys, or Val
<220> FEATURE:
<221> NAME/KEY: misc_feature
<222> LOCATION: (16)
<223> OTHER INFORMATION: Xaa is Gln, Ser, or Lys
<220> FEATURE:
<221> NAME/KEY: misc_feature
<222> LOCATION: (17)
<223> OTHER INFORMATION: Xaa is Gly, or is not present

<400> SEQUENCE: 43

Xaa Xaa Xaa Xaa Xaa Xaa Xaa Xaa Xaa Xaa Xaa Xaa Xaa Xaa Xaa
1               5                   10                  15

Xaa

<210> SEQ ID NO 44
<211> LENGTH: 18
<212> TYPE: PRT
<213> ORGANISM: Artificial
<220> FEATURE:
<223> OTHER INFORMATION: Anti-IL-18 antibody CDR sequence
<220> FEATURE:
<221> NAME/KEY: misc_feature
<222> LOCATION: (1)
<223> OTHER INFORMATION: Xaa is Val, Asp, Glu, Ser, or Cys
<220> FEATURE:
<221> NAME/KEY: misc_feature
<222> LOCATION: (2)
<223> OTHER INFORMATION: Xaa is Gly, Arg, Asp, Ser, Lys, Leu, Tyr, or
      Ala
<220> FEATURE:
<221> NAME/KEY: misc_feature
<222> LOCATION: (3)
<223> OTHER INFORMATION: Xaa is Ser, Gly, Tyr, or Arg
<220> FEATURE:
<221> NAME/KEY: misc_feature
<222> LOCATION: (4)
<223> OTHER INFORMATION: Xaa is Gly, Ser, Tyr, Asn, Thr, or Asp
<220> FEATURE:
<221> NAME/KEY: misc_feature
<222> LOCATION: (5)
<223> OTHER INFORMATION: Xaa is Trp, Ser, Ala, Gly, Tyr, or Thr
<220> FEATURE:
<221> NAME/KEY: misc_feature
<222> LOCATION: (6)
<223> OTHER INFORMATION: Xaa is Tyr, Gly, Ser, Phe, Trp, or Asn
<220> FEATURE:
<221> NAME/KEY: misc_feature
<222> LOCATION: (7)
<223> OTHER INFORMATION: Xaa is Pro, Ser, Phe, Tyr, Val, Gly, Trp, or
      Val
<220> FEATURE:
<221> NAME/KEY: misc_feature
<222> LOCATION: (8)
<223> OTHER INFORMATION: Xaa is Tyr, Phe, Asp, Pro, Met, Ile, or Asn
<220> FEATURE:
<221> NAME/KEY: misc_feature
<222> LOCATION: (9)
<223> OTHER INFORMATION: Xaa is Thr, Trp, Asp, Leu, Tyr, Glu, Pro, Phe,
      or Gly
<220> FEATURE:
<221> NAME/KEY: misc_feature
<222> LOCATION: (10)
<223> OTHER INFORMATION: Xaa is Phe, Asp, Tyr, His, Val, Tyr, or is not
      present
<220> FEATURE:
<221> NAME/KEY: misc_feature
<222> LOCATION: (11)
<223> OTHER INFORMATION: Xaa is Asp, Tyr, Phe, Leu, or is not present
<220> FEATURE:
<221> NAME/KEY: misc_feature
<222> LOCATION: (12)
<223> OTHER INFORMATION: Xaa is Ile, Asp, Tyr, or is not present
<220> FEATURE:
<221> NAME/KEY: misc_feature
<222> LOCATION: (13)
<223> OTHER INFORMATION: Xaa is Tyr, or is not present
<220> FEATURE:
<221> NAME/KEY: misc_feature
<222> LOCATION: (14)
<223> OTHER INFORMATION: Xaa is Tyr, or is not present
<220> FEATURE:
<221> NAME/KEY: misc_feature
<222> LOCATION: (15)
<223> OTHER INFORMATION: Xaa is Gly, or is not present
<220> FEATURE:

-continued

```
<221> NAME/KEY: misc_feature
<222> LOCATION: (16)
<223> OTHER INFORMATION: Xaa is Met, or is not present
<220> FEATURE:
<221> NAME/KEY: misc_feature
<222> LOCATION: (17)
<223> OTHER INFORMATION: Xaa is Asp, or is not present
<220> FEATURE:
<221> NAME/KEY: misc_feature
<222> LOCATION: (18)
<223> OTHER INFORMATION: Xaa is Val, or is not present

<400> SEQUENCE: 44

Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 45
<211> LENGTH: 17
<212> TYPE: PRT
<213> ORGANISM: Artificial
<220> FEATURE:
<223> OTHER INFORMATION: Anti-IL-18 antibody CDR sequence
<220> FEATURE:
<221> NAME/KEY: misc_feature
<222> LOCATION: (1)
<223> OTHER INFORMATION: Xaa is Arg, or Lys
<220> FEATURE:
<221> NAME/KEY: misc_feature
<222> LOCATION: (2)
<223> OTHER INFORMATION: Xaa is Ala, Gly, or Ser
<220> FEATURE:
<221> NAME/KEY: misc_feature
<222> LOCATION: (3)
<223> OTHER INFORMATION: Xaa is Ser
<220> FEATURE:
<221> NAME/KEY: misc_feature
<222> LOCATION: (4)
<223> OTHER INFORMATION: Xaa is Glu, Arg, Gln, or His
<220> FEATURE:
<221> NAME/KEY: misc_feature
<222> LOCATION: (5)
<223> OTHER INFORMATION: Xaa is Ser, Ile, Thr, or Asn
<220> FEATURE:
<221> NAME/KEY: misc_feature
<222> LOCATION: (6)
<223> OTHER INFORMATION: Xaa is Ile, Val, Leu, or Phe
<220> FEATURE:
<221> NAME/KEY: misc_feature
<222> LOCATION: (7)
<223> OTHER INFORMATION: Xaa is Ser, Gly, Leu, Asn, or Arg
<220> FEATURE:
<221> NAME/KEY: misc_feature
<222> LOCATION: (8)
<223> OTHER INFORMATION: Xaa is Ser, Gly, Tyr, Arg, Asn, His, or Asp
<220> FEATURE:
<221> NAME/KEY: misc_feature
<222> LOCATION: (9)
<223> OTHER INFORMATION: Xaa is Asn, Gly, Tyr, Arg, or Ser
<220> FEATURE:
<221> NAME/KEY: misc_feature
<222> LOCATION: (10)
<223> OTHER INFORMATION: Xaa is Leu, Tyr, Ser, or Asp
<220> FEATURE:
<221> NAME/KEY: misc_feature
<222> LOCATION: (11)
<223> OTHER INFORMATION: Xaa is Ala, Leu, Asn, Val, Gly, or Asp
<220> FEATURE:
<221> NAME/KEY: misc_feature
<222> LOCATION: (12)
<223> OTHER INFORMATION: Xaa is Ala, Asn, Glu, Lys, Gly, or is not
      present
<220> FEATURE:
<221> NAME/KEY: misc_feature
<222> LOCATION: (13)
<223> OTHER INFORMATION: Xaa is Lys, Thr, Asn, or is not present
<220> FEATURE:
```

```
<221> NAME/KEY: misc_feature
<222> LOCATION: (14)
<223> OTHER INFORMATION: Xaa is Asn, Tyr, Thr, or is not present
<220> FEATURE:
<221> NAME/KEY: misc_feature
<222> LOCATION: (15)
<223> OTHER INFORMATION: Xaa is Tyr, Leu, or is not present
<220> FEATURE:
<221> NAME/KEY: misc_feature
<222> LOCATION: (16)
<223> OTHER INFORMATION: Xaa is Leu, Cys, Tyr, or is not present
<220> FEATURE:
<221> NAME/KEY: misc_feature
<222> LOCATION: (17)
<223> OTHER INFORMATION: Xaa is Ala, Asp, or is not present

<400> SEQUENCE: 45

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 46
<211> LENGTH: 7
<212> TYPE: PRT
<213> ORGANISM: Artificial
<220> FEATURE:
<223> OTHER INFORMATION: Anti-IL-18 antibody CDR sequence
<220> FEATURE:
<221> NAME/KEY: misc_feature
<222> LOCATION: (1)
<223> OTHER INFORMATION: Xaa is Thr, Gly, Ser, Trp, or Glu
<220> FEATURE:
<221> NAME/KEY: misc_feature
<222> LOCATION: (2)
<223> OTHER INFORMATION: Xaa is Ala, Val, Thr, Ile, or Leu
<220> FEATURE:
<221> NAME/KEY: misc_feature
<222> LOCATION: (3)
<223> OTHER INFORMATION: Xaa is Ser, or Phe
<220> FEATURE:
<221> NAME/KEY: misc_feature
<222> LOCATION: (4)
<223> OTHER INFORMATION: Xaa is Thr, Ile, Asn, Ser, Arg, or Tyr
<220> FEATURE:
<221> NAME/KEY: misc_feature
<222> LOCATION: (5)
<223> OTHER INFORMATION: Xaa is Arg, or Leu
<220> FEATURE:
<221> NAME/KEY: misc_feature
<222> LOCATION: (6)
<223> OTHER INFORMATION: Xaa is Ala, Gln, Glu, or Phe
<220> FEATURE:
<221> NAME/KEY: misc_feature
<222> LOCATION: (7)
<223> OTHER INFORMATION: Xaa is Thr, or Ser

<400> SEQUENCE: 46

Xaa Xaa Xaa Xaa Xaa Xaa Xaa
1               5

<210> SEQ ID NO 47
<211> LENGTH: 10
<212> TYPE: PRT
<213> ORGANISM: Artificial
<220> FEATURE:
<223> OTHER INFORMATION: Anti-IL-18 antibody CDR sequence
<220> FEATURE:
<221> NAME/KEY: misc_feature
<222> LOCATION: (1)
<223> OTHER INFORMATION: Xaa is Gln, or Met
<220> FEATURE:
<221> NAME/KEY: misc_feature
<222> LOCATION: (2)
<223> OTHER INFORMATION: Xaa is Gln, His, or Tyr
<220> FEATURE:
```

```
<221> NAME/KEY: misc_feature
<222> LOCATION: (3)
<223> OTHER INFORMATION: Xaa is Tyr, Asn, Gly, Ser, or Arg
<220> FEATURE:
<221> NAME/KEY: misc_feature
<222> LOCATION: (4)
<223> OTHER INFORMATION: Xaa is Asn, His, Tyr, Asp, Gly, Val, Leu, or
      Ile
<220> FEATURE:
<221> NAME/KEY: misc_feature
<222> LOCATION: (5)
<223> OTHER INFORMATION: Xaa is Asn, Gly, Ile, Tyr, Ser, Gln, Phe, or
      Glu
<220> FEATURE:
<221> NAME/KEY: misc_feature
<222> LOCATION: (6)
<223> OTHER INFORMATION: Xaa is Trp, Ser, Thr, Leu, Ile, or Phe
<220> FEATURE:
<221> NAME/KEY: misc_feature
<222> LOCATION: (7)
<223> OTHER INFORMATION: Xaa is Pro, Leu, Thr, Asp, or Ile
<220> FEATURE:
<221> NAME/KEY: misc_feature
<222> LOCATION: (8)
<223> OTHER INFORMATION: Xaa is Ser, Leu, Pro, Cys, Trp, Ile, or Phe
<220> FEATURE:
<221> NAME/KEY: misc_feature
<222> LOCATION: (9)
<223> OTHER INFORMATION: Xaa is Ile, Thr, Ser, or is not present
<220> FEATURE:
<221> NAME/KEY: misc_feature
<222> LOCATION: (10)
<223> OTHER INFORMATION: Xaa is Thr, or is not present

<400> SEQUENCE: 47

Xaa Xaa Xaa Xaa Xaa Xaa Xaa Xaa Xaa Xaa
1               5                   10
```